United States Patent
Pitterna et al.

(10) Patent No.: US 10,687,531 B2
(45) Date of Patent: Jun. 23, 2020

(54) UREA AND THIOUREA SUBSTITUTED BICYCLES DERIVATIVES AS PESTICIDES

(71) Applicant: SYNGENTA PARTICIPATIONS AG, Basel (CH)

(72) Inventors: Thomas Pitterna, Stein (CH); André Jeanguenat, Stein (CH); Fides Benfatti, Stein (CH); Girish Rawal, Corlim (IN)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/319,310

(22) PCT Filed: Jul. 17, 2017

(86) PCT No.: PCT/EP2017/067973
§ 371 (c)(1),
(2) Date: Jan. 18, 2019

(87) PCT Pub. No.: WO2018/015328
PCT Pub. Date: Jan. 25, 2018

(65) Prior Publication Data
US 2019/0223438 A1 Jul. 25, 2019

(30) Foreign Application Priority Data
Jul. 22, 2016 (EP) .................................... 16180801

(51) Int. Cl.
| | | |
|---|---|---|
| *A01N 43/653* | (2006.01) | |
| *A01N 43/72* | (2006.01) | |
| *A01N 43/78* | (2006.01) | |
| *C07D 417/14* | (2006.01) | |
| *C07D 249/08* | (2006.01) | |
| *C07D 417/04* | (2006.01) | |
| *C07D 403/04* | (2006.01) | |
| *A01N 47/36* | (2006.01) | |
| *C07D 401/04* | (2006.01) | |
| *A01N 47/30* | (2006.01) | |
| *A01N 47/02* | (2006.01) | |
| *C07D 401/10* | (2006.01) | |
| *C07D 403/10* | (2006.01) | |
| *C07D 417/10* | (2006.01) | |

(52) U.S. Cl.
CPC ........... *A01N 43/653* (2013.01); *A01N 43/72* (2013.01); *A01N 43/78* (2013.01); *A01N 47/02* (2013.01); *A01N 47/30* (2013.01); *A01N 47/36* (2013.01); *C07D 249/08* (2013.01); *C07D 401/04* (2013.01); *C07D 401/10* (2013.01); *C07D 403/04* (2013.01); *C07D 403/10* (2013.01); *C07D 417/04* (2013.01); *C07D 417/10* (2013.01); *C07D 417/14* (2013.01)

(58) Field of Classification Search
CPC ...... A01N 43/653; A01N 43/72; A01N 43/78; A01N 47/02; A01N 47/30; A01N 47/36; C07D 249/08; C07D 401/04; C07D 401/10; C07D 403/04; C07D 403/10; C07D 417/04; C07D 417/10; C07D 417/14
USPC ........................................................ 544/292
See application file for complete search history.

(56) References Cited

U.S. PATENT DOCUMENTS

| | | | | |
|---|---|---|---|---|
| 2011/0071141 A1* | 3/2011 | Murata | ................... | A01N 43/36 514/222.8 |
| 2011/0124858 A1* | 5/2011 | Iwata | ..................... | A01N 43/80 544/105 |
| 2017/0073316 A1* | 3/2017 | Crouse | ................... | A01N 47/44 |

FOREIGN PATENT DOCUMENTS

| | | |
|---|---|---|
| WO | 2005/030151 A2 | 4/2005 |
| WO | 2014/011429 A1 | 1/2014 |
| WO | 2016/116445 A1 | 7/2016 |

OTHER PUBLICATIONS

Abdelhamid; European Journal of Chemistry 2012, 3, 322-331. DOI:10.5155/eurjchem.3.3.322-331.629 (Year: 2012).*
Patel; International Journal of Chemical Sciences, 2006, 4, 361-368: Abstract, with substance listing, 10 pages; published in Chemical Abstracts CAPLUS Database. Accession No. 2006:994891 (Year: 2006).*
International Search Report of PCT/EP2017/067973 dated Oct. 19, 2017.
Yan Li et al; "AutoT&T v.2: An Efficient and Versatile Tool for Lead Structure Generation and Optimization"; Journal of Chemical Information and Modeling, vol. 56, No. 2; pp. 435-453 , Jan. 22, 2016.

* cited by examiner

*Primary Examiner* — Daniel R Carcanague
(74) *Attorney, Agent, or Firm* — Baker & Hostetler, LLP; Toni-Junell Herbert

(57) ABSTRACT

The present invention relates to compounds of formula (I) a compound of formula (1') as defined herein, to processes for preparing them, to pesticidal, in particular insecticidal, acaricidal, molluscicidal and to combat and control pests such as insect, acarine, mollusc and nematode pests.

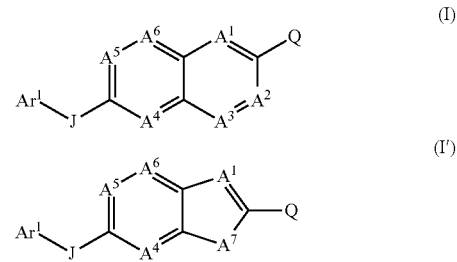

23 Claims, No Drawings

UREA AND THIOUREA SUBSTITUTED BICYCLES DERIVATIVES AS PESTICIDES

CROSS-REFERENCE TO RELATED APPLICATIONS

This application is a 371 National Stage application of International Application No. PCT/EP2017/067973, filed Jul. 17, 2017, which claims priority to European Application No. 16180801.9 filed Jul. 22, 2016, the entire contents of which applications are hereby incorporated by reference.

The present invention relates to compounds of formula (I), to processes for preparing them, to pesticidal, in particular insecticidal, acaricidal, molluscicidal and nematicidal compositions comprising them and to methods of using them to combat and control pests such as insect, acarine, mollusc and nematode pests.

Heterocyclic compounds with pesticidal activity are known and described, for example, in WO09/102736, WO11/017505, WO12/109125, WO13/116052, WO13/116053 and WO14/011429. There have now been found novel pesticidally active urea and thiourea substituted bicycles derivatives.

Accordingly, as embodiment 1 of the invention, there is provided a compound of formula (I)

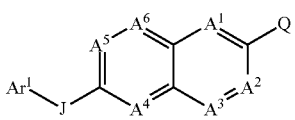
(I)

or a compound of formula (I')

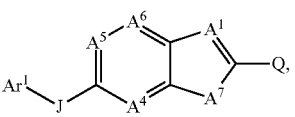
(I')

wherein Q is selected from

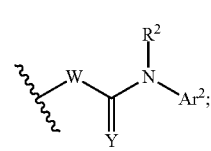
(i)

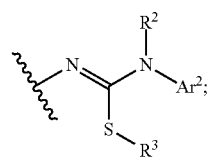
(ii)

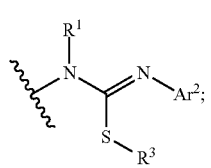
(iii)

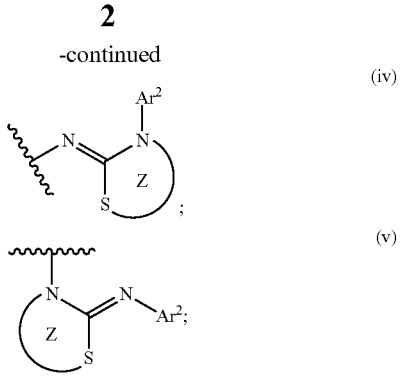

$A^1$ is N or $CR^{A1}$;
$A^2$ is N or $CR^{A2}$;
$A^3$ is N or $CR^{A3}$;
$A^4$ is N or $CR^{A4}$;
$A^5$ is N or $CR^{A5}$;
$A^6$ is N or $CR^{A6}$;
$A^7$ is O or S;
with the proviso that not more than four of $A^1$, $A^2$, $A^3$, $A^4$, $A^5$ and $A^6$ are N;
$R^{A1}$, $R^{A2}$, $R^{A3}$, $R^{A4}$, $R^{A5}$ and $R^{A6}$ are independently selected from H, $C_1$-$C_6$alkyl, $C_2$-$C_6$alkenyl, $C_2$-$C_6$alkynyl, —($C_0$-$C_6$alkyl)($C_3$-$C_6$cycloalkyl), $C_1$-$C_6$haloalkyl, $C_2$-$C_6$haloalkenyl, $C_2$-$C_6$haloalkynyl, —($C_0$-$C_6$alkyl)($C_3$-$C_6$halocycloalkyl), —($C_3$-$C_6$cycloalkyl)($C_1$-$C_3$haloalkyl), —($C_{0-6}$alkyl)-heterocyclyl, —($C_0$-$C_6$alkyl)-heteroaryl, halogen, CN, —$C_1$-$C_4$alkyl-CN, —$C_3$-$C_6$cycloalkyl-CN, $NO_2$, $C_1$-$C_6$alkoxy, $C_1$-$C_4$haloalkoxy, $C_1$-$C_4$alkoxy-$C_1$-$C_4$alkyl, —S—$C_1$-$C_6$alkyl, —S(=O)—$C_1$-$C_6$alkyl, —S(=O)$_2$ $C_1$-$C_6$alkyl, —S(=O)(=NH)$C_1$-$C_6$alkyl, —NH—$C_1$-$C_6$alkyl, —N($C_1$-$C_6$alkyl)$_2$, —NH—$C_3$-$C_6$cycloalkyl, —N($C_1$-$C_6$alkyl)($C_3$-$C_6$cycloalkyl), —C(=O)$C_1$-$C_6$alkyl, —C(=O)H, —C(=O)$C_1$-$C_6$alkoxy, —C(=O)$C_1$-$C_6$haloalkoxy, —C(=O)NH($C_1$-$C_6$alkyl), —C(=O)NH($C_1$-$C_6$haloalkyl) and —C(=O)N($C_1$-$C_6$alkyl)$_2$;
W is $NR^1$ or O;
Y is O or S;
J is a 5- or 6-membered heteroaryl or heterocyclyl, wherein said heteroaryl and heterocyclyl is unsubstituted or substituted with one to three substituents independently selected from $C_1$-$C_6$alkyl, $C_2$-$C_6$alkenyl, $C_2$-$C_6$alkynyl, —($C_0$-$C_6$alkyl)$C_{3-8}$cycloalkyl, $C_1$-$C_6$haloalkyl, $C_2$-$C_6$haloalkenyl, $C_2$-$C_6$haloalkynyl, —($C_{0-6}$alkyl)$C_{3-8}$halocycloalkyl, —$C_3$-$C_6$cycloalkyl-$C_1$-$C_3$haloalkyl, —($C_0$-$C_6$alkyl)heterocyclyl, halogen, CN, —$C_1$-$C_4$alkyl-CN, —$C_3$-$C_6$cycloalkyl-CN, $NO_2$, $C_1$-$C_6$alkoxy, $C_1$-$C_4$haloalkoxy, —($C_1$-$C_4$alkyl)($C_1$-$C_4$alkoxy), —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$ $C_1$-$C_6$haloalkyl, —S(=O)(=NH)$C_1$-$C_6$haloalkyl, —NH($C_1$-$C_6$alkyl), —N($C_2$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_2$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;
$Ar^1$ and $Ar^2$ are independently selected from phenyl and heteroaryl, wherein said phenyl and heteroaryl are unsubstituted or substituted by one to three substituents independently selected from $C_1$-$C_6$alkyl, $C_2$-$C_6$alkenyl, $C_2$-$C_6$alkynyl, ($C_0$-$C_6$alkyl)-$C_{3-6}$cycloalkyl, $C_1$-$C_6$haloalkyl, $C_2$-$C_6$haloalkenyl, $C_2$-$C_6$haloalkynyl, —($C_0$-$C_6$alkyl)$C_{3-6}$halocycloalkyl, —$C_3$-$C_6$cycloalkyl-$C_1$-$C_3$haloalkyl, —($C_0$-$C_6$alkyl)heterocyclyl, halogen, CN, —$C_1$-$C_6$alkyl-CN, —$C_3$-$C_6$cycloalkyl-CN, $NO_2$, $C_1$-$C_6$alkoxy, $C_1$-$C_6$haloalkoxy, —($C_1$-$C_4$alkyl)($C_1$-$C_4$alkoxy), —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$ $C_1$-$C_6$haloalkyl, —S(=O)(=NH)$C_1$-$C_6$haloalkyl, —NH($C_1$-$C_6$alkyl), —N($C_1$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_1$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;

$R^1$ and $R^2$ are independently selected from H, $C_1$-$C_6$-alkyl, $C_1$-$C_6$-haloalkyl, —($C_0$-$C_6$alkyl)$C_3$-$C_6$-cycloalkyl, —($C_0$-$C_6$alkyl)$C_{3-8}$halocycloalkyl, $C_2$-$C_6$-alkenyl, $C_2$-$C_6$haloalkenyl, $C_2$-$C_6$-alkynyl, $C_2$-$C_6$haloalkynyl, —($C_1$-$C_4$alkyl)O($C_1$-$C_4$alkyl), —S—$C_1$-$C_6$alkyl, —S—$C_1$-$C_6$haloalkyl, —S(=O)—$C_1$-$C_6$alkyl, —S(=O)$_2$—$C_1$-$C_6$alkyl, —S(=O)—$C_1$-$C_6$haloalkyl, —S(=O)$_2$—$C_1$-$C_6$haloalkyl, —C(=O)($C_1$-$C_6$alkyl), —C(=O)($C_1$-$C_6$alkoxy), —C(=O)NH($C_1$-$C_6$alkyl), —C(=O)N($C_1$-$C_6$alkyl)$_2$, —O—C(=O)($C_1$-$C_6$alkoxy), —O—C(=O)NH($C_1$-$C_6$alkyl), —O—C(=O)N($C_1$-$C_6$alkyl)$_2$ and —C(=N—$C_1$-$C_4$alkoxy)-$C_1$-$C_4$alkyl; provided that when $R^1$ and $R^2$ are different from H, $R^1$ and $R^2$ is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, halogen, CN, $NO_2$, $C_1$-$C_6$alkoxy, $C_1$-$C_6$haloalkoxy, —S—$C_1$-$C_6$alkyl, —S(=O)—$C_1$-$C_6$alkyl, —S(=O)$_2$$C_1$-$C_6$alkyl, —S(=O)(=NH)$C_1$-$C_6$alkyl, —NH($C_1$-$C_6$alkyl), —N($C_1$-$C_6$alkyl)$_2$, —NH($C_3$-$C_6$cycloalkyl), —N($C_1$-$C_4$alkyl)($C_3$-$C_6$cycloalkyl), —C(=O)($C_1$-$C_6$alkyl), —C(=O)($C_1$-$C_6$alkoxy, —C(=O)NH($C_1$-$C_6$alkyl) and —C(=O)($C_1$-$C_6$alkyl);

$R^3$ is selected from H, $C_1$-$C_6$-alkyl, —($C_{0-6}$alkyl)$C_3$-$C_6$-cycloalkyl, $C_2$-$C_6$-alkenyl, $C_2$-$C_6$-alkynyl, —C(=O)H, —C(=O)($C_1$-$C_6$-alkyl), —C(=O)O($C_1$-$C_6$-alkyl), —C(=O)($C_{0-6}$alkyl)($C_3$-$C_6$-cycloalkyl), —C(=O)O($C_{0-6}$alkyl)($C_3$-$C_6$-cycloalkyl)-C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), —($C_{0-6}$alkyl)phenyl, —($C_{0-6}$alkyl)-O-phenyl, —C(=O)—($C_0$-$C_6$-alkyl)(heteroaryl), —C(=O)—($C_0$-$C_6$-alkyl)(heterocyclyl), —($C_0$-$C_6$-alkyl)(heteroaryl), —($C_0$-$C_6$-alkyl)(heterocyclyl), —($C_0$-$C_6$-alkyl)-O-(heteroaryl), —($C_0$-$C_6$-alkyl)-O-(heterocyclyl), —($C_1$-$C_6$-alkyl)OC(=O)($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-haloalkyl), —($C_1$-$C_6$-alkyl)OC(=O)($C_1$-$C_6$-alkyl)-N($R^{3a}$)C(=O)—O—($C_{0-6}$alkyl)-phenyl, —($C_1$-$C_6$-alkyl)OC(=O)($C_1$-$C_6$-alkyl)-N($R^{3a}$)C(=O)—O—($C_{0-6}$alkyl)-heteroaryl, —($C_1$-$C_6$-alkyl)OC(=O)($C_1$-$C_6$-alkyl)-N($R^{3a}$)C(=O)—O—($C_{0-6}$alkyl)-heterocyclyl, —($C_1$-$C_6$-alkyl)-C(=O)N($R^{3a}$)—($C_1$-$C_6$-alkyl), —($C_1$-$C_6$-alkyl)-C(=O)N($R^{3a}$)—($C_0$-$C_6$-alkyl)-heterocyclyl-C(=O)—O—($C_1$-$C_6$-alkyl), —($C_1$-$C_6$-alkyl)-C(=O)N($R^{3a}$)—($C_0$-$C_6$-alkyl)-heterocyclyl-C(=O)—O—($C_1$-$C_6$-alkyl), —($C_1$-$C_6$-alkyl)-C(=O)N($R^{3a}$)—($C_0$-$C_6$-alkyl)-heteroaryl, —($C_1$-$C_6$-alkyl)-C(=O)N($R^{3a}$)—($C_0$-$C_6$-alkyl)-heterocyclyl, —($C_1$-$C_6$-alkyl)-C(=O)-heteroaryl, —($C_1$-$C_6$-alkyl)-C(=O)—($C_0$-$C_6$-alkyl)heterocyclyl, —($C_1$-$C_6$-alkyl)-C(=O)—N($R^{3a}$)($C_1$-$C_6$-alkyl)(N($R^{3a}$)($R^{3b}$))(C(=O)OH), —($C_1$-$C_6$-alkyl)-C(=O)—N($R^{3a}$)($C_1$-$C_6$-alkyl)(N($R^{3a}$)($R^{3b}$)), —($C_1$-$C_6$-alkyl)-C(=O)—N($R^{3a}$)($C_1$-$C_6$-alkyl)N($R^{3a}$)C(=O)—O—($C_1$-$C_6$-alkyl), —($C_1$-$C_6$-alkyl)-C(=O)—N($R^{3a}$)($C_1$-$C_6$-alkyl)N($R^{3a}$)C(=O)—O—($C_1$-$C_6$-alkyl)(C(=O)OH), —($C_1$-$C_6$-alkyl)-C(=O)—($C_0$-$C_6$-alkyl)heteroaryl-C(=O)—O—($C_1$-$C_6$-alkyl), —($C_1$-$C_6$-alkyl)-C(=O)—($C_0$-$C_6$-alkyl)-heterocyclyl-C(=O)—O—($C_1$-$C_6$-alkyl), —($C_1$-$C_6$-alkyl)-O—C(=O)—O—($C_1$-$C_6$-alkyl), —($C_1$-$C_6$-alkyl)-O—C(=O)($C_1$-$C_6$-alkyl), —($C_1$-$C_6$-alkyl)-O—C(=O)($C_3$-$C_6$-cycloalkyl), —($C_1$-$C_6$-alkyl)-O—C(=O)—($C_0$-$C_6$-alkyl)heteroaryl, —($C_1$-$C_6$-alkyl)-O—C(=O)($C_0$-$C_6$-alkyl)heterocyclyl, —($C_1$-$C_6$-alkyl)-O—C(=O)—($C_1$-$C_6$-alkyl)-N($R^{3a}$)C(=O)—O—($C_1$-$C_6$-alkyl), —($C_0$-$C_6$-alkyl)-N$R^{3a}R^{3b}$, —($C_1$-$C_6$-alkyl)-O—($C_0$-$C_6$-alkyl)heteroaryl and —($C_1$-$C_6$-alkyl)-O—($C_0$-$C_6$-alkyl)heterocyclyl;

wherein each alkyl, cycloalkyl, alkenyl, alkynyl, phenyl, heteroaryl and heterocyclyl are unsubstituted or substituted with one or more substituents independently selected from halogen, CN, $NO_2$, $NR^{3a}R^{3b}$, $C_1$-$C_6$-alkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-alkyl), —O—S(=O)$_2$($C_1$-$C_6$-alkyl), —O—S(=O)$_2$($C_1$-$C_6$-haloalkyl), —C(=O)H, —C(=O)OH, —C(=O)NR$^{3a}R^{3b}$, —($C_1$-$C_6$-alkyl)NR$^{3a}R^{3b}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —C(=O)($C_1$-$C_6$-alkyl)C(=O)O($C_1$-$C_6$-alkyl), phenyl, —O-phenyl, —Si($C_1$-$C_6$-alkyl)$_3$, —S(=O)NR$^{3a}R^{3b}$, —S(=O)$_2$NR$^{3a}R^{3b}$, heteroaryl and heterocyclyl;

Z is a 4- to 7-membered heterocyclyl or heteroaryl, which heterocyclyl or heteroaryl is unsubstituted or substituted with one or two substituents independently selected from halogen, CN, $NO_2$, oxo, hydroxy, —NR$^{Za}R^{Zb}$, $C_1$-$C_6$-alkyl, $C_1$-$C_6$-haloalkyl, $C_3$-$C_6$cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-haloalkyl), —OS(=O)$_2$($C_1$-$C_6$-alkyl), —OS(=O)$_2$($C_1$-$C_6$-haloalkyl), —C(=O)H, —C(=O)OH, —C(=O)NR$^{Za}R^{Zb}$, —($C_1$-$C_6$-alkyl)NR$^{Za}R^{Zb}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), phenyl, —O-phenyl, —Si($C_1$-$C_6$-alkyl)$_3$, —S(=O)NR$^{Za}R^{Zb}$, —S(O)$_2$NR$^{Za}R^{Zb}$, heteroaryl and heterocyclyl;

wherein each alkyl, cycloalkyl, alkenyl, alkynyl, phenyl, heteroaryl and heterocyclyl substituent is unsubstituted or substituted with one or more substituents independently selected from halogen, CN, $NO_2$, NR$^{Za}R^{Zb}$, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-alkyl), —O—S(=O)$_2$($C_1$-$C_6$-alkyl), —O—S(=O)$_2$($C_1$-$C_6$-haloalkyl), —C(=O)H, —C(=O)OH, —C(=O)NR$^{Za}R^{Zb}$, —($C_1$-$C_6$-alkyl)NR$^{Za}R^{Zb}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$- alkyl), phenyl, —O-phenyl, —Si(C$_1$-C$_6$-alkyl)$_3$, —S(=O)NR$^{Za}$R$^{Zb}$, —S(=O)$_2$NR$^{Za}$R$^{Zb}$, heteroaryl and heterocyclyl; R$^{3a}$, R$^{3b}$, R$^{Za}$ and R$^{Zb}$ are independently selected from H, C$_1$-C$_6$-alkyl, C$_1$-C$_6$-haloalkyl, C$_3$-C$_6$-cycloalkyl and C$_1$-C$_6$-alkoxy;

or an agrochemically acceptable salt, stereoisomer, tautomer, N-oxide thereof.

Definitions

The term 'halogen' as used herein refers to a fluoro, chloro, bromo or iodo.

As used herein, the term "C$_3$-C$_6$alkyl" refers to a straight or branched hydrocarbon chain radical consisting solely of carbon and hydrogen atoms, containing no unsaturation, having from one to six carbon atoms, and which is attached to the rest of the molecule by a single bond. The term "C$_{1-4}$alkyl" is to be construed accordingly. Examples of C$_{1-6}$alkyl include, but are not limited to, methyl, (R)-methyl, ethyl, n-propyl, 1-methylethyl (iso-propyl), n-butyl, n-pentyl and 1,1-dimethylethyl (t-butyl).

As used herein, the term "C$_3$-C$_6$haloalkyl" refers to a C$_3$-C$_6$alkyl radical, as defined above, substituted with one or more of the same or different halogen atoms, as defined above. Examples of C$_3$-C$_6$haloalkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

As used herein, the term "C$_3$-C$_6$-cycloalkyl" refers to a saturated monocyclic hydrocarbon ring of 3 to 6 carbon atoms. Examples of such groups include cyclopropyl, cyclobutyl, cyclopentyl and cyclohexyl. If a different number of carbon atoms is specified, then the definition is to be amended accordingly.

As used herein, the term "C$_3$-C$_6$halocycloalkyl" refers to a C$_3$-C$_6$cycloalkyl radical, as defined above, substituted with one or more of the same or different halogen atoms, as defined above. Examples of C$_3$-C$_6$halocycloalkyl include, but are not limited to trifluorocyclopropyl, difluorobutyl, fluorocyclo and trichlorocyclohexyl.

As used herein, the term "C$_2$-C$_6$alkenyl" refers to a straight or branched hydrocarbon chain radical group consisting solely of carbon and hydrogen atoms, containing at least one double bond, having from two to six carbon atoms, which is attached to the rest of the molecule by a single bond. The term "C$_2$-C$_4$alkenyl" is to be construed accordingly. Examples of C$_2$-C$_6$alkenyl include, but are not limited to, ethenyl, prop-1-enyl, but-1-enyl, pent-1-enyl, pent-4-enyl and penta-1,4-dienyl.

As used herein, the term 'C$_2$-C$_6$haloalkenyl' as used herein refers to a C$_2$-C$_6$ alkenyl radical, as defined herein, substituted with one or more of the same or different halogen atoms, e.g for example, 2,2-difluorovinyl or 1,2-dichloro-2-fluoro-vinyl.

As used herein, the term "C$_2$-C$_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "C$_2$-C$_6$alkynyl" is to be construed accordingly. Examples of C$_2$-C$_6$alkynyl include, but are not limited to, ethynyl, prop-1-ynyl, but-1-ynyl, pent-1-ynyl, pent-4-ynyl and penta-1,4-diynyl.

As used herein, the term 'C$_2$-C$_6$haloalkynyl' as used herein refers to a C$_2$-C$_6$alkynyl radical, as defined herein, substituted with one or more of the same or different halogen atoms, for example 1-chloroprop-2-ynyl.

As used herein, the term "C$_1$-C$_6$alkoxyC$_1$-C$_6$alkyl" as used herein refers to an —C$_1$-C$_6$alkyl-O—C$_1$-C$_6$alkyl is as defined above. Examples of such groups include methoxyethyl, methoxypropyl, ethoxypropyl.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heterocyclyl" or "heterocyclic" refers to a stable 5- or 6-membered non-aromatic monocyclic ring radical which comprises 1, 2, or 3, heteroatoms individually selected from nitrogen, oxygen and sulfur. The heterocyclyl radical may be bonded via a carbon atom or heteroatom. Examples of heterocyclyl include, but are not limited to, azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl.

The presence of one or more C=N double bonds in a compound of formula (I) means that the compounds may occur in E or Z isomeric forms. Formula (I) is intended to include all those possible stereoisomeric forms and mixtures thereof.

The presence of one or more possible asymmetric carbon atoms in a compound of formula (I) means that the compounds may occur in optically stereoisomeric forms, i.e. enantiomeric or diastereomeric forms. Also atropisomers may occur as a result of restricted rotation about a single bond. Formula (I) is intended to include all those possible stereoisomeric forms and mixtures thereof. The present invention includes all those possible stereoisomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as a N-oxide or in salt form, e.g. an agronomically usable salt form.

Embodiment 2

A Compound According to Embodiment 1, of Formula (I)

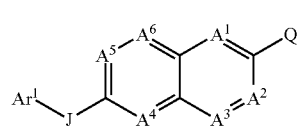

(I)

wherein Q is selected from

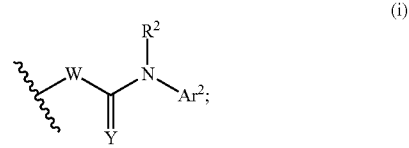

(i)

-continued (ii)

[Structure showing N-R², N-Ar², S-R³ guanidine-type group]

(iii)

[Structure showing N-R¹, N-Ar², S-R³ guanidine-type group]

(iv)

[Structure showing N, N-Ar², S with Z ring]

(v)

[Structure showing N, N-Ar², S with Z ring]

$A^1$ is N or $CR^{41}$;
$A^2$ is N or $CR^{42}$;
$A^3$ is N or $CR^{43}$;
$A^4$ is N or $CR^{44}$;
$A^5$ is N or $CR^{45}$;
$A^6$ is N or $CR^{46}$;
with the proviso that not more than four of $A^1$, $A^2$, $A^3$, $A^4$, $A^5$ and $A^6$ are N;
$R^{41}$, $R^{42}$, $R^{43}$, $R^{44}$, $R^{45}$ and $R^{46}$ are independently selected from H, $C_1$-$C_6$alkyl, $C_2$-$C_6$alkenyl, $C_2$-$C_6$alkynyl, —($C_0$-$C_6$alkyl)($C_{3-6}$cycloalkyl), $C_1$-$C_6$haloalkyl, $C_2$-$C_6$haloalkenyl, $C_2$-$C_6$haloalkynyl, —($C_0$-$C_6$alkyl)($C_3$-$C_6$halocycloalkyl), —($C_3$-$C_6$cycloalkyl)($C_1$-$C_3$haloalkyl), —($C_{0-6}$alkyl)-heterocyclyl, —($C_0$-$C_6$alkyl)-heteroaryl, halogen, CN, —$C_1$-$C_4$alkyl-CN, —$C_3$-$C_6$cycloalkyl-CN, $NO_2$, $C_1$-$C_6$alkoxy, $C_1$-$C_4$haloalkoxy, $C_1$-$C_4$alkoxy-$C_1$-$C_4$alkyl, —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —NH—$C_1$-$C_6$alkyl, —N($C_1$-$C_6$alkyl)$_2$, —NH—$C_3$-$C_6$cycloalkyl, —N($C_1$-$C_6$alkyl)($C_3$-$C_6$cycloalkyl), —C(=O)$C_1$-$C_6$alkyl, —C(=O)H, —C(=O)$C_1$-$C_6$alkoxy, —C(=O)$C_1$-$C_6$haloalkoxy, —C(=O)NH($C_1$-$C_6$alkyl), —C(=O)NH($C_1$-$C_6$haloalkyl) and —C(=O)N($C_1$-$C_6$ alkyl)$_2$;
W is $NR^1$ or O;
Y is O or S;
J is a 5- or 6-membered heteroaryl or heterocyclyl, wherein said heteroaryl and heterocyclyl is unsubstituted or substituted with one to three substituents independently selected from $C_1$-$C_6$alkyl, $C_2$-$C_6$alkenyl, $C_2$-$C_6$alkynyl, —($C_0$-$C_6$alkyl)$C_{3-8}$cycloalkyl, $C_1$-$C_6$haloalkyl, $C_2$-$C_6$haloalkenyl, $C_2$-$C_6$haloalkynyl, —($C_{0-6}$alkyl)$C_{3-8}$halocycloalkyl, —$C_3$-$C_6$cycloalkyl-$C_1$-$C_3$haloalkyl, —($C_0$-$C_6$alkyl)heterocyclyl, halogen, CN, —$C_1$-$C_4$alkyl-CN, —$C_3$-$C_6$cycloalkyl-CN, $NO_2$, $C_1$-$C_6$alkoxy, $C_1$-$C_4$haloalkoxy, —($C_1$-$C_4$alkyl)($C_1$-$C_4$alkoxy), —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$ $C_1$-$C_6$haloalkyl, —S(=O)(=NH)$C_1$-$C_6$haloalkyl, —NH($C_1$-$C_6$alkyl), —N($C_2$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_2$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;
$Ar^1$ and $Ar^2$ are independently selected from phenyl, thienyl, pyridyl, pyrimidinyl, pyrazinyl, pyridazinyl, furanyl, pyrazolyl, thiazolyl, imidazolyl, oxazolyl and isoxazolyl, wherein said phenyl, thienyl, pyridyl, pyrimidinyl, pyrazinyl, pyridazinyl, furanyl, pyrazolyl, thiazolyl, imidazolyl, oxazolyl and isoxazolyl are unsubstituted or substituted by one to three substituents independently selected from $C_1$-$C_6$alkyl, $C_2$-$C_6$alkenyl, $C_2$-$C_6$alkynyl, ($C_0$-$C_6$alkyl)-$C_3$-$C_6$cycloalkyl, $C_1$-$C_6$haloalkyl, $C_2$-$C_6$haloalkenyl, $C_2$-$C_6$haloalkynyl, —($C_0$-$C_6$alkyl)$C_3$-$C_6$halocycloalkyl, —$C_3$-$C_6$cycloalkyl-$C_1$-$C_3$haloalkyl, —($C_0$-$C_6$alkyl)heterocyclyl, halogen, CN, —$C_1$-$C_6$alkyl-CN, —$C_3$-$C_6$cycloalkyl-CN, $NO_2$, $C_1$-$C_6$alkoxy, $C_1$-$C_6$haloalkoxy, —($C_1$-$C_4$alkyl)($C_1$-$C_4$alkoxy), —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$ $C_1$-$C_6$haloalkyl, —S(=O)(=NH)$C_1$-$C_6$haloalkyl, —NH($C_1$-$C_6$alkyl), —N($C_1$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_1$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;
$R^1$ and $R^2$ are independently selected from H, $C_1$-$C_6$-alkyl, $C_1$-$C_6$-haloalkyl, —($C_0$-$C_6$alkyl)$C_3$-$C_6$-cycloalkyl, —($C_0$-$C_6$alkyl)$C_{3-8}$halocycloalkyl, $C_2$-$C_6$-alkenyl, $C_2$-$C_6$haloalkenyl, $C_2$-$C_6$-alkynyl, $C_2$-$C_6$haloalkynyl, —($C_1$-$C_4$alkyl)O($C_1$-$C_4$alkyl), —S—$C_1$-$C_6$alkyl, —S—$C_1$-$C_6$haloalkyl, —S(=O)—$C_1$-$C_6$alkyl, —S(=O)$_2$—$C_1$-$C_6$alkyl, —S(=O)—$C_1$-$C_6$haloalkyl, —S(=O)$_2$—$C_1$-$C_6$haloalkyl, —C(=O)($C_1$-$C_6$alkyl), —C(=O)($C_1$-$C_6$alkoxy), —C(=O)NH($C_1$-$C_6$alkyl), —C(=O)N($C_1$-$C_6$alkyl)$_2$, —O—C(=O)($C_1$-$C_6$alkoxy), —O—C(=O)NH($C_1$-$C_6$alkyl), —O—C(=O)N($C_1$-$C_6$alkyl)$_2$ and —C(=N—$C_1$-$C_4$alkoxy)-$C_1$-$C_4$alkyl; provided that when $R^1$ and $R^2$ are different from H, $R^1$ and $R^2$ is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, halogen, CN, $NO_2$, $C_1$-$C_6$alkoxy, $C_1$-$C_6$haloalkoxy, —S—$C_1$-$C_6$alkyl, —S(=O)—$C_1$-$C_6$alkyl, —S(=O)$_2$$C_1$-$C_6$alkyl, —S(=O)(=NH)$C_1$-$C_6$alkyl, —NH($C_1$-$C_6$alkyl), —N($C_1$-$C_6$alkyl)$_2$, —NH($C_3$-$C_6$cycloalkyl), —N($C_1$-$C_4$alkyl)($C_3$-$C_6$cycloalkyl), —C(=O)($C_1$-$C_6$alkyl), —C(=O)($C_1$-$C_6$alkoxy, —C(=O)NH($C_1$-$C_6$alkyl) and —C(=O)($C_1$-$C_6$alkyl);
$R^3$ is selected from H, $C_1$-$C_6$-alkyl, —($C_{0-6}$alkyl)$C_3$-$C_6$-cycloalkyl, $C_2$-$C_6$-alkenyl, $C_2$-$C_6$-alkynyl, —C(=O)H, —C(=O)($C_1$-$C_6$-alkyl), —C(=O)O($C_1$-$C_6$-alkyl), —C(=O)($C_{0-6}$alkyl)($C_3$-$C_6$-cycloalkyl), —C(=O)O($C_{0-6}$alkyl)($C_3$-$C_6$-cycloalkyl)-C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), —($C_{0-6}$alkyl)phenyl, —($C_{0-6}$alkyl)-O-phenyl, —C(=O)—($C_0$-$C_6$-alkyl)(heteroaryl), —C(=O)—($C_0$-$C_6$-alkyl)(heterocyclyl), —($C_0$-$C_6$-alkyl)(heteroaryl), —($C_0$-$C_6$-alkyl)(heterocyclyl), —($C_0$-$C_6$-alkyl)-O-(heteroaryl), —($C_0$-$C_6$-alkyl)-O-(heterocyclyl), —($C_1$-$C_6$-alkyl)OC(=O)($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-alkyl)-

—O—(C$_1$-C$_6$-alkyl), —(C$_1$-C$_6$-alkyl)OC(=O)(C$_1$-C$_6$-alkyl)-O—(C$_1$-C$_6$-haloalkyl), —(C$_1$-C$_6$-alkyl)OC(=O)(C$_1$-C$_6$-alkyl)-N(R$^{3a}$)C(=O)—O—(C$_{0-6}$alkyl)-phenyl, —(C$_1$-C$_6$-alkyl)OC(=O)(C$_1$-C$_6$-alkyl)-N(R$^{3a}$)C(=O)—O—(C$_{0-6}$alkyl)-heteroaryl, —(C$_1$-C$_6$-alkyl)OC(=O)(C$_1$-C$_6$-alkyl)-N(R$^{3a}$)C(=O)—O—(C$_{0-6}$alkyl)-heterocyclyl, —(C$_1$-C$_6$-alkyl)-C(=O)N(R$^{3a}$)—(C$_1$-C$_6$-alkyl), —(C$_1$-C$_6$-alkyl)-C(=O)N(R$^{3a}$)—(C$_0$-C$_6$-alkyl)-heteroaryl-C(=O)—O—(C$_1$-C$_6$-alkyl), —(C$_1$-C$_6$-alkyl)-C(=O)N(R$^{3a}$)—(C$_0$-C$_6$-alkyl)-heterocyclyl-C(=O)—O—(C$_1$-C$_6$-alkyl), —(C$_1$-C$_6$-alkyl)-C(=O)N(R$^{3a}$)—(C$_0$-C$_6$-alkyl)-heteroaryl, —(C$_1$-C$_6$-alkyl)-C(=O)N(R$^{3a}$)—(C$_0$-C$_6$-alkyl)-heterocyclyl, —(C$_1$-C$_6$-alkyl)-C(=O)-heteroaryl, —(C$_1$-C$_6$-alkyl)-C(=O)—(C$_0$-C$_6$-alkyl)heterocyclyl, —(C$_1$-C$_6$-alkyl)-C(=O)—N(R$^{3a}$)(C$_1$-C$_6$-alkyl)(N(R$^{3a}$)(R$^{3b}$))(C(=O)OH), —(C$_1$-C$_6$-alkyl)-C(=O)—N(R$^{3a}$)(C$_1$-C$_6$-alkyl)(N(R$^{3a}$)(R$^{3b}$)), —(C$_1$-C$_6$-alkyl)-C(=O)—N(R$^{3a}$)(C$_1$-C$_6$-alkyl)N(R$^{3a}$)C(=O)—O—(C$_1$-C$_6$-alkyl), —(C$_1$-C$_6$-alkyl)-C(=O)—N(R$^{3a}$)(C$_1$-C$_6$-alkyl)N(R$^{3a}$)C(=O)—O—(C$_1$-C$_6$-alkyl)(C(=O)OH), —(C$_1$-C$_6$-alkyl)-C(=O)—(C$_0$-C$_6$-alkyl)heteroaryl-C(=O)—O—(C$_1$-C$_6$-alkyl), —(C$_1$-C$_6$-alkyl)-C(=O)—(C$_0$-C$_6$-alkyl)-heterocyclyl-C(=O)—O—(C$_1$-C$_6$-alkyl), —(C$_1$-C$_6$-alkyl)-O—C(=O)—O—(C$_1$-C$_6$-alkyl), —(C$_1$-C$_6$-alkyl)-O—C(=O)(C$_1$-C$_6$-alkyl), —(C$_1$-C$_6$-alkyl)-O—C(=O)(C$_3$-C$_6$-cycloalkyl), —(C$_1$-C$_6$-alkyl)-O—C(=O)—(C$_0$-C$_6$-alkyl)heteroaryl, —(C$_1$-C$_6$-alkyl)-O—C(=O)(C$_0$-C$_6$-alkyl)heterocyclyl, —(C$_1$-C$_6$-alkyl)-O—C(=O)—(C$_1$-C$_6$-alkyl)-N(R$^{3a}$)C(=O)—O—(C$_1$-C$_6$-alkyl), —(C$_0$-C$_6$-alkyl)-NR$^{3a}$R$^{3b}$, —(C$_1$-C$_6$-alkyl)-O—(C$_0$-C$_6$-alkyl) heteroaryl and —(C$_1$-C$_6$-alkyl)-O—(C$_0$-C$_6$-alkyl) heterocyclyl;

wherein each alkyl, cycloalkyl, alkenyl, alkynyl, phenyl, heteroaryl and heterocyclyl are unsubstituted or substituted with one or more substituents independently selected from halogen, CN, NO$_2$, NR$^{3a}$R$^{3b}$, C$_1$-C$_6$-alkyl, C$_1$-C$_6$-haloalkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_2$-C$_6$-alkynyl, —S(=O)(C$_1$-C$_6$-alkyl), —S(=O)$_2$(C$_1$-C$_6$-alkyl), —O—S(=O)$_2$(C$_1$-C$_6$-alkyl), —O—S(=O)$_2$(C$_1$-C$_6$-haloalkyl), —C(=O)H, —C(=O)OH, —C(=O)NR$^{3a}$R$^{3b}$, —(C$_1$-C$_6$-alkyl)NR$^{3a}$R$^{3b}$, —C(=O)(C$_1$-C$_6$-alkyl), —C(=O)O(C$_1$-C$_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{3a}$R$^{3b}$, —S(O)$_2$NR$^{3a}$R$^{3b}$, heteroaryl and heterocyclyl;

Z is a 4- to 7-membered heterocyclyl or heteroaryl, which heterocyclyl or heteroaryl is unsubstituted or substituted with one or two substituents independently selected from halogen, CN, NO$_2$, oxo, hydroxy, —NR$^{Za}$R$^{Zb}$, C$_1$-C$_6$-alkyl, C$_1$-C$_6$-haloalkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_2$-C$_6$-alkynyl, —S—(C$_1$-C$_6$-alkyl), —S(=O)(C$_1$-C$_6$-alkyl), —S(=O)$_2$(C$_1$-C$_6$-haloalkyl), —OS(=O)$_2$(C$_1$-C$_6$-alkyl), —OS(=O)$_2$(C$_1$-C$_6$-haloalkyl), —C(=O)H, —C(=O)OH, —C(=O)NR$^{Za}$R$^{Zb}$, —(C$_1$-C$_6$-alkyl)NR$^{Za}$R$^{Zb}$, —C(=O)(C$_1$-C$_6$-alkyl), —C(=O)O(C$_1$-C$_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{Za}$R$^{Zb}$, —S(O)$_2$NR$^{Za}$R$^{Zb}$, heteroaryl and heterocyclyl;

wherein each alkyl, cycloalkyl, alkenyl, alkynyl, phenyl, heteroaryl and heterocyclyl substituent is unsubstituted or substituted with one or more substituents independently selected from halogen, CN, NO$_2$, NR$^{Za}$R$^{Zb}$, C$_1$-C$_6$-alkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_2$-C$_6$-alkynyl, —S(=O)(C$_1$-C$_6$-alkyl), —S(=O)$_2$(C$_1$-C$_6$-alkyl), —O—S(=O)$_2$(C$_1$-C$_6$-alkyl), —O—S(=O)$_2$(C$_1$-C$_6$-haloalkyl), —C(=O)H, —C(=O)OH, —C(=O)NR$^{Za}$R$^{Zb}$, —(C$_1$-C$_6$-alkyl) NR$^{Za}$R$^{Zb}$, —C(=O)(C$_1$-C$_6$-alkyl), —C(=O)O(C$_1$-C$_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{Za}$R$^{Zb}$, —S(=O)$_2$NR$^{Za}$R$^{Zb}$, heteroaryl and heterocyclyl;

R$^{3a}$, R$^{3b}$, R$^{Za}$ and R$^{Zb}$ are independently selected from H, C$_1$-C$_6$-alkyl, C$_1$-C$_6$-haloalkyl, C$_3$-C$_6$-cycloalkyl and C$_1$-C$_6$-alkoxy;

or an agrochemically acceptable salt, stereoisomer, tautomer, N-oxide thereof.

Embodiment 2.1

A Compound According to Embodiment 1, of Formula (I')

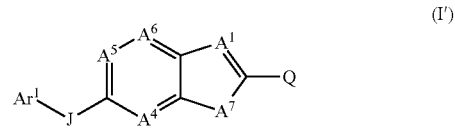

wherein Q is selected from

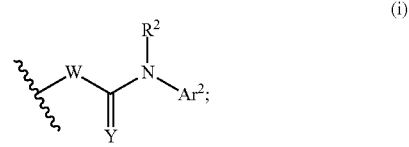

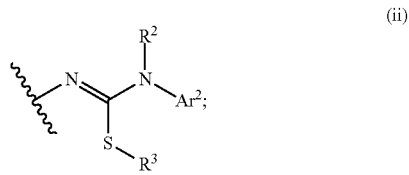

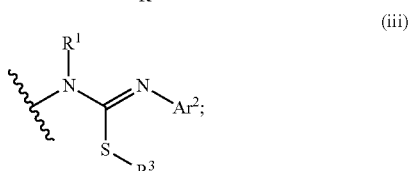

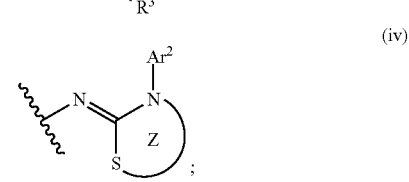

-continued (v)

[Structure: N-Z ring with N-Ar² and =S substituents]

$A^1$ is N or $CR^{A1}$;
$A^2$ is N or $CR^{A2}$;
$A^3$ is N or $CR^{A3}$;
$A^4$ is N or $CR^{A4}$;
$A^5$ is N or $CR^{A5}$;
$A^6$ is N or $CR^{A6}$;
with the proviso that not more than four of $A^1$, $A^2$, $A^3$, $A^4$, $A^5$ and $A^6$ are N;
$R^{A1}$, $R^{A2}$, $R^{A3}$, $R^{A4}$, $R^{A5}$ and $R^{A6}$ are independently selected from H, $C_1$-$C_6$alkyl, $C_2$-$C_6$alkenyl, $C_2$-$C_6$alkynyl, —($C_0$-$C_6$alkyl)($C_3$-$C_6$cycloalkyl), $C_1$-$C_6$haloalkyl, $C_2$-$C_6$haloalkenyl, $C_2$-$C_6$haloalkynyl, —($C_{0-6}$alkyl)($C_3$-$C_6$halocycloalkyl), —($C_3$-$C_6$cycloalkyl)($C_1$-$C_3$haloalkyl), —($C_{0-6}$alkyl)-heterocyclyl, —($C_0$-$C_6$alkyl)-heteroaryl, halogen, CN, —$C_1$-$C_4$alkyl-CN, —$C_3$-$C_6$cycloalkyl-CN, $NO_2$, $C_1$-$C_6$alkoxy, $C_1$-$C_4$haloalkoxy, $C_1$-$C_4$alkoxy-$C_1$-$C_4$alkyl, —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —NH—$C_1$-$C_6$alkyl, —N($C_1$-$C_6$alkyl)$_2$, —NH—$C_3$-$C_6$cycloalkyl, —N($C_1$-$C_6$alkyl)($C_3$-$C_6$cycloalkyl), —C(=O)$C_1$-$C_6$alkyl, —C(=O)H, —C(=O)$C_1$-$C_6$alkoxy, —C(=O)$C_1$-$C_6$haloalkoxy, —C(=O)NH($C_1$-$C_6$alkyl), —C(=O)NH($C_1$-$C_6$haloalkyl) and —C(=O)N($C_1$-$C_6$alkyl)$_2$;
W is $NR^1$ or O;
Y is O or S;
J is a 5- or 6-membered heteroaryl or heterocyclyl, wherein said heteroaryl and heterocyclyl is unsubstituted or substituted with one to three substituents independently selected from $C_1$-$C_6$alkyl, $C_2$-$C_6$alkenyl, $C_2$-$C_6$alkynyl, —($C_0$-$C_6$alkyl)$C_{3-8}$cycloalkyl, $C_1$-$C_6$haloalkyl, $C_2$-$C_6$haloalkenyl, $C_2$-$C_6$haloalkynyl, —($C_{0-6}$alkyl)$C_{3-8}$halocycloalkyl, —$C_3$-$C_6$cycloalkyl-$C_1$-$C_3$haloalkyl, —($C_0$-$C_6$alkyl)heterocyclyl, halogen, CN, —$C_1$-$C_4$alkyl-CN, —$C_3$-$C_6$cycloalkyl-CN, $NO_2$, $C_1$-$C_6$alkoxy, $C_1$-$C_4$haloalkoxy, —($C_1$-$C_4$alkyl)($C_1$-$C_4$alkoxy), —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$ $C_1$-$C_6$haloalkyl, —S(=O)(=NH)$C_1$-$C_6$haloalkyl, —NH($C_1$-$C_6$alkyl), —N($C_2$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_2$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;
$Ar^1$ and $Ar^2$ are independently selected from phenyl, thienyl, pyridyl, pyrimidinyl, pyrazinyl, pyridazinyl, furanyl, pyrazolyl, thiazolyl, imidazolyl, oxazolyl and isoxazolyl, wherein said phenyl, thienyl, pyridyl, pyrimidinyl, pyrazinyl, pyridazinyl, furanyl, pyrazolyl, thiazolyl, imidazolyl, oxazolyl and isoxazolyl are unsubstituted or substituted by one to three substituents independently selected from $C_1$-$C_6$alkyl, $C_2$-$C_6$alkenyl, $C_2$-$C_6$alkynyl, ($C_0$-$C_6$alkyl)-$C_3$-$C_6$cycloalkyl, $C_1$-$C_6$haloalkyl, $C_2$-$C_6$haloalkenyl, $C_2$-$C_6$haloalkynyl, —($C_0$-$C_6$alkyl)$C_3$-$C_6$halocycloalkyl, —$C_3$-$C_6$cycloalkyl-$C_1$-$C_3$haloalkyl, —$C_0$-$C_6$alkylheterocyclyl, halogen, CN, —$C_1$-$C_4$alkyl-CN, —$C_3$-$C_6$cycloalkyl-CN, $NO_2$, $C_1$-$C_6$alkoxy, $C_1$-$C_6$haloalkoxy, —($C_1$-$C_4$alkyl) ($C_1$-$C_4$alkoxy), —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$ $C_1$-$C_6$haloalkyl, —S(=O)(=NH)$C_1$-$C_6$haloalkyl, —NH($C_1$-$C_6$alkyl), —N($C_1$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_1$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;
$R^1$ and $R^2$ are independently selected from H, $C_1$-$C_6$-alkyl, $C_1$-$C_6$-haloalkyl, —($C_0$-$C_6$alkyl)$C_3$-$C_6$-cycloalkyl, —($C_0$-$C_6$alkyl)$C_{3-8}$halocycloalkyl, $C_2$-$C_6$-alkenyl, $C_2$-$C_6$haloalkenyl, $C_2$-$C_6$-alkynyl, $C_2$-$C_6$haloalkynyl, —($C_1$-$C_4$alkyl)O($C_1$-$C_4$alkyl), —S—$C_1$-$C_6$alkyl, —S—$C_1$-$C_6$haloalkyl, —S(=O)—$C_1$-$C_6$alkyl, —S(=O)$_2$—$C_1$-$C_6$alkyl, —S(=O)—$C_1$-$C_6$haloalkyl, —S(=O)$_2$—$C_1$-$C_6$haloalkyl, —C(=O)($C_1$-$C_6$alkyl), —C(=O)($C_1$-$C_6$alkoxy), —C(=O)NH($C_1$-$C_6$alkyl), —C(=O)N($C_1$-$C_6$alkyl)$_2$, —O—C(=O)($C_1$-$C_6$alkoxy), —O—C(=O)NH($C_1$-$C_6$alkyl), —O—C(=O)N($C_1$-$C_6$alkyl)$_2$ and —C(=N—$C_1$-$C_4$alkoxy)-$C_1$-$C_4$alkyl; provided that when $R^1$ and $R^2$ are different from H, $R^1$ and $R^2$ is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, halogen, CN, $NO_2$, $C_1$-$C_6$alkoxy, $C_1$-$C_6$haloalkoxy, —S—$C_1$-$C_6$alkyl, —S(=O)—$C_1$-$C_6$alkyl, —S(=O)$_2$$C_1$-$C_6$alkyl, —S(=O)(=NH)$C_1$-$C_6$alkyl, —NH($C_1$-$C_6$alkyl), —N($C_1$-$C_6$alkyl)$_2$, —NH($C_3$-$C_6$cycloalkyl), —N($C_1$-$C_4$alkyl)($C_3$-$C_6$cycloalkyl), —C(=O)($C_1$-$C_6$alkyl), —C(=O)($C_1$-$C_6$alkoxy), —C(=O)NH($C_1$-$C_6$alkyl) and —C(=O)($C_1$-$C_6$alkyl);
$R^3$ is selected from H, $C_1$-$C_6$-alkyl, —($C_{0-6}$alkyl)$C_3$-$C_6$-cycloalkyl, $C_2$-$C_6$-alkenyl, $C_2$-$C_6$-alkynyl, —C(=O)H, —C(=O)($C_1$-$C_6$-alkyl), —C(=O)O($C_1$-$C_6$-alkyl), —C(=O)($C_{0-6}$alkyl)($C_3$-$C_6$-cycloalkyl), —C(=O)O($C_{0-6}$alkyl)($C_3$-$C_6$-cycloalkyl)-C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), —($C_{0-6}$alkyl)phenyl, —($C_{0-6}$alkyl)-O-phenyl, —C(=O)—($C_0$-$C_6$-alkyl)(heteroaryl), —C(=O)—($C_0$-$C_6$-alkyl)(heterocyclyl), —($C_0$-$C_6$-alkyl)(heteroaryl), —($C_0$-$C_6$-alkyl)(heterocyclyl), —($C_0$-$C_6$-alkyl)-O-(heteroaryl), —($C_0$-$C_6$-alkyl)-O-(heterocyclyl), —($C_1$-$C_6$-alkyl)OC(=O)($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-haloalkyl), —($C_1$-$C_6$-alkyl)OC(=O) ($C_1$-$C_6$-alkyl)-N($R^{3a}$)C(=O)—O—($C_{0-6}$alkyl)-phenyl, —($C_1$-$C_6$-alkyl)OC(=O)($C_1$-$C_6$-alkyl)-N($R^{3a}$)C(=O)—O—($C_{0-6}$ alkyl)-heteroaryl, —($C_1$-$C_6$-alkyl)OC(=O)($C_1$-$C_6$-alkyl)-N($R^{3a}$)C(=O)—O—($C_{0-6}$alkyl)-heterocyclyl, —($C_1$-$C_6$-alkyl)-C(=O)N($R^{3a}$)—($C_1$-$C_6$-alkyl), —($C_1$-$C_6$-alkyl)-C(=O)N($R^{3a}$)—($C_0$-$C_6$-alkyl)-heteroaryl-C(=O)—O—($C_1$-$C_6$-alkyl), —($C_1$-$C_6$-alkyl)-C(=O)N($R^{3a}$)—($C_0$-$C_6$-alkyl)-heterocyclyl-C(=O)—O—($C_1$-$C_6$-alkyl), —($C_1$-$C_6$-alkyl)-C(=O)N($R^{3a}$)—($C_0$-$C_6$-alkyl)-heteroaryl, —($C_1$-$C_6$-alkyl)-C(=O)N($R^{3a}$)—($C_0$-$C_6$-alkyl)-heterocyclyl, alkyl)-C(=O)-heteroaryl, —($C_1$-$C_6$-alkyl)-C(=O)—($C_0$-$C_6$-alkyl)heterocyclyl, —($C_1$-$C_6$-alkyl)-C(=O)—N($R^{3a}$)($C_1$-$C_6$-alkyl)(N($R^{3a}$)($R^{3b}$))(C(=O)OH), —($C_1$-$C_6$-alkyl)-C(=O)—N($R^{3a}$)($C_1$-$C_6$-alkyl)(N($R^{3a}$)($R^{3b}$)), —($C_1$-$C_6$-alkyl)-C(=O)—N($R^{3a}$)($C_1$-$C_6$-alkyl)N($R^{3a}$)C(=O)—O—($C_1$-$C_6$-alkyl), —($C_1$-$C_6$-alkyl)-C(=O)—N($R^{3a}$)($C_1$-$C_6$-alkyl)N($R^{3a}$)C(=O)—O—($C_1$-$C_6$-alkyl)(C(=O)OH), —(C$_1$-C$_6$-alkyl)-C(=O)—(C$_0$-C$_6$-alkyl)heteroaryl-C(=O)—O—(C$_1$-C$_6$-alkyl), —(C$_1$-C$_6$-alkyl)-C(=O)—(C$_0$-C$_6$-alkyl)-heterocyclyl-C(=O)—O—(C$_1$-C$_6$-alkyl), —(C$_1$-C$_6$-alkyl)-O—C(=O)—O—(C$_1$-C$_6$-alkyl), —(C$_1$-C$_6$-alkyl)-O—C(=O)(C$_1$-C$_6$-alkyl), —(C$_1$-C$_6$-alkyl)-O—C(=O)(C$_3$-C$_6$-cycloalkyl), —(C$_1$-C$_6$-alkyl)-O—C(=O)—(C$_0$-C$_6$-alkyl)heteroaryl, —(C$_1$-C$_6$-alkyl)-O—C(=O)(C$_0$-C$_6$-alkyl)heterocyclyl, —(C$_1$-C$_6$-alkyl)-O—C(=O)—(C$_1$-C$_6$-alkyl)-N(R$^{3a}$)C(=O)—O—(C$_1$-C$_6$-alkyl), —(C$_0$-C$_6$-alkyl)-NR$^{3a}$R$^{3b}$, —(C$_1$-C$_6$-alkyl)-O—(C$_0$-C$_6$-alkyl)heteroaryl and —(C$_1$-C$_6$-alkyl)-O—(C$_0$-C$_6$-alkyl)heterocyclyl;
wherein each alkyl, cycloalkyl, alkenyl, alkynyl, phenyl, heteroaryl and heterocyclyl are unsubstituted or substituted with one or more substituents independently selected from halogen, CN, NO$_2$, NR$^{3a}$R$^{3b}$, C$_1$-C$_6$-alkyl, C$_1$-C$_6$-haloalkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_2$-C$_6$-alkynyl, —S(=O)(C$_1$-C$_6$-alkyl), —S(=O)$_2$(C$_1$-C$_6$-alkyl), —O—S(=O)$_2$(C$_1$-C$_6$-alkyl), —O—S(=O)$_2$(C$_1$-C$_6$-haloalkyl), —C(=O)H, —C(=O)OH, —C(=O)NR$^{3a}$R$^{3b}$, —(C$_1$-C$_6$-alkyl)NR$^{3a}$R$^{3b}$, —C(=O)(C$_1$-C$_6$-alkyl), —C(=O)O(C$_1$-C$_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{3a}$R$^{3b}$, —S(=O)$_2$NR$^{3a}$R$^{3b}$, heteroaryl and heterocyclyl;
Z is a 4- to 7-membered heterocyclyl or heteroaryl, which heterocyclyl or heteroaryl is unsubstituted or substituted with one or two substituents independently selected from halogen, CN, NO$_2$, oxo, hydroxy, —NR$^{Za}$R$^{Zb}$, C$_1$-C$_6$-alkyl, C$_1$-C$_6$-haloalkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_2$-C$_6$-alkynyl, —S(=O)(C$_1$-C$_6$-alkyl), —S(=O)$_2$(C$_1$-C$_6$-haloalkyl), —OS(=O)$_2$(C$_1$-C$_6$-alkyl), —OS(=O)$_2$(C$_1$-C$_6$-haloalkyl), —C(=O)H, —C(=O)OH, —C(=O)NR$^{Za}$R$^{Zb}$, —(C$_1$-C$_6$-alkyl)NR$^{Za}$R$^{Zb}$, —C(=O)(C$_1$-C$_6$-alkyl), —C(=O)O(C$_1$-C$_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{Za}$R$^{Zb}$, —S(O)$_2$NR$^{Za}$R$^{Zb}$, heteroaryl and heterocyclyl;
wherein each alkyl, cycloalkyl, alkenyl, alkynyl, phenyl, heteroaryl and heterocyclyl substituent is unsubstituted or substituted with one or more substituents independently selected from halogen, CN, NO$_2$, NR$^{Za}$R$^{Zb}$, C$_1$-C$_6$-alkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_2$-C$_6$-alkynyl, —S—(C$_1$-C$_6$-alkyl), —S(=O)(C$_1$-C$_6$-alkyl), —S(=O)$_2$(C$_1$-C$_6$-alkyl), —O—S(=O)$_2$(C$_1$-C$_6$-alkyl), —O—S(=O)$_2$(C$_1$-C$_6$-haloalkyl), —C(=O)H, —C(=O)OH, —C(=O)NR$^{Za}$R$^{Zb}$, —(C$_1$-C$_6$-alkyl)NR$^{Za}$R$^{Zb}$, —C(=O)(C$_1$-C$_6$-alkyl), —C(=O)O(C$_1$-C$_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{Za}$R$^{Zb}$, —S(=O)$_2$NR$^{Za}$R$^{Zb}$, heteroaryl and heterocyclyl;

R$^{3a}$, R$^{3b}$, R$^{Za}$ and R$^{Zb}$ are independently selected from H, C$_1$-C$_6$-alkyl, C$_1$-C$_6$-haloalkyl, C$_3$-C$_6$-cycloalkyl and C$_1$-C$_6$-alkoxy;
or an agrochemically acceptable salt, stereoisomer, tautomer, N-oxide thereof.

As used herein, when one embodiment refers to several other embodiments by using the term "according to any one of", for example "according to any one of embodiments 1 to 23", then said embodiment refers not only to embodiments indicated by integers such as 1 and 2 but also to embodiments indicated by numbers with a decimal component such as 23.1, 23.2, 23.3, 23.4, 23.20, 23.25, 23.30.

Embodiment 3

The compound according to embodiment 1 or 2, of formula (Ia)

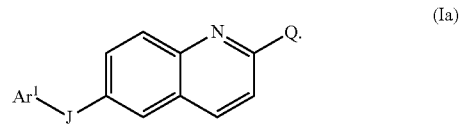

Embodiment 4

The compound according to embodiment 1 or 2, of formula (Ib)

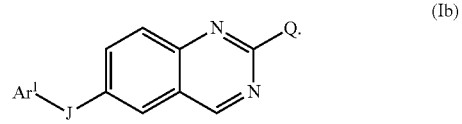

Embodiment 5

The compound according to embodiment 1 or 2, of formula (Ic)

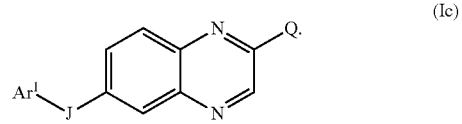

Embodiment 6

The compound according to embodiment 1 or 2, of formula (Id)

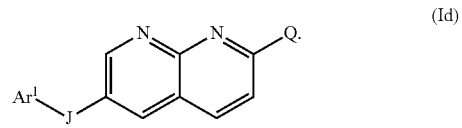

Embodiment 7

The compound according to embodiment 1 or 2, of formula (Ie)

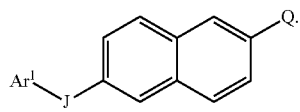

(Ie)

Embodiment 7.1

The compound according to embodiment 1 or 2, of formula (If)

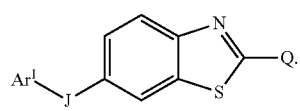

(If)

Embodiment 8

The compound according to any one of embodiments 1 to 7, wherein $Ar^1$ is selected from phenyl, furanyl, pyridazinyl, pyridyl, pyrimidinyl and thienyl, which furanyl, pyridazinyl, pyridyl, pyrimidinyl and thienyl are unsubstituted or substituted with 1 or 2 substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_3$-$C_6$halocycloalkyl, —$C_1$-$C_3$haloalkyl-$C_3$-$C_6$cycloalkyl, —($C_0$-$C_6$alkyl)heterocyclyl, halogen, CN, $NO_2$, $C_1$-$C_6$alkoxy, $C_1$-$C_6$haloalkoxy, —S—$C_1$-$C_6$alkyl, —S(=O)—$C_1$-$C_6$alkyl, —S(=O)$_2$—$C_1$-$C_6$alkyl, —S(=O)(=NH)$C_1$-$C_6$alkyl, —C(=O)($C_1$-$C_6$alkyl), CHO, —C(=O)($C_1$-$C_6$alkoxy) and —C(=O)($C_1$-$C_6$haloalkoxy).

Embodiment 9

The compound according to any one of embodiments 1 to 7, wherein $Ar^1$ is phenyl which is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_3$-$C_6$halocycloalkyl, —$C_1$-$C_3$haloalkyl-$C_3$-$C_6$cycloalkyl, —($C_0$-$C_6$alkyl)heterocyclyl, halogen, CN, $NO_2$, $C_1$-$C_6$alkoxy, $C_1$-$C_6$haloalkoxy, —S—$C_1$-$C_6$alkyl, —S(=O)—$C_1$-$C_6$alkyl, —S(=O)$_2$—$C_1$-$C_6$alkyl, —S(=O)(=NH)$C_1$-$C_6$alkyl, —C(=O)($C_1$-$C_6$alkyl), CHO, —C(=O)($C_2$-$C_6$alkoxy) and —C(=O)($C_1$-$C_6$haloalkoxy).

Embodiment 10

The compound according to embodiment 8, wherein $Ar^1$ is phenyl which is unsubstituted or substituted by one to three substituents independently selected from $C_1$-$C_6$alkyl, $C_1$-$C_6$haloalkyl, halogen, $C_1$-$C_6$alkoxy and $C_1$-$C_6$haloalkoxy.

Embodiment 11

A compound according to any one of embodiments 1 to 9, wherein $Ar^2$ is phenyl which is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_3$-$C_6$halocycloalkyl, —$C_1$-$C_3$haloalkyl-$C_3$-$C_6$cycloalkyl, $C_3$-$C_6$cycloalkoxy, halogen, cyano, $C_1$-$C_6$alkoxy, $C_1$-$C_6$haloalkoxy and —S—$C_1$-$C_6$alkyl.

Embodiment 12

A compound according to any one of embodiments 1 to 9, wherein $Ar^2$ is phenyl which is unsubstituted or substituted by one to three substituents independently selected from $C_1$-$C_4$alkyl, $C_1$-$C_4$haloalkyl, halogen, $C_1$-$C_4$alkoxy and $C_1$-$C_4$haloalkoxy.

Embodiment 13

A compound according to any one of embodiments 1 to 12, wherein W is $NR^1$ and $R^1$ is H.

Embodiment 14

A compound according to any one of embodiments 1 to 13, wherein $R^2$ is selected from H, $C_1$-$C_6$alkyl and $C_1$-$C_6$haloalkyl.

Embodiment 15

A compound according to any one of embodiments 1 to 14, wherein $R^3$ is selected from —C(=O)—($C_0$-$C_6$-alkyl)(heteroaryl), —C(=O)—($C_0$-$C_6$-alkyl)(heterocyclyl), —($C_0$-$C_6$-alkyl)(heteroaryl), —($C_0$-$C_6$-alkyl)(heterocyclyl), —($C_0$-$C_6$-alkyl)-O-(heteroaryl) and —($C_0$-$C_6$-alkyl)-O-(heterocyclyl), which alkyl, heteroaryl and heterocyclyl are unsubstituted or substituted with one to three substituents independently selected from halogen, $C_1$-$C_6$-alkyl, $C_1$-$C_6$-haloalkyl, $C_1$-$C_6$-alkoxy, $C_1$-$C_6$-haloalkoxy, —S(=O)—$C_1$-$C_6$-alkyl, —S(=O)$_2$—$C_1$-$C_6$-alkyl, —C(=O)OH, —C(=O)O($C_1$-$C_6$-alkyl), phenyl and —Si($C_1$-$C_6$-alkyl)$_3$.

Embodiment 16

A compound according to any one of embodiments 1 to 14, wherein $R^3$ is selected from —($C_0$-$C_6$-alkyl)(heteroaryl) and —($C_0$-$C_6$-alkyl)(heterocyclyl), which alkyl, heteroaryl and heterocyclyl are unsubstituted or substituted with one to three substituents independently selected from halogen, $C_1$-$C_6$-alkyl, $C_1$-$C_6$-haloalkyl, $C_1$-$C_6$-alkoxy and $C_1$-$C_6$-haloalkoxy.

Embodiment 17

A compound according to any one of embodiments 1 to 16, wherein Z is a 4- to 7-membered heterocyclyl or heteroaryl, which heterocyclyl or heteroaryl is unsubstituted or substituted with one or two substituents independently selected from $C_1$-$C_6$-alkyl, $C_1$-$C_4$alkoxy, oxo, hydroxy, —C(=O)OH, phenyl, heteroaryl and heterocyclyl, and wherein each phenyl, heterocyclyl and heteroaryl substituent is unsubstituted or substituted with one or two substituents independently selected from oxo, hydroxy, $C_1$-$C_4$haloalkyl, $C_1$-$C_4$haloalkoxy and —C(=O)OH.

Embodiment 18

A compound according to any one of embodiments 1 to 16, wherein Z is a 4- to 7-membered heterocyclyl or heteroaryl, which heterocyclyl or heteroaryl is unsubstituted or substituted with one or two substituents independently selected from $C_1$-$C_6$-alkyl, $C_1$-$C_4$alkoxy, oxo and hydroxy.

Embodiment 19

A compound according to any one of embodiments 1 to 16, wherein Z is a 5-membered heterocyclyl or heteroaryl, which heterocyclyl or heteroaryl is unsubstituted or substituted with one or two substituents independently selected from $C_1$-$C_6$-alkyl, oxo and hydroxy.

Embodiment 20

A compound according to any one of embodiments 1 to 19, wherein J is a 5- or 6-membered heteroaryl, wherein said heteroaryl is unsubstituted or substituted with one to three substituents independently selected from $C_1$-$C_6$alkyl, $C_2$-$C_6$alkenyl, $C_2$-$C_6$alkynyl, —($C_0$-$C_6$-alkyl)$C_{3-8}$cycloalkyl, $C_1$-$C_6$haloalkyl, $C_2$-$C_6$haloalkenyl, $C_2$-$C_6$haloalkynyl, —($C_0$-$C_6$-alkyl)$C_{3-8}$halocycloalkyl, —$C_1$-$C_3$haloalkyl-$C_3$-$C_6$cycloalkyl, —($C_0$-$C_6$-alkyl)(heterocyclyl), halogen, CN, —$C_1$-$C_4$alkyl-CN, —$C_3$-$C_6$cycloalkyl-CN, NO$_2$, $C_1$-$C_6$alkoxy, $C_1$-$C_4$haloalkoxy, $C_1$-$C_4$alkoxy-$C_1$-$C_4$alkyl S—$C_1$-$C_6$alkyl, —S(O)—$C_1$-$C_6$alkyl, —S($=$O)$_2$ $C_1$-$C_6$alkyl, —S($=$O)($=$NH)$C_1$-$C_6$alkyl, —S—$C_1$-$C_6$haloalkyl, —S(O)—$C_1$-$C_6$haloalkyl, —S($=$O)$_2C_1$-$C_6$haloalkyl, —S($=$O)($=$NH)$C_1$-$C_6$haloalkyl, —NH($C_1$-$C_6$alkyl), —N($C_2$-$C_6$alkyl)$_2$, —NH($C_3$-$C_6$cycloalkyl), —N($C_1$-$C_6$alkyl)($C_3$-$C_6$cycloalkyl), —C($=$O)($C_1$-$C_6$alkyl), CHO, —C($=$O)($C_2$-$C_6$alkoxy), —C($=$O)($C_1$-$C_6$haloalkoxy), —C($=$O)NH($C_1$-$C_6$alkyl), —C($=$O)NH($C_1$-$C_6$haloalkyl) and —C($=$O)N($C_1$-$C_6$alkyl)$_2$.

Embodiment 21

A compound according to any one of embodiments 1 to 19, wherein J is selected from triazolyl, imidazolyl and pyrazolyl, which triazolyl, imidazolyl and pyrazolyl are unsubstituted or substituted with one or two substituents independently selected from $C_1$-$C_6$alkyl, $C_2$-$C_6$alkenyl, $C_2$-$C_6$alkynyl, —($C_{0-6}$alkyl)$C_{3-8}$cycloalkyl, $C_1$-$C_6$haloalkyl, $C_2$-$C_6$haloalkenyl, $C_2$-$C_6$haloalkynyl, —($C_{0-6}$alkyl)$C_{3-8}$halocycloalkyl and halogen.

Embodiment 22

A compound according to any one of embodiments 1 to 19, wherein J is

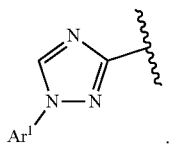

Embodiment 23

A compound according to any one of embodiments 1 to 19, wherein J is

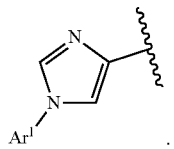

Embodiment 24

A compound according to any one of embodiments 1 to 19, wherein J is

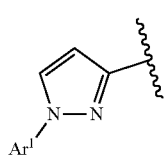

Embodiment 25

A compound according to any one of embodiments 1 to 19, wherein J is

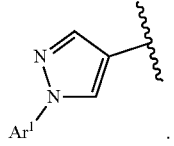

Embodiment 26

A compound according to any one of embodiments 1 to 25, wherein
Q is selected from

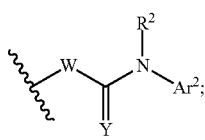

(i)

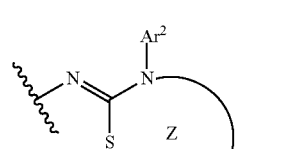

(iv)

; and

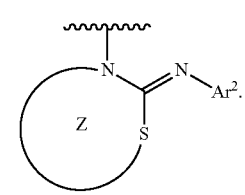

(v)

Embodiment 27

A compound according to any one of embodiments 1 to 25, wherein
Q is

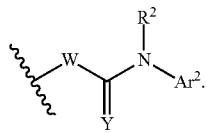

Embodiment 28

A compound according to any one of embodiments 1 to 25, wherein
Q is

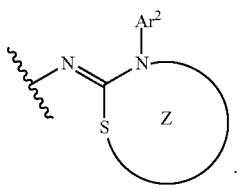

Embodiment 29

A compound according to any one of embodiments 1 to 25, wherein
Q is

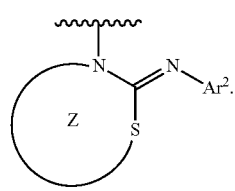

Embodiment 30

A compound according to any one of embodiments 1 to 7, wherein
Q is

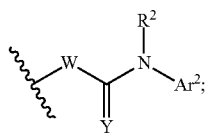

W is NH;
Y is O or S;
$R^2$ is selected from H, $C_1$-$C_6$alkyl and $C_1$-$C_6$haloalkyl;

J is

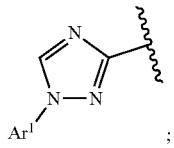

$Ar^1$ is phenyl which is unsubstituted or substituted by one to three substituents independently selected from $C_1$-$C_6$alkyl, $C_1$-$C_6$haloalkyl, halogen, $C_1$-$C_6$alkoxy and $C_1$-$C_6$haloalkoxy;
$Ar^2$ is phenyl which is unsubstituted or substituted by one to three substituents independently selected from $C_1$-$C_4$alkyl, $C_1$-$C_4$haloalkyl, halogen, $C_1$-$C_4$alkoxy and $C_1$-$C_4$haloalkoxy;
or an agrochemically acceptable salt, stereoisomer, tautomer, N-oxide thereof.

Embodiment 31

A compound according to any one of embodiments 1 to 7, wherein
Q is

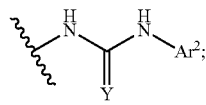

Y is O or S;
J is

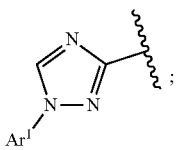

$Ar^1$ is

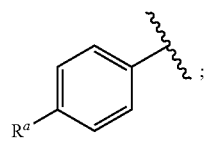

$R^a$ is selected from $C_1$-$C_6$alkyl, $C_1$-$C_6$haloalkyl, halogen, $C_1$-$C_6$alkoxy and $C_1$-$C_6$haloalkoxy;
$Ar^2$ is

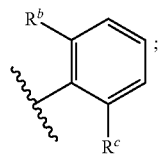

$R^b$ and $R^c$ are independently selected from H, $C_1$-$C_6$alkyl and halogen; preferably $R^b$ is $C_1$-$C_6$alkyl and $R^c$ is H, more preferably $R^b$ is isopropyl and $R^c$ is H;

or an agrochemically acceptable salt, stereoisomer, tautomer, N-oxide thereof.

Embodiment 32

A compound according to any one of embodiments 1 to 7, wherein
Q is

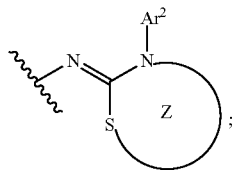

Ar² is phenyl which is unsubstituted or substituted by one to three substituents independently selected from $C_1$-$C_4$alkyl, $C_1$-$C_4$haloalkyl, halogen, $C_1$-$C_4$alkoxy and $C_1$-$C_4$haloalkoxy;
Z is a 4- to 7-membered heterocyclyl or heteroaryl, which heterocyclyl or heteroaryl is unsubstituted or substituted with one or two substituents independently selected from $C_1$-$C_6$-alkyl, $C_1$-$C_4$alkoxy, oxo and hydroxy;
or an agrochemically acceptable salt, stereoisomer, tautomer, N-oxide thereof.

Embodiment 33

A compound according to any one of embodiments 1 to 7, wherein
Q is

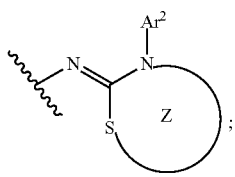

Ar² is

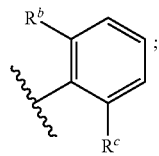

$R^b$ and $R^c$ are independently selected from H, $C_1$-$C_6$alkyl and halogen; preferably $R^b$ is $C_1$-$C_6$alkyl and $R^c$ is H, more preferably $R^b$ is isopropyl and $R^c$ is H;
Z is a 5 or 6-membered heterocyclyl or heteroaryl, which heterocyclyl or heteroaryl is unsubstituted or substituted with one or two substituents independently selected from $C_1$-$C_6$-alkyl, oxo and hydroxy;
or an agrochemically acceptable salt, stereoisomer, tautomer, N-oxide thereof.

Embodiment 34

A compound according to any one of embodiments 1 to 7, wherein
Q is

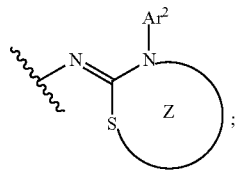

Ar² is

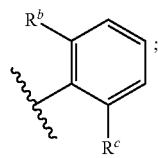

$R^b$ and $R^c$ are independently selected from H, $C_1$-$C_6$alkyl and halogen; preferably $R^b$ is $C_1$-$C_6$alkyl and $R^c$ is H, more preferably $R^b$ is isopropyl and $R^c$ is H;
Z is a 5-membered heterocyclyl or heteroaryl, which heterocyclyl or heteroaryl is unsubstituted or substituted with one or two substituents independently selected from $C_1$-$C_6$-alkyl, oxo and hydroxy;
or an agrochemically acceptable salt, stereoisomer, tautomer, N-oxide thereof.

Embodiment 35

A compound according to any one of embodiments 1 to 7, wherein
Q is

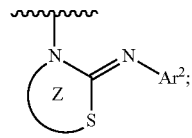

Ar² is

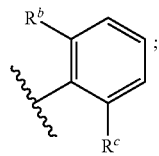

$R^b$ and $R^c$ are independently selected from H, $C_1$-$C_6$alkyl and halogen; preferably $R^b$ is $C_1$-$C_6$alkyl and $R^c$ is H, more preferably $R^b$ is isopropyl and $R^c$ is H;
Z is a 5 or 6-membered heterocyclyl or heteroaryl, which heterocyclyl or heteroaryl is unsubstituted or substituted with one or two substituents independently selected from $C_1$-$C_6$-alkyl, oxo and hydroxy;
or an agrochemically acceptable salt, stereoisomer, tautomer, N-oxide thereof.

Embodiment 36

A compound according to any one of embodiments 1 to 7, wherein

Q is

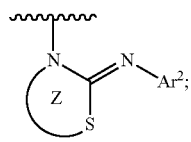

Ar² is

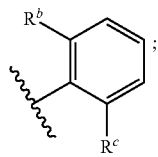

$R^b$ and $R^c$ are independently selected from H, $C_1$-$C_6$alkyl and halogen; preferably $R^b$ is $C_1$-$C_6$alkyl and $R^c$ is H, more preferably $R^b$ is isopropyl and $R^c$ is H;
Z is a 5-membered heterocyclyl or heteroaryl, which heterocyclyl or heteroaryl is unsubstituted or substituted with one or two substituents independently selected from $C_1$-$C_6$-alkyl, oxo and hydroxy; or an agrochemically acceptable salt, stereoisomer, tautomer, N-oxide thereof.

Embodiment 37

A compound according to claim 1, wherein the compound is selected from
1-(2-isopropylphenyl)-3-[6-[1-[4-(trifluoromethoxy)phenyl]-1,2,4-triazol-3-yl]-2-quinolyl]thiourea (P1.4);
1-(2-isopropylphenyl)-3-[6-[1-[4-(trifluoromethoxy)phenyl]-1,2,4-triazol-3-yl]-2-quinolyl]urea (P1.3);
3-(2-isopropylphenyl)-N-[6-[1-[4-(trifluoromethoxy)phenyl]-1,2,4-triazol-3-yl]-2-quinolyl]-1,3-thiazetidin-2-imine (P2.1);
3-(2-isopropylphenyl)-4-methyl-N-[6-[1-[4-(trifluoromethoxy)phenyl]-1,2,4-triazol-3-yl]-2-quinolyl]thiazol-2-imine (P2.2);
(2Z)-3-(2-isopropylphenyl)-2-[[6-[1-[4-(trifluoromethoxy)phenyl]-1,2,4-triazol-3-yl]-2-quinolyl]imino]thiazolidin-4-one (P2.3);
(2E)-2-(2-isopropylphenyl)imino-3-[6-[1-[4-(trifluoromethoxy)phenyl]-1,2,4-triazol-3-yl]-2-quinolyl]thiazolidin-4-one (P2.4);
3-(2-isopropylphenyl)-N-[6-[1-[4-(trifluoromethoxy)phenyl]-1,2,4-triazol-3-yl]-2-quinolyl]-1,3-thiazetidin-2-imine (P2.1);
3-(2-isopropylphenyl)-4-methyl-N-[6-[1-[4-(trifluoromethoxy)phenyl]-1,2,4-triazol-3-yl]-2-quinolyl]thiazol-2-imine (P2.2);
(2Z)-3-(2-isopropylphenyl)-2-[[6-[1-[4-(trifluoromethoxy)phenyl]-1,2,4-triazol-3-yl]-2-quinolyl]imino]thiazolidin-4-one (P2.3);
(2E)-2-(2-isopropylphenyl)imino-3-[6-[1-[4-(trifluoromethoxy)phenyl]-1,2,4-triazol-3-yl]-2-quinolyl]thiazolidin-4-one (P2.4);
1-(2-chloro-6-methyl-phenyl)-3-[6-[1-(p-tolyl)-1,2,4-triazol-3-yl]-2-quinolyl]thiourea (P1.5);
1-(2,6-dimethylphenyl)-3-[6-[1-(p-tolyl)-1,2,4-triazol-3-yl]-2-naphthyl]thiourea (P1.6);
1-(2-isopropylphenyl)-3-[6-[1-(p-tolyl)-1,2,4-triazol-3-yl]-2-naphthyl]thiourea (P1.7);
1-(2-isopropylphenyl)-3-[6-[1-(p-tolyl)-1,2,4-triazol-3-yl]-2-naphthyl]urea (P1.8);
1-(2-chloro-6-methyl-phenyl)-3-[6-[1-(p-tolyl)-1,2,4-triazol-3-yl]-2-naphthyl]thiourea (P1.9);
1-(2,6-dimethylphenyl)-3-[6-[1-(p-tolyl)-1,2,4-triazol-3-yl]quinazolin-2-yl]thiourea (P1.10);
1-(2-isopropylphenyl)-3-[6-[1-(p-tolyl)-1,2,4-triazol-3-yl]quinazolin-2-yl]thiourea (P1.11);
1-(2-isopropylphenyl)-3-[6-[1-(p-tolyl)-1,2,4-triazol-3-yl]quinazolin-2-yl]urea (P1.12);
1-(2-chloro-6-methyl-phenyl)-3-[6-[1-(p-tolyl)-1,2,4-triazol-3-yl]quinazolin-2-yl]thiourea (P1.13);
1-(2,6-dimethylphenyl)-3-[6-[1-(p-tolyl)-1,2,4-triazol-3-yl]quinoxalin-2-yl]thiourea (P1.14);
1-(2-isopropylphenyl)-3-[6-[1-(p-tolyl)-1,2,4-triazol-3-yl]quinoxalin-2-yl]thiourea (P1.15);
1-(2-isopropylphenyl)-3-[6-[1-(p-tolyl)-1,2,4-triazol-3-yl]quinoxalin-2-yl]urea (P1.16);
1-(2-chloro-6-methyl-phenyl)-3-[6-[1-(p-tolyl)-1,2,4-triazol-3-yl]quinoxalin-2-yl]thiourea (P1.17);
1-(2,6-dimethylphenyl)-3-[6-[1-(p-tolyl)-1,2,4-triazol-3-yl]-1,8-naphthyridin-2-yl]thiourea (P1.18);
1-(2-isopropylphenyl)-3-[6-[1-(p-tolyl)-1,2,4-triazol-3-yl]-1,8-naphthyridin-2-yl]thiourea (P1.19);
1-(2-chloro-6-methyl-phenyl)-3-[6-[1-(p-tolyl)-1,2,4-triazol-3-yl]-1,8-naphthyridin-2-yl]thiourea (P1.20);
1-(2-chloro-6-methyl-phenyl)-3-[6-[1-(p-tolyl)-1,2,4-triazol-3-yl]-1,8-naphthyridin-2-yl]urea (P1.21);
1-(2-isopropylphenyl)-3-[3-[1-(p-tolyl)-1,2,4-triazol-3-yl]-7-quinolyl]thiourea (P1.22);
1-(2-isopropylphenyl)-3-[2-[1-(p-tolyl)-1,2,4-triazol-3-yl]-6-quinolyl]thiourea (P1.23); and
1-(2-isopropylphenyl)-3-[7-[1-(p-tolyl)-1,2,4-triazol-3-yl]-1,8-naphthyridin-3-yl]thiourea (P1.24);
or an agrochemically acceptable salt, stereoisomer, tautomer, N-oxide thereof.

The term "compounds of the (present) invention" or "a compound of the (present) invention" refers to a compound as defined in any one of embodiment 1 to 37.

The compounds according to any one of embodiments 1 to 37 may be prepared according to the following Schemes 1 to 6 or according to methods described in WO2012/109125. The process for preparing compounds of the present invention is carried out in principle by methods known to those skilled in the art. The reagents in Schemes 1-6 are either commercially available or may be prepared according to known methods.

Compounds of formula (I.1) may be prepared, as depicted in scheme 1, by reacting compounds (1) with compounds (2), wherein X is O or S, in the presence or in the absence of a base, such as sodium carbonate or triethylamine, DBU (1,8-Diazabicyclo[5.4.0]undec-7-ene), DBN (1,5-Diazabicyclo[4.3.0]non-5-ene), NaH, NaOMe or NaOtBu, in a suitable solvent or a solvent mixture, such as tetrahydrofuran, DMF, dioxane or acetonitrile. The reaction temperature can preferentially range from room temperature to the boiling point of the reaction mixture.

Scheme 1

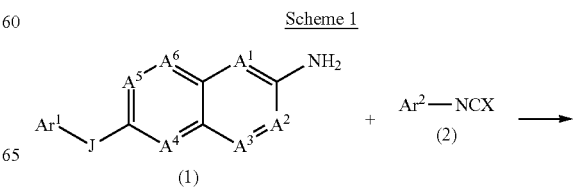

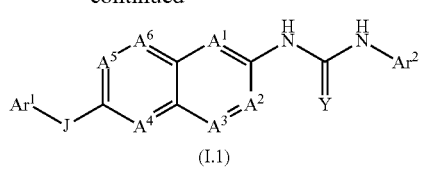

(I.1)

wherein Ar¹, Y, J, A¹, A², A³, A⁴, A⁵, A⁶, and Ar² are as described in any one of embodiments 1 to 37.

Compounds (10) may be prepared according to scheme 2. Compounds (3) or their preparation methods are known from the literature (e.g. A. K. Katritstky, A. F. Pozharskii, Handbook of Heterocyclic Chemistry, 2$^{nd}$ edition, Pergamon, Oxford, 2000). Cyanation to compound (4) may be done under Pd or Cu catalysis, with CuHal or Zn(CN)$_2$ as the CN source. Compounds (4) may be chlorinated to compounds (5), which may be further substituted with a compound of formula HN(PG¹)(PG²) through a Pd or Cu catalysed reaction. PG$_1$ and PG$_2$ are independently selected from H, COOtBu, COOMe, COOEt, SiMe$_3$, allyl. The cyano group may be converted to a 1,2,4-triazole compounds (9) through hydrolysis to a compound (7), reaction with DMF-DMA and cyclisation with hydrazine hydrate. Compounds (10) may be obtained by reaction of a compound (9) with Ar¹-Hal or Ar¹—B(OH)$_2$ under Cu or Pd catalysis. Pd or Cu catalysis methods and conditions are described in *Metal-Catalyzed Cross-Coupling Reactions*, 2$^{nd}$ Edition, A. de Meijere, F. Diederich eds, Wiley-VCH, Weinheim, 2004. Hal is halogen, Ar¹, A¹, A², A³, A⁴, A⁵ and A⁶ are as described above.

Scheme 2

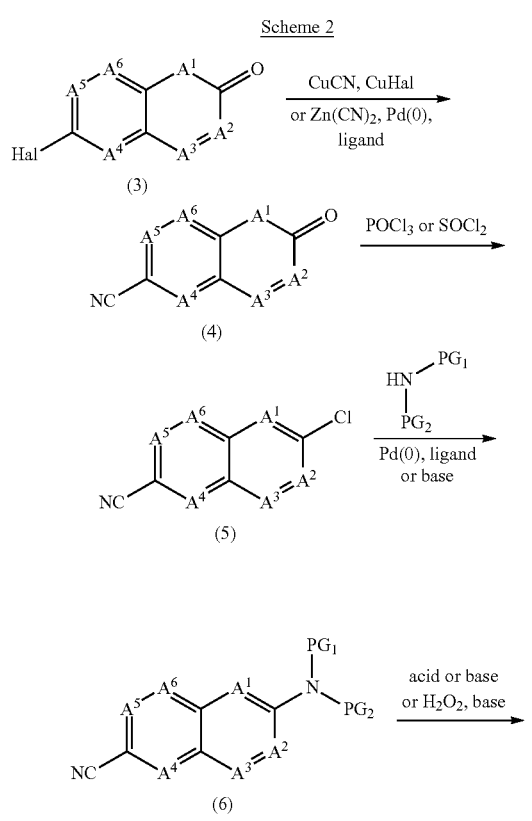

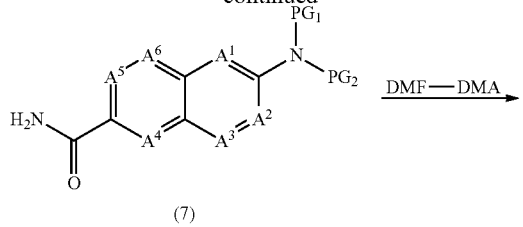

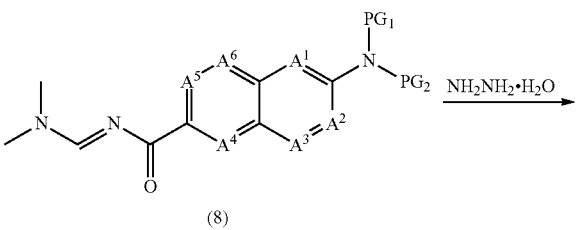

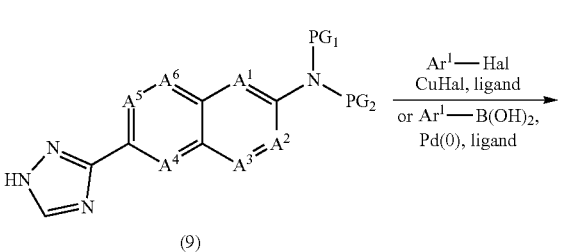

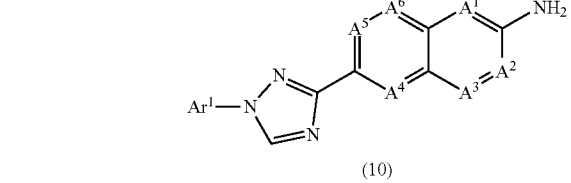

wherein A¹, A², A³, A⁴, A⁵ and A⁶ are as described in any one of embodiments 1 to 37, Hal is a halogen, particularly chloro or iodo. PG$_1$ and PG$_2$ are independently selected from H, COOtBu, COOMe, COOEt, SiMe$_3$, allyl.

Compounds (1) may also be prepared according to scheme 3. Compounds (11) or their preparation methods are known from the literature (e.g. A. K. Katritstky, A. F. Pozharskii, Handbook of Heterocyclic Chemistry, 2$^{nd}$ edition, Pergamon, Oxford, 2000). They can be chlorinated to a compound (12), which reacts under Suzuki conditions with a compound of formula Ar¹-J-B(OH)$_2$ or Ar¹-J-B(Pin) to a compound of formula (13). Alternatively, a compound of formula (14) may be prepared from a compound (12) through metalation (nBuli, or iPrMgCl or iPrMgCl.LiCl) and reaction with a borate (e.g. B(OiPr)$_3$). Compounds (14) may react with a compound of formula Ar¹-J-Hal to a compound (13) in a Suzuki reaction. Compound (13) can be transformed to a compound of formula (15) by reacting with a compound of formula HN(PG$_1$)(PG$_2$) under Cu or Pd catalysis. Conditions for the Suzuki reactions and Pd or Cu catalysed reactions are described in *Metal-Catalyzed Cross-Coupling Reactions*, 2$^{nd}$ Edition, A. de Meijere, F. Diederich eds, Wiley-VCH, Weinheim, 2004.

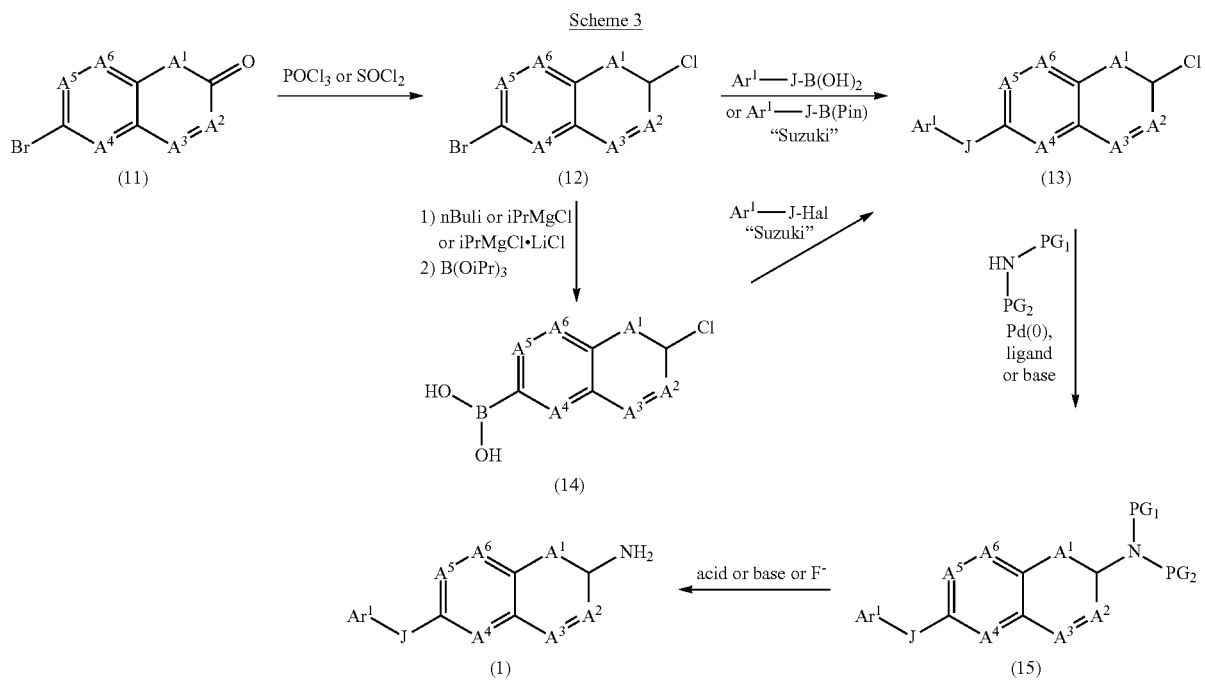

Scheme 3 wherein Hal is halogen, J, $Ar^1$, $A^1$, $A^2$, $A^3$, $A^4$, $A^5$, and $A^6$ are as described in any one of embodiments 1 to 37. $PG^1$ and $PG^2$ are independently H, COOtBu, COOMe, COOEt, $SiMe_3$, allyl.

Alternatively, compounds (1) may be prepared as depicted in scheme 4, by modifying the reaction sequence described in scheme 3. Hal is halogen, J, $Ar^1$, $A^1$, $A^2$, $A^3$, $A^4$, $A^5$ and $A^6$ are as described in any one of embodiments 1 to 37. $PG_1$ and $PG_2$ are independently H, COOtBu, COOMe, COOEt, $SiMe_3$, allyl.

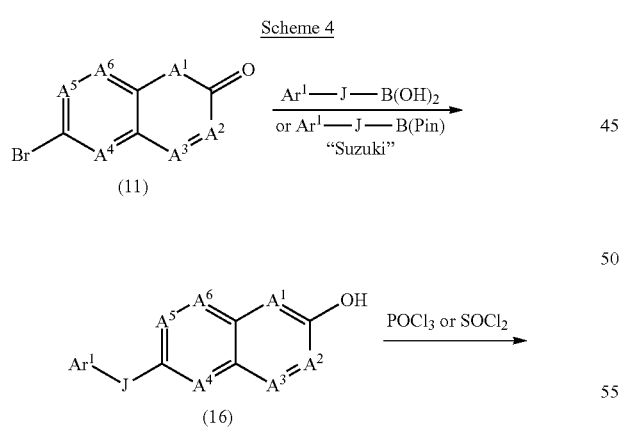

Scheme 4

Compounds of formula (I.3), (I.4), (I.5) and (I.6) can be prepared from a compound of formula (I.2) according to scheme 5 in the presence or in the absence of a base such as $Na_2CO_3$, $NEt_3$, DBU, DBN, MeONa, tBuONa. LG is a leaving group e.g. Cl, Br, I, OMes, OTos, OMe. J, $Ar^1$, $A^1$, $A^2$, $A^3$, $A^4$, $A^5$, $A^6$, $Ar^2$ and $R^3$ are as described in any one of embodiments 1 to 37. $R^5$ is a —($C_1$-$C_4$alkyl)- which may be unsubstituted or substituted with a substituent as described for Z in embodiments 17-19. In each reaction, a mixture of compounds of formula (I.3) and (I.4) or (I.5) and (I.6) can be formed and can be separated by crystallization or chromatography methods.

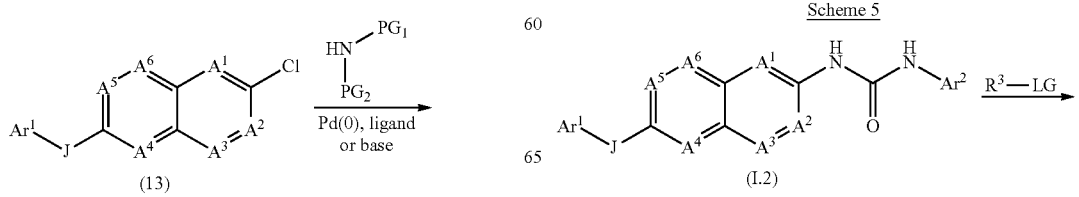

Scheme 5

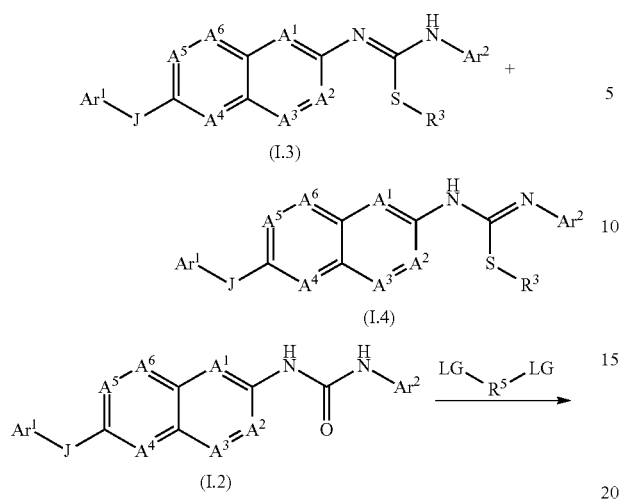

(I.3)

(I.4)

(I.2)

(I.5)

(I.6)

Alternatively, compounds (I.7) and (I.8) may be prepared by reacting a compound (I.2) with chloroacetone or bromoacetone in the presence of a base such as $Na_2CO_3$, $NEt_3$, DBU, DBN, MeONa, tBuONa. J, $Ar^1$, $A^1$, $A^2$, $A^3$, $A^4$, $A^5$, $A^6$ and $Ar^2$ are as described above, Hal' is Cl or Br. A mixture of compounds of formula (I.7) and (I.8) can be formed and can be separated by crystallization or chromatography methods.

Scheme 6

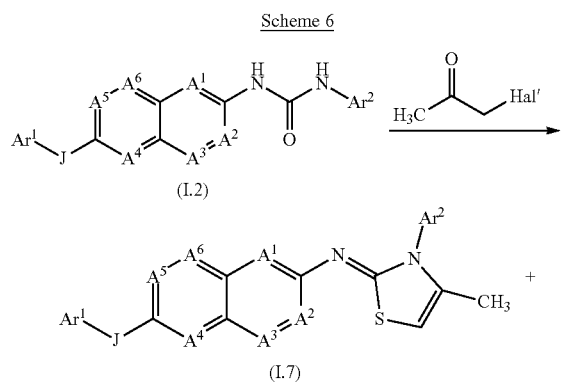

(I.2)

(I.7)

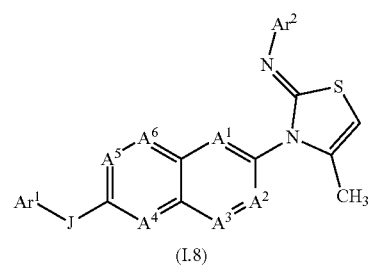

(I.8)

Compounds of formula (I'.1) may be prepared, as depicted in scheme 7, by reacting compounds (1') with compounds (2), wherein X is O or S, in the presence or in the absence of a base, such as sodium carbonate or triethylamine, DBU (1,8-diazabicyclo[5.4.0]undec-7-ene), DBN (1,5-diazabicyclo[4.3.0]non-5-ene), NaH, $Na_0Me$ or NaOtBu, in a suitable solvent or a solvent mixture, such as tetrahydrofuran, DMF, dioxane or acetonitrile. The reaction temperature can preferentially range from room temperature to the boiling point of the reaction mixture.

Scheme 7

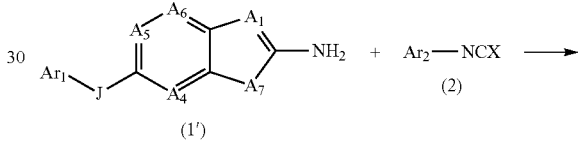

(1')         (2)

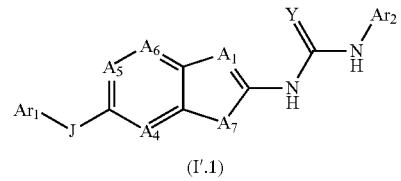

(I'.1)

Compounds (1') may be prepared according to scheme 8. Compounds (11') or their preparation methods are known from the literature (e.g. A. K. Katritstky, A. F. Pozharskii, Handbook of Heterocyclic Chemistry, $2^{nd}$ edition, Pergamon, Oxford, 2000). They can be chlorinated to a compound (12'), which reacts under Suzuki conditions with a compound of formula $Ar^1$-J-B(OH)$_2$ or $Ar^1$-J-B(Pin) to a compound of formula (13'). Alternatively, a compound of formula (14') may be prepared from a compound (12') through metalation (nBuli, or iPrMgCl or iPrMgCl.LiCl) and reaction with a borate (e.g. $B(OiPr)_3$). Compounds (14') may react with a compound of formula $Ar^1$-J-Hal to a compound (13') in a Suzuki reaction. Compound (13') can be transformed to a compound of formula (15') by reacting with a compound of formula $HN(PG_1)(PG_2)$ under Cu or Pd catalysis. Conditions for the Suzuki reactions and Pd or Cu catalysed reactions are described in *Metal-Catalyzed Cross-Coupling Reactions*, $2^{nd}$ Edition, A. de Meijere, F. Diederich eds, Wiley-VCH, Weinheim, 2004.

Scheme 8

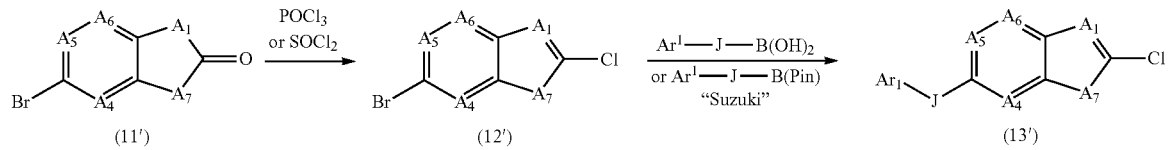

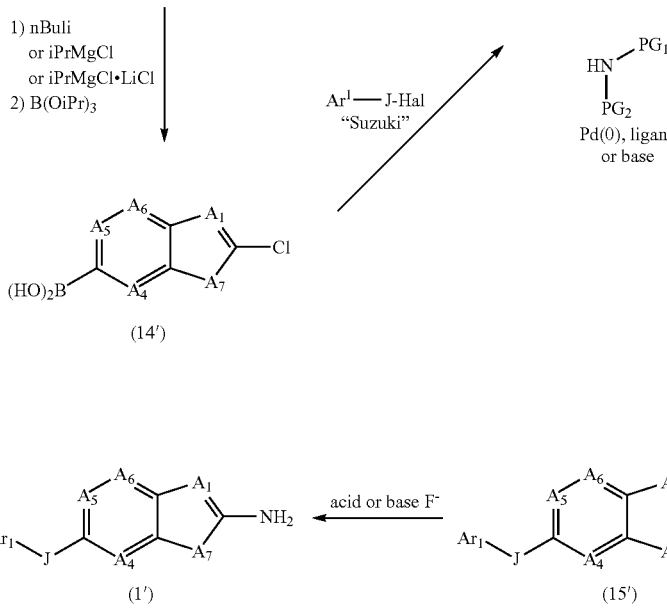

Alternatively compounds (1') may be prepared according to scheme 9. Compounds (16') or their preparation methods are known from the literature (e.g. A. K. Katritstky, A. F. Pozharskii, Handbook of Heterocyclic Chemistry, $2^{nd}$ edition, Pergamon, Oxford, 2000). They can react under Suzuki conditions with a compound of formula $Ar^1$-J-B(OH)$_2$ or $Ar^1$-J-B(Pin) to a compound of formula (1'). Alternatively, a compound of formula (17') may be prepared from a compound (16') through metalation (nBuli, or iPrMgCl or iPrMgCl.LiCl) and reaction with a borate (e.g. B(OiPr)$_3$). Compounds (17') may react with a compound of formula $Ar^1$-J-Hal to a compound (1') in a Suzuki reaction. Conditions for the Suzuki reactions and Pd or Cu catalysed reactions are described in *Metal-Catalyzed Cross-Coupling Reactions*, $2^{nd}$ Edition, A. de Meijere, F. Diederich eds, Wiley-VCH, Weinheim, 2004.

Scheme 9

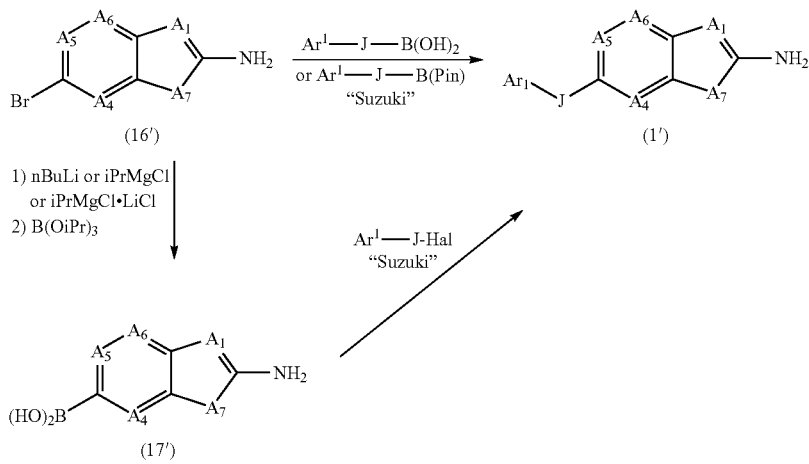

Compounds of formula (I'.3), (I'.4), (I'.5) and (I'.6) can be prepared from a compound of formula (I'.2) according to scheme 10 in the presence or in the absence of a base such as Na$_2$CO$_3$, NEt$_3$, DBU, DBN, MeONa, tBuONa. LG is a leaving group e.g. Cl, Br, I, OMes, OTos, OMe. J, Ar$^1$, A$^1$, A$^2$, A$^3$, A$^4$, A$^5$, A$^6$, Ar$^2$ and R$^3$ are as described in any one of embodiments 1 to 37. R$^5$ is a (C$_1$-C$_4$alkyl)- which may be unsubstituted or substituted with a substituent as described for Z in embodiments 17-19. In each reaction, a mixture of compounds of formula (I'.3) and (I'.4) or (I'.5) and (I'.6) can be formed and can be separated by crystallization or chromatography methods.

Scheme 10

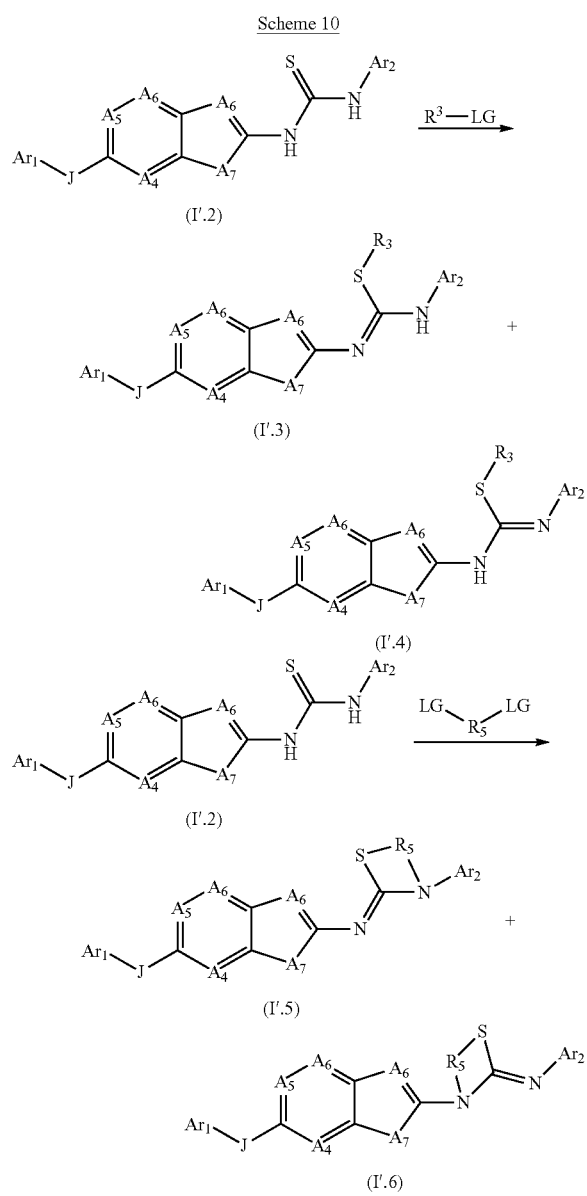

Depending on the procedure or the reaction conditions, the compounds of the invention which have salt-forming properties can be obtained in free form or in the form of salts.

The compounds according to any one of embodiments 1 to 37 and, where appropriate, the tautomers thereof, in each case in free form or in salt form, can be present in the form of one of the stereoisomers which are possible or as a mixture of these, for example in the form of pure stereoisomers, such as antipodes and/or diastereomers, or as stereoisomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure stereoisomers and also to all stereoisomer mixtures which are possible and is to be understood in each case in this sense hereinabove and herein below, even when stereochemical details are not mentioned specifically in each case.

Diastereomer mixtures or racemate mixtures of compounds according to any one of embodiments 1 to 37, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be resolved by the action of suitable agents, for example basic agents.

Pure diastereomers or enantiomers can be obtained not only by separating suitable stereoisomer mixtures, but also by generally known methods of diastereoselective or enantioselective synthesis, for example by carrying out the process according to the invention with starting materials of a suitable stereochemistry.

N-oxides can be prepared by reacting a compound according to any one of embodiments 1 to 37 with a suitable oxidizing agent, for example the H$_2$O$_2$/urea adduct in the presence of an acid anhydride, e.g. trifluoroacetic anhydride. Such oxidations are known from the literature, for example from J. Med. Chem. 1989, 32, 2561 or WO 2000/15615.

The compounds according to any one of embodiments 1 to 37 and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to any one of embodiments 1 to 37 are preventively and/or curatively valuable active ingredients in the field of pest control, even at low rates of application, which have a favorable biocidel spectrum and are well tolerated by warm-blooded species, fish and plants. Compounds according to any one of embodiments 1 to 37 may act against all or only individual developmental stages of normally sensitive, but also resistant, animal pests, such as insects or representatives of the order Acarina. The insecticidal or acaricidal activity of the compounds can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example, *Acalitus* spp, *Aculus* spp, *Acaricalus* spp, *Aceria* spp, Acarus siro, *Amblyomma* spp., *Argas* spp., *Boophilus* spp., *Brevipalpus* spp., *Bryobia* spp, *Calipitrimerus* spp., *Chorioptes* spp., *Dermanyssus* gallinae, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., Polyphagotarsone latus, *Panonychus* spp., Phyllocoptruta oleivora, *Phytonemus* spp, *Polypha-gotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example, *Haematopinus* spp., *Linognathus* spp., *Pediculus* spp., *Pemphigus* spp. and *Phylloxera* spp.;

from the order Coleoptera, for example, *Agriotes* spp., Amphimallon majale, Anomala orientalis, *Anthonomus* spp., *Aphodius* spp, Astylus atromaculatus, *Ataenius* spp, Atomaria linearis, Chaetocnema tibialis, *Cerotoma* spp, *Conoderus* spp., *Cosmopolites* spp., Cotinis nitida, *Curculio* spp., *Cyclocephala* spp, *Dermestes* spp., *Diabrotica* spp., Diloboderus abderus, *Epilachna* spp., *Eremnus* spp., Heteronychus arator, Hypothenemus hampei, Lagria vilosa, Leptinotarsa decemLineata, *Lissorhoptrus* spp., *Liogenys* spp, *Maecolaspis* spp, Maladera castanea, *Megascelis* spp, Melighetes aeneus, *Melolontha* spp., Myochrous armatus, *Orycaephilus* spp., *Otiorhynchus* spp., *Phyllophaga* spp., *Phlyctinus* spp., *Popillia* spp., *Psylliodes* spp., Rhyssomatus aubtilis, *Rhizopertha* spp., *Scarabeidae, Sitophilus* spp., *Sitotroga* spp., *Somaticus* spp., *Sphenophorus* spp, Sternechus subsignatus, *Tenebrio* spp., *Tribolium* spp. and *Trogoderma* spp.;

from the order Diptera, for example, *Aedes* spp., *Anopheles* spp, Antherigona soccata, Bactrocea oleae, Bibio hortulanus, *Bradysia* spp, Calliphora erythrocephala, *Ceratitis* spp., *Chrysomyia* spp., *Culex* spp., *Cuterebra* spp., *Dacus* spp., *Delia* spp, Drosophila melanogaster, *Fannia* spp., *Gastrophilus* spp., Geomyza tripunctata, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., Oscinella frit, Pegomyia hyoscyami, *Phorbia* spp., *Rhagoletis* spp., Rivelia quadrifasciata, *Scatella* spp, *Sciara* spp., *Stomoxys* spp., *Tabanus* spp., *Tannia* spp. and *Tipula* spp.;

from the order Hemiptera, for example, Acanthocoris scabrator, *Acrosternum* spp, Adelphocoris lineolatus, Amblypelta nitida, Bathycoelia thalassina, *Blissus* spp, *Cimex* spp., Clavigralla tomentosicollis, *Creontiades* spp, Distantiella theobroma, Dichelops furcatus, *Dysdercus* spp., *Edessa* spp, *Euchistus* spp., Eurydema pulchrum, *Eurygaster* spp., Halyomorpha halys, Horcias nobilellus, *Leptocorisa* spp., *Lygus* spp, *Margarodes* spp, Murgantia histrionic, *Neomegalotomus* spp, Nesidiocoris tenuis, *Nezara* spp., Nysius simulans, Oebalus insularis, *Piesma* spp., *Piezodorus* spp, *Rhodnius* spp., Sahlbergella singularis, Scaptocoris castanea, *Scotinophara* spp, *Thyanta* spp, *Triatoma* spp., and Vatiga illudens;

from the order homoptera, for example, Acyrthosium pisum, *Adalges* spp, Agalliana ensigera, Agonoscena targionii, *Aleurodicus* spp, *Aleurocanthus* spp, Aleurolobus barodensis, Aleurothrixus floccosus, Aleyrodes brassicae, Amarasca biguttula, Amritodus atkinsoni, *Aonidiella* spp., Aonidiella auranti, Aphididae, *Aphis* spp., *Aspidiotus* spp., Aulacorthum solani, Bactericera cockerelli, *Bemisia* spp, *Brachycaudus* spp, Brevicoryne brassicae, *Cacopsylla* spp, Cavariella aegopodii Scop., *Ceroplaster* spp., Chrysomphalus aonidium, Chrysomphalus dictyospermi, *Cicadella* spp, Cofana spectra, *Cryptomyzus* spp, *Cicadulina* spp, Coccus hesperidum, Dalbulus maidis, *Dialeurodes* spp, Diaphorina citri, Diuraphis noxia, *Dysaphis* spp, *Empoasca* spp., Eriosoma larigerum, *Erythroneura* spp., *Gascardia* spp., Glycaspis brimblecombei, Hyadaphis pseudobrassicae, *Hyalopterus* spp., Hyperomyzus pallidus, Idioscopus clypealis, Jacobiasca lybica, *Laodelphax* spp., Lecanium corni, *Lepidosaphes* spp., Lopaphis erysimi, Lyogenys maidis, *Macrosiphum* spp., *Mahanarva* spp, Metcalfa pruinosa, Metopolophium dirhodum, Myndus crudus, *Myzus* spp., *Neotoxoptera* sp, *Nephotettix* spp., *Nilaparvata* spp., Nippolachnus piri Mats, Odonaspis ruthae, Oregma lanigera Zehnter, Parabemisia myricae, Paratrioza cockerelli, *Parlatoria* spp., *Pemphigus* spp., Peregrinus maidis, *Perkinsiella* spp, Phorodon humuli, *Phylloxera* spp, *Planococcus* spp., *Pseudaulacaspis* spp., *Pseudococcus* spp., Pseudatomoscelis seriatus, *Psylla* spp., Pulvinaria aethiopica, *Quadraspidiotus* spp., Quesada gigas, Recilia dorsalis, *Rhopalosiphum* spp., *Saissetia* spp., *Scaphoideus* spp., *Schizaphis* spp., *Sitobion* spp., Sogatella furcifera, Spissistilus festinus, Tarophagus Proserpina, *Toxoptera* spp., *Trialeurodes* spp., Tridiscus sporoboli, *Trionymus* spp, Trioza erytreae, Unaspis citri, Zygina flammigera, and Zyginidia scutellaris;

from the order Hymenoptera, for example, Acromyrmex, *Arge* spp, *Atta* spp., *Cephus* spp., *Diprion* spp., Diprionidae, Gilpinia polytoma, *Hoplocampa* spp., *Lasius* spp., Monomorium pharaonis, *Neodiprion* spp., *Pogonomyrmex* spp, Slenopsis invicta, *Solenopsis* spp. and *Vespa* spp.;

from the order Isoptera, for example, *Coptotermes* spp., Corniternes cumulans, *Incisitermes* spp, *Macrotermes* spp, *Mastotermes* spp, *Microtermes* spp, *Reticulitermes* spp.; Solenopsis geminate;

from the order Lepidoptera, for example, *Acleris* spp., *Adoxophyes* spp., *Aegeria* spp., *Agrotis* spp., Alabama argillaceae, *Amylois* spp., Anticarsia gemmatalis, *Archips* spp., *Argyresthia* spp, *Argyrotaenia* spp., *Autographa* spp., Bucculatrix thurberiella, Busseola fusca, Cadra cautella, Carposina nipponensis, *Chilo* spp., *Choristoneura* spp., Chrysoteuchia topiaria, Clysia ambiguella, *Cnaphalocrocis* spp., *Cnephasia* spp., *Cochylis* spp., *Coleophora* spp., Colias lesbia, Cosmophila flava, *Crambus* spp, Crocidolomia binotalis, Cryptophlebia leucotreta, Cydalima perspectalis, *Cydia* spp., Diaphania perspectalis, *Diatraea* spp., Diparopsis castanea, *Earias* spp., Eldana saccharina, *Ephestia* spp., *Epinotia* spp, Estigmene acrea, Etiella zinckinella, *Eucosma* spp., Eupoecilia ambiguella, *Euproctis* spp., *Euxoa* spp., Feltia jaculiferia, *Grapholita* spp., Hedya nubiferana, *Heliothis* spp., Hellula undalis, *Herpetogramma* spp, Hyphantria cunea, Keiferia lycopersicella, Lasmopalpus lignosellus, Leucoptera scitella, *Lithocollethis* spp., Lobesia botrana, Loxostege bifidalis, *Lymantria* spp., *Lyonetia* spp., *Malacosoma* spp., Mamestra brassicae, Manduca sexta, *Mythimna* spp, *Noctua* spp, *Operophtera* spp., Orniodes indica, Ostrinia nubilalis, *Pammene* spp., *Pandemis* spp., Panolis flammea, Papaipema nebris, Pectinophora gossypiela, Perileucoptera coffeella, Pseudaletia unipuncta, Phthorimaea operculella, Pieris rapae, *Pieris* spp., Plutella xylostella,

*Prays* spp., *Pseudoplusia* spp, Rachiplusia nu, Richia albicosta, *Scirpophaga* spp., *Sesamia* spp., *Sparganothis* spp., *Spodoptera* spp., Sylepta derogate, *Synanthedon* spp., *Thaumetopoea* spp., *Tortrix* spp., Trichoplusiani, Tuta absoluta, and *Yponomeuta* spp.;
from the order Mallophaga, for example, *Damalinea* spp. and *Trichodectes* spp.; from the order Orthoptera, for example, *Blatta* spp., *Blattella* spp., *Gryllotalpa* spp., Leucophaea maderae, *Locusta* spp., Neocurtilla hexadactyla, *Periplaneta* spp., *Scapteriscus* spp, and *Schistocerca* spp.;
from the order Psocoptera, for example, *Liposcelis* spp.;
from the order Siphonaptera, for example, *Ceratophyllus* spp., *Ctenocephalides* spp. and Xenopsylla cheopis;
from the order Thysanoptera, for example, Calliothrips phaseoli, *Frankliniella* spp., *Heliothrips* spp, Hercinothrips spp., *Parthenothrips* spp, Scirtothrips aurantii, Sericothrips variabilis, *Taeniothrips* spp., *Thrips* spp; and/or
from the order Thysanura, for example, Lepisma saccharina.

Examples of soil-inhabiting pests, which can damage a crop in the early stages of plant development, are:
from the order Lepidoptera, for example, *Acleris* spp., *Aegeria* spp., *Agrotis* spp., Alabama argillaceae, *Amylois* spp., *Autographa* spp., Busseola fusca, Cadra cautella, *Chilo* spp., Crocidolomia binotalis, *Diatraea* spp., Diparopsis castanea, *Elasmopalpus* spp., *Heliothis* spp., Mamestra brassicae, Phthorimaea operculella, Plutella xylostella, *Scirpophaga* spp., *Sesamia* spp., *Spodoptera* spp. and *Tortrix* spp.;
from the order Coleoptera, for example, *Agriotes* spp., *Anthonomus* spp., Atomaria linearis, Chaetocnema tibialis, *Conotrachelus* spp., *Cosmopolites* spp., *Curculio* spp., *Dermestes* spp., Diabrotica spp., *Dilopoderus* spp., *Epilachna* spp., *Eremnus* spp., *Heteronychus* spp., Lissorhoptrus spp., *Melolontha* spp., *Orycaephilus* spp., *Otiorhynchus* spp., *Phlyctinus* spp., *Popillia* spp., Psylliodes spp., *Rhizopertha* spp., Scarabeidae, *Sitotroga* spp., *Somaticus* spp., *Tanymecus* spp., Tenebrio spp., *Tribolium* spp., *Trogoderma* spp. and Zabrus spp.;
from the order Orthoptera, for example, *Gryllotalpa* spp.;
from the order Isoptera, for example, *Reticulitermes* spp.;
from the order Psocoptera, for example, *Liposcelis* spp.;
from the order Anoplura, for example, *Haematopinus* spp., *Linognathus* spp., *Pediculus* spp., *Pemphigus* spp. and *Phylloxera* spp.;
from the order Homoptera, for example, Eriosoma larigerum;
from the order Hymenoptera, for example, Acromyrmex, *Atta* spp., *Cephus* spp., *Lasius* spp., Monomorium pharaonis, *Neodiprion* spp., *Solenopsis* spp. and *Vespa* spp.;
from the order Diptera, for example, *Tipula* spp.; crucifer flea beetles (*Phyllotreta* spp.), root maggots (*Delia* spp.), cabbage seedpod weevil (*Ceutorhynchus* spp.) and aphids.

The compounds according to any one of embodiments 1 to 37 may be useful for the control of nematodes. Thus, in one embodiment, the invention also relates to a method of controlling damage to plant and parts thereof by plant parasitic nematodes (Endoparasitic-, Semiendoparasitic- and Ectoparasitic nematodes), especially plant parasitic nematodes such as root knot nematodes, Meloidogyne hapla, Meloidogyne incognita, Meloidogyne javanica, Meloidogyne arenaria and other *Meloidogyne* species; cyst-forming nematodes, Globodera rostochiensis and other *Globodera* species; Heterodera avenae, Heterodera glycines, Heterodera schachtii, Heterodera trifolii, and other *Heterodera* species; Seed gall nematodes, *Anguina* species; Stem and foliar nematodes, *Aphelenchoides* species; Sting nematodes, Eelonolaimus longicaudatus and other *Belonolaimus* species; Pine nematodes, Bursaphelenchus xylophilus and other *Bursaphelenchus* species; Ring nematodes, *Criconema* species, *Criconemella* species, *Criconemoides* species, *Mesocriconema* species; Stem and bulb nematodes, Ditylenchus destructor, Ditylenchus dipsaci and other *Ditylenchus* species; Awl nematodes, *Dolichodorus* species; Spiral nematodes, Heliocotylenchus multicinctus and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, Pratylenchus neglectus, Pratylenchus penetrans, Pratylenchus curvitatus, Pratylenchus goodeyi and other *Pratylenchus* species; Burrowing nematodes, Radopholus similis and other *Radopholus* species; Reniform nematodes, Rotylenchus robustus, Rotylenchus reniformis and other *Rotylenchus* species; *Scutellonema* species; Stubby root nematodes, Trichodorus primitivus and other *Trichodorus* species, *Paratrichodorus* species; Stunt nematodes, Tylenchorhynchus claytoni, Tylenchorhynchus dubius and other *Tylenchorhynchus* species; Citrus nematodes, *Tylenchulus* species; Dagger nematodes, *Xiphinema* species; and other plant parasitic nematode species, such as *Subanguina*., spp *Hypsoperine* spp., *Macroposthonia* spp., *Melinius* spp., *Punctodera* spp., and *Quinisulcius* spp.

In particular, the nematode species *Meloidogyne* spp., *Heterodera* spp., *Rotylenchus* spp. and *Pratylenchus* spp. can be controlled by the compounds according to any one of embodiment 1 to 37. The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

Thus, in one embodiment 38, there is also provided a method for controlling pests (such as mosquitoes and other disease vectors). In embodiment 39, the method for controlling pests comprises applying the compositions according to any one of embodiments 1 to 37 to the pests or their environment, to their locus, for example the soil or to a surface or substrate by brushing, rolling, spraying, spreading or dipping. By way of example, an IRS (indoor residual spraying) application of a surface such as a wall, ceiling or floor surface is contemplated by the method of the invention. In an embodiment 40, it is contemplated to apply such compositions to a substrate such as non-woven or a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, US 5631072, WO 2005/64072, WO2006/128870, EP 1724392, WO2005113886 or WO 2007/090739.

In embodiment 41, the invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one compound according to any one of embodiments 1 to 37 and which are to be selected to suit the intended aims and the prevailing circumstances.

Thus, in embodiment 42, the invention therefore relates to a pesticidal composition, which comprises at least one compound according to any one of embodiments 1 to 37 as active ingredient and at least one auxiliary.

Hence, in embodiment 43, the method for controlling such pests comprises applying a pesticidally effective amount of a composition according to embodiment 42 to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment 44, it is contemplated to apply a composition according to embodiment 42 for residual control of pests on a substrate such as a fabric material in the form of (or which can be used in the manufacture of) netting, clothing, bedding, curtains and tents.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants). Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorptive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quaternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art. In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.
Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

The activity of compositions comprising compounds according to the invention can be broadened considerably, and adapted to prevailing circumstances, by including other active substances. The active substances can be of chemical or biological in type, and in the case of biological could be further modified from the biological species derived in nature. Active substances include substances that control, repel or attract pests that damage or harm useful plants in general, but also substances that improve the growth of a useful plant, such as plant growth regulators, and substances that improve the performance of the active substance, such as synergists. Examples are insecticides, acaricides, nematicides, molluscicides, aligicides, virusicides, rodenticide, bactericides, fungicides, chemosterilants, anthelmintics. Examples of a biological active substance include baculovirus, plant extract, and bacteria.

The mixtures of the compounds according to any one of embodiments 1 to 37 with other active substances may also have further surprising advantages which can also be described, in a wider sense, as synergistic activity. For example, better tolerance by plants, reduced phytotoxicity, insects can be controlled in their different development stages, or better behaviour relating to production, for example grinding or mixing, storage or use.

Individual active substances can occur in more than one group or class, and at more than one place within a group or class: information about the active substances, their spectrum, sources and classifications can be found from Compendium of Pesticide Common Names or from the Pesticide Manual created by the British Crop Production Counci.

Preferred mixtures are indicated below where a compound according to any one of embodiment 1 to 37 is indicated as "I".

Compositions comprising an adjuvant include I+compounds selected from the group of substances consisting of petroleum oils;

Compositions comprising an acaricide include I+1,1-bis(4-chlorophenyl)-2-ethoxyethanol, I+2,4-dichlorophenyl benzenesulfonate, I+2-fluoro-N-methyl-N-1-naphthylacetamide, I+4-chlorophenyl phenyl sulfone, I+abamectin, I+acequinocyl, I+acetoprole, I+acrinathrin, I+aldicarb, I+aldoxycarb, I+alpha-cypermethrin, I+amidithion, I+amidoflumet, I+amidothioate, I+amiton, I+amiton hydrogen oxalate, I+amitraz, I+aramite, I+arsenous oxide, I+AVI 382, I+AZ 60541, I+azinphos-ethyl, I+azinphos-methyl, I+azobenzene, I+azocyclotin, I+azothoate, I+benomyl, I+benoxafos, I+benzoximate, I+benzyl benzoate, I+bifenazate, I+bifenthrin, I+binapacryl, I+brofenvalerate, I+bromocyclen, I+bromophos, I+bromophos-ethyl, I+bromopropylate, I+buprofezin, I+butocarboxim, I+butoxycarboxim, I+butylpyridaben, I+calcium polysulfide, I+camphechlor, I+carbanolate, I+carbaryl, I+carbofuran, I+carbophenothion, I+CGA 50'439, I+chinomethionat, I+chlorbenside, I+chlordimeform, I+chlordimeform hydrochloride, I+chlorfenapyr, I+chlorfenethol, I+chlorfenson, I+chlorfensulfide, I+chlorfenvinphos, I+chlorobenzilate, I+chloromebuform, I+chloromethiuron, I+chloropropylate, I+chlorpyrifos, I+chlorpyrifos-methyl, I+chlorthiophos, I+cinerin I, I+cinerin II, I+cinerins, I+clofentezine, I+closantel, I+coumaphos, I+crotamiton, I+crotoxyphos, I+cufraneb, I+cyanthoate, I+cyflumetofen, I+cyhalothrin, I+cyhexatin, I+cypermethrin, I+DCPM, I+DDT, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulfon, I+diafenthiuron, I+dialifos, I+diazinon, I+dichlofluanid, I+dichlorvos, I+dicliphos, I+dicofol, I+dicrotophos, I+dienochlor, I+dimefox, I+dimethoate, I+dinactin, I+dinex, I+dinex-diclexine, I+dinobuton, I+dinocap, I+dinocap-4, I+dinocap-6, I+dinocton, I+dinopenton, I+dinosulfon, I+dinoterbon, I+dioxathion, I+diphenyl sulfone, I+disulfiram, I+disulfoton, I+DNOC, I+dofenapyn, I+doramectin, I+endosulfan, I+endothion, I+EPN, I+eprinomectin, I+ethion, I+ethoate-methyl, I+etoxazole, I+etrimfos, I+fenazaflor, I+fenazaquin, I+fenbutatin oxide, I+fenothiocarb, I+fenpropathrin, I+fenpyrad, I+fenpyroximate, I+fenson, I+fentrifanil, I+fenvalerate, I+fipronil, I+fluacrypyrim, I+fluazuron, I+flubenzimine, I+flucycloxuron, I+flucythrinate, I+fluenetil, I+flufenoxuron, I+flumethrin, I+fluorbenside, I+fluvalinate, I+FMC 1137, I+formetanate, I+formetanate hydrochloride, I+formothion, I+formparanate, I+gamma-HCH, I+glyodin, I+halfenprox, I+heptenophos, I+hexadecyl cyclopropanecarboxylate, I+hexythiazox, I+iodomethane, I+isocarbophos, I+isopropyl O-(methoxyaminothiophosphoryl)salicylate, I+ivermectin, I+jasmolin I, I+jasmolin II, I+jodfenphos, I+lindane, I+lufenuron, I+malathion, I+malonoben, I+mecarbam, I+mephosfolan, I+mesulfen, I+methacrifos, I+methamidophos, I+methidathion, I+methiocarb, I+methomyl, I+methyl bromide, I+metolcarb, I+mevinphos, I+mexacarbate, I+milbemectin, I+milbemycin oxime, I+mipafox, I+monocrotophos, I+morphothion, I+moxidectin, I+naled, I+NC-184, I+NC-512, I+nifluridide, I+nikkomycins, I+nitrilacarb, I+nitrilacarb 1:1 zinc chloride complex, I+NNI-0101, I+NNI-0250, I+omethoate, I+oxamyl, I+oxydeprofos, I+oxydisulfoton, I+pp'-DDT, I+parathion, I+permethrin, I+petroleum oils, I+phenkapton, I+phenthoate, I+phorate, I+phosalone, I+phosfolan, I+phosmet, I+phosphamidon, I+phoxim, I+pirimiphos-methyl, I+polychloroterpenes, I+polynactins, I+proclonol, I+profenofos, I+promacyl, I+propargite, I+propetamphos, I+propoxur, I+prothidathion, I+prothoate, I+pyrethrin I, I+pyrethrin II, I+pyrethrins, I+pyridaben, I+pyridaphenthion, I+pyrimidifen, I+pyrimitate, I+quinalphos, I+quintiofos, I+R-1492, I+RA-17, I+rotenone, I+schradan, I+sebufos, I+selamectin, I+SI-0009, I+sophamide, I+spirodiclofen, I+spiromesifen, I+SSI-121, I+sulfiram, I+sulfluramid, I+sulfotep, I+sulfur, I+SZI-121, I+tau-fluvalinate, I+tebufenpyrad, I+TEPP, I+terbam, I+tetrachlorvinphos, I+tetradifon, I+tetranactin, I+tetrasul, I+thiafenox, I+thiocarboxime, I+thiofanox, I+thiometon, I+thioquinox, I+thuringiensin, I+triamiphos, I+triarathene, I+triazophos, I+triazuron, I+trichlorfon, I+trifenofos, I+trinactin, I+vamidothion, I+vaniliprole and I+YI-5302;

Compositions comprising an anthelmintic include I+abamectin, I+crufomate, I+doramectin, I+emamectin, I+emamectin benzoate, I+eprinomectin, I+ivermectin, I+milbemycin oxime, I+moxidectin, I+piperazine, I+selamectin, I+spinosad and I+thiophanate;

Compositions comprising an avicide include I+chloralose, I+endrin, I+fenthion, I+pyridin-4-amine and I+strychnine;

Compositions comprising a biological control agent include I+Adoxophyes orana GV, I+Agrobacterium radiobacter, I+*Amblyseius* spp., I+Anagrapha falcifera NPV, I+Anagrus atomus, I+Aphelinus abdominalis, I+Aphidius colemani, I+Aphidoletes aphidimyza, I+Autographa californica NPV, I+Bacillus firmus, I+Bacillus sphaericus Neide, I+Bacillus thuringiensis Berliner, I+*Bacillus thuringiensis* subsp. aizawai, I+*Bacillus thuringiensis* subsp. israelensis, I+*Bacillus thuringiensis* subsp. japonensis, I+*Bacillus thuringiensis* subsp. kurstaki, I+*Bacillus thuringiensis* subsp. tenebrionis, I+Beauveria bassiana, I+Beauveria brongniartii, I+Chrysoperla carnea, I+Cryptolaemus montrouzieri, I+Cydia pomonella GV, I+Dacnusa sibirica, I+Diglyphus isaea, I+Encarsia formosa, I+Eretmocerus eremicus, I+Helicoverpa zea NPV, I+Heterorhabditis bacteriophora and H. megidis, I+Hippodamia convergens, I+Leptomastix dactylopii, I+Macrolophus caliginosus, I+Mamestra brassicae NPV, I+Metaphycus helvolus, I+Metarhizium anisopliae var. acridum, I+Metarhizium anisopliae var. anisopliae, I+Neodiprion sertifer NPV and N. lecontei NPV, I+*Orius* spp., I+Paecilomyces fumosoroseus, I+Phytoseiulus persimilis, I+Spodoptera exigua multicapsid nuclear polyhedrosis virus, I+Steinernema bibionis, I+Steinernema carpocapsae, I+Steinernema feltiae, I+Steinernema glaseri, I+Steinernema riobrave, I+Steinernema riobravis, I+Steinernema scapterisci, I+*Steinernema* spp., I+*Trichogramma* spp., I+Typhlodromus occidentalis and I+*Verticillium lecanii;*

Compositions comprising a soil sterilant include I+iodomethane and methyl bromide;

Compositions comprising a chemosterilant include I+apholate, I+bisazir, I+busulfan, I+diflubenzuron, I+dimatif, I+hemel, I+hempa, I+metepa, I+methiotepa, I+methyl apholate, I+morzid, I+penfluron, I+tepa, I+thiohempa, I+thiotepa, I+tretamine and I+uredepa;

Compositions comprising an insect pheromone include I+(E)-dec-5-en-1-yl acetate with (E)-dec-5-en-1-ol, I+(E)-tridec-4-en-1-yl acetate, I+(E)-6-methylhept-2-en-4-ol, I+(E,Z)-tetradeca-4,10-dien-1-yl acetate, I+(Z)-dodec-7-en-1-yl acetate, I+(Z)-hexadec-11-enal, I+(Z)-hexadec-11-en-1-yl acetate, I+(Z)-hexadec-13-en-11-yn-1-yl acetate, I+(Z)-icos-13-en-10-one, I+(Z)-tetradec-7-en-1-al, I+(Z)-tetradec-9-en-1-ol, I+(Z)-tetradec-9-en-1-yl acetate, I+(7E,9Z)-dodeca-7,9-dien-1-yl acetate, I+(9Z,11E)-tetradeca-9,11-dien-1-yl acetate, I+(9Z,12E)-tetradeca-9,12-dien-1-yl acetate, I+14-methyloctadec-1-ene, I+4-methylnonan-5-ol with 4-methylnonan-5-one, I+alpha-multistriatin, I+brevicomin, I+codlelure, I+codlemone, I+cuelure, I+disparlure, I+dodec-8-en-1-yl acetate, I+dodec-9-en-1-yl acetate, I+dodeca-8, I+10-dien-1-yl acetate, I+dominicalure, I+ethyl 4-methyloctanoate, I+eugenol, I+frontalin, I+gossyplure, I+grandlure, I+grandlure I, I+grandlure II, I+grandlure III, I+grandlure IV, I+hexalure, I+ipsdienol, I+ipsenol, I+japonilure, I+lineatin, I+litlure, I+looplure, I+medlure, I+megatomoic acid, I+methyl eugenol, I+muscalure, I+octadeca-2,13-dien-1-yl acetate, I+octadeca-3,13-dien-1-yl acetate, I+orfralure, I+oryctalure, I+ostramone, I+sig lure, I+sordidin, I+sulcatol, I+tetradec-11-en-1-yl acetate, I+trimedlure, I+trimedlure A, I+trimedlure B1, I+trimedlure B2, I+trimedlure C and I+trunc-call; Compositions comprising an insect repellent include I+2-(octylthio)ethanol, I+butopyronoxyl, I+butoxy(polypropylene glycol), I+dibutyl adipate, I+dibutyl phthalate, I+dibutyl succinate, I+diethyltoluamide, I+dimethyl carbate, I+dimethyl phthalate, I+ethyl hexanediol, I+hexamide, I+methoquin-butyl, I+methylneodecanamide, I+oxamate and I+picaridin;

Compositions comprising an insecticide include I+1-dichloro-1-nitroethane, I+1,1-dichloro-2,2-bis(4-ethylphenyl) ethane, I+, I+1,2-dichloropropane, I+1,2-dichloropropane with 1,3-dichloropropene, I+1-bromo-2-chloroethane, I+2,2,2-trichloro-1-(3,4-dichlorophenyl)ethyl acetate, I+2,2-dichlorovinyl 2-ethylsulfinylethyl methyl phosphate, I+2-(1,3-dithiolan-2-yl)phenyl dimethylcarbamate, I+2-(2-butoxyethoxy)ethyl thiocyanate, I+2-(4,5-dimethyl-1,3-dioxolan-2-yl)phenyl methylcarbamate, I+2-(4-chloro-3,5-xylyloxy)ethanol, I+2-chlorovinyl diethyl phosphate, I+2-imidazolidone, I+2-isovalerylindan-1,3-dione, I+2-methyl (prop-2-ynyl)aminophenyl methylcarbamate, I+2-thiocyanatoethyl laurate, I+3-bromo-1-chloroprop-1-ene, I+3-methyl-1-phenylpyrazol-5-yl dimethylcarbamate, I+4-methyl(prop-2-ynyl)amino-3,5-xylyl methylcarbamate, I+5,5-dimethyl-3-oxocyclohex-1-enyl dimethylcarbamate, I+abamectin, I+acephate, I+acetamiprid, I+acethion, I+acetoprole, I+acrinathrin, I+acrylonitrile, I+alanycarb, I+aldicarb, I+aldoxycarb, I+aldrin, I+allethrin, I+allosamidin, I+allyxycarb, I+alpha-cypermethrin, I+alpha-ecdysone, I+aluminium phosphide, I+amidithion, I+amidothioate, I+aminocarb, I+amiton, I+amiton hydrogen oxalate, I+amitraz, I+anabasine, I+athidathion, I+AVI 382, I+AZ 60541, I+azadirachtin, I+azamethiphos, I+azinphos-ethyl, I+azinphos-methyl, I+azothoate, I+Bacillus thuringiensis delta endotoxins, I+barium hexafluorosilicate, I+barium polysulfide, I+barthrin, I+Bayer 22/190, I+Bayer 22408, I+bendiocarb, I+benfuracarb, I+bensultap, I+beta-cyfluthrin, I+beta-cypermethrin, I+bifenthrin, I+bioallethrin, I+bioallethrin S-cyclopentenyl isomer, I+bioethanomethrin, I+biopermethrin, I+bioresmethrin, I+bis(2-chloroethyl) ether, I+bistrifluron, I+borax, I+brofenvalerate, I+bromfenvinfos, I+bromocyclen, I+bromo-DDT, I+bromophos, I+bromophos-ethyl, I+bufencarb, I+buprofezin, I+butacarb, I+butathiofos, I+butocarboxim, I+butonate, I+butoxycarboxim, I+butylpyridaben, I+cadusafos, I+calcium arsenate, I+calcium cyanide, I+calcium polysulfide, I+camphechlor, I+carbanolate, I+carbaryl, I+carbofuran, I+carbon disulfide, I+carbon tetrachloride, I+carbophenothion, I+carbosulfan, I+cartap, I+cartap hydrochloride, I+cevadine, I+chlorbicyclen, I+chlordane, I+chlordecone, I+chlordimeform, I+chlordimeform hydrochloride, I+chlorethoxyfos, I+chlorfenapyr, I+chlorfenvinphos, I+chlorfluazuron, I+chlormephos, I+chloroform, I+chloropicrin, I+chlorphoxim, I+chlorprazophos, I+chlorpyrifos, I+chlorpyrifos-methyl, I+chlorthiophos, I+chromafenozide, I+cinerin I, I+cinerin II, I+cinerins, I+cis-resmethrin, I+cismethrin, I+clocythrin, I+cloethocarb, I+closantel, I+clothianidin, I+copper acetoarsenite, I+copper arsenate, I+copper oleate, I+coumaphos, I+coumithoate, I+crotamiton, I+crotoxyphos, I+crufomate, I+cryolite, I+CS 708, I+cyanofenphos, I+cyanophos, I+cyanthoate, I+cyclethrin, I+cycloprothrin, I+cyfluthrin, I+cyhalothrin, I+cypermethrin, I+cyphenothrin, I+cyromazine, I+cythioate, I+d-limonene, I+d-tetramethrin, I+DAEP, I+dazomet, I+DDT, I+decarbofuran, I+deltamethrin, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulphon, I+diafenthiuron, I+dialifos, I+diamidafos, I+diazinon, I+dicapthon, I+dichlofenthion, I+dichlorvos, I+dicliphos, I+dicresyl, I+dicrotophos, I+dicyclanil, I+dieldrin, I+diethyl 5-methylpyrazol-3-yl phosphate, I+diflubenzuron, I+dilor, I+dimefluthrin, I+dimefox, I+dimetan, I+dimethoate, I+dimethrin, I+dimethylvinphos, I+dimetilan, I+dinex, I+dinex-diclexine, I+dinoprop, I+dinosam, I+dinoseb, I+dinotefuran, I+diofenolan, I+dioxabenzofos, I+dioxacarb, I+dioxathion, I+disulfoton, I+dithicrofos, I+DNOC, I+doramectin, I+DSP, I+ecdysterone, I+EI 1642, I+emamectin, I+emamectin benzoate, I+EMPC, I+empenthrin, I+endosulfan, I+endothion, I+endrin, I+EPBP, I+EPN, I+epofenonane, I+eprinomectin, I+esfenvalerate, I+etaphos, I+ethiofencarb, I+ethion, I+ethiprole, I+ethoate-methyl, I+ethoprophos, I+ethyl formate, I+ethyl-DDD, I+ethylene dibromide, I+ethylene dichloride, I+ethylene oxide, I+etofenprox, I+etrimfos, I+EXD, I+famphur, I+fenamiphos, I+fenazaflor, I+fenchlorphos, I+fenethacarb, I+fenfluthrin, I+fenitrothion, I+fenobucarb, I+fenoxacrim, I+fenoxycarb, I+fenpirithrin, I+fenpropathrin, I+fenpyrad, I+fensulfothion, I+fenthion, I+fenthion-ethyl, I+fenvalerate, I+fipronil, I+flonicamid, I+flubendiamide, I+flucofuron, I+flucycloxuron, I+flucythrinate, I+fluenetil, I+flufenerim, I+flufenoxuron, I+flufenprox, I+flumethrin, I+fluvalinate, I+FMC 1137, I+fonofos, I+formetanate, I+formetanate hydrochloride, I+formothion, I+formparanate, I+fosmethilan, I+fospirate, I+fosthiazate, I+fosthietan, I+furathiocarb, I+furethrin, I+gamma-cyhalothrin, I+gamma-HCH, I+guazatine, I+guazatine acetates, I+GY-81, I+halfenprox, I+halofenozide, I+HCH, I+HEOD, I+heptachlor, I+heptenophos, I+heterophos, I+hexaflumuron, I+HHDN, I+hydramethylnon, I+hydrogen cyanide, I+hydroprene, I+hyquincarb, I+imidacloprid, I+imiprothrin, I+indoxacarb, I+iodomethane, I+IPSP, I+isazofos, I+isobenzan, I+isocarbophos, I+isodrin, I+isofenphos, I+isolane, I+isoprocarb, I+isopropyl O-(methoxy-aminothiophosphoryl)salicylate, I+isoprothiolane, I+isothioate, I+isoxathion, I+ivermectin, I+jasmolin I, I+jasmolin II, I+jodfenphos, I+juvenile hormone I, I+juvenile hormone II, I+juvenile hormone III, I+kelevan, I+kinoprene, I+lambda-cyhalothrin, I+lead arsenate, I+lepimectin, I+leptophos, I+lindane, I+lirimfos, I+lufenuron, I+lythidathion, I+m-cumenyl methylcarbamate, I+magnesium phosphide, I+malathion, I+malonoben, I+mazidox, I+mecarbam, I+mecarphon, I+menazon, I+mephosfolan, I+mercurous chloride, I+mesulfenfos, I+metaflumizone, I+metam, I+metam-potassium, I+metam-sodium, I+methacrifos, I+methamidophos, I+methanesulfonyl fluoride, I+methidathion, I+methiocarb, I+methocrotophos, I+methomyl, I+methoprene, I+methoquin-butyl, I+methothrin, I+methoxychlor, I+methoxyfenozide, I+methyl bromide, I+methyl isothiocyanate, I+methylchloroform, I+methylene chloride, I+metofluthrin, I+metolcarb, I+metoxadiazone, I+mevinphos, I+mexacarbate, I+milbemectin, I+milbemycin oxime, I+mipafox, I+mirex, I+monocrotophos, I+morphothion, I+moxidectin, I+naftalofos, I+naled, I+naphthalene, I+NC-170, I+NC-184, I+nicotine, I+nicotine sulfate, I+nifluridide, I+nitenpyram, I+nithiazine, I+nitrilacarb, I+nitrilacarb 1:1 zinc chloride complex, I+NNI-0101, I+NNI-0250, I+nornicotine, I+novaluron, I+noviflumuron, I+O—5-dichloro-4-iodophenyl O-ethyl ethylphosphonothioate, I+O,O-diethyl O—4-methyl-2-oxo-2H-chromen-7-yl phosphorothioate, I+O,O-diethyl O—6-methyl-2-propylpyrimidin-4-yl phosphorothioate, I+O,O,O',O'-tetrapropyl dithiopyrophosphate, I+oleic acid, I+omethoate, I+oxamyl, I+oxydemeton-methyl, I+oxydeprofos, I+oxydisulfoton, I+pp'-DDT, I+para-dichlorobenzene, I+parathion, I+parathion-methyl, I+penfluron, I+pentachlorophenol, I+pentachlorophenyl laurate, I+permethrin, I+petroleum oils, I+PH 60-38, I+phenkapton, I+phenothrin, I+phenthoate, I+phorate+TX, I+phosalone, I+phosfolan, I+phosmet, I+phosnichlor, I+phosphamidon, I+phosphine, I+phoxim, I+phoxim-methyl, I+pirimetaphos, I+pirimicarb, I+pirimiphos-ethyl, I+pirimiphos-methyl, I+polychlorodicyclopentadiene isomers, I+polychloroterpenes, I+potassium arsenite, I+potassium thiocyanate, I+prallethrin, I+precocene I, I+precocene II, I+precocene III, I+primidophos, I+profenofos, I+profluthrin, I+promacyl, I+promecarb, I+propaphos, I+propetamphos, I+propoxur, I+prothidathion, I+prothiofos, I+prothoate, I+protrifenbute, I+pymetrozine, I+pyraclofos, I+pyrazophos, I+pyresmethrin, I+pyrethrin I, I+pyrethrin II, I+pyrethrins, I+pyridaben, I+pyridalyl, I+pyridaphenthion, I+pyrimidifen, I+pyrimitate, I+pyriproxyfen, I+quassia, I+quinalphos, I+quinalphos-methyl, I+quinothion, I+quintiofos, I+R-1492, I+rafoxanide, I+resmethrin, I+rotenone, I+RU 15525, I+RU 25475, I+ryania, I+ryanodine, I+sabadilla, I+schradan, I+sebufos, I+selamectin, I+SI-0009, I+SI-0205, I+SI-0404, I+SI-0405, I+silafluofen, I+SN 72129, I+sodium arsenite, I+sodium cyanide, I+sodium fluoride, I+sodium hexafluorosilicate, I+sodium pentachlorophenoxide, I+sodium selenate, I+sodium thiocyanate, I+sophamide, I+spinosad, I+spiromesifen, I+spirotetrmat, I+sulcofuron, I+sulcofuron-sodium, I+sulfluramid, I+sulfotep, I+sulfuryl fluoride, I+sulprofos, I+tar oils, I+tau-fluvalinate, I+tazimcarb, I+TDE, I+tebufenozide, I+tebufenpyrad, I+tebupirimfos, I+teflubenzuron, I+tefluthrin, I+temephos, I+TEPP, I+terallethrin, I+terbam, I+terbufos, I+tetrachloroethane, I+tetrachlorvinphos, I+tetramethrin, I+theta-cypermethrin, I+thiacloprid, I+thiafenox, I+thiamethoxam, I+thicrofos, I+thiocarboxime, I+thiocyclam, I+thiocyclam hydrogen oxalate, I+thiodicarb, I+thiofanox, I+thiometon, I+thionazin, I+thiosultap, I+thiosultap-sodium, I+thuringiensin, I+tolfenpyrad, I+tralomethrin, I+transfluthrin, I+transpermethrin, I+triamiphos, I+triazamate, I+triazophos, I+triazuron, I+trichlorfon, I+trichlormetaphos-3, I+trichloronat, I+trifenofos, I+triflumuron, I+trimethacarb, I+triprene, I+vamidothion, I+vaniliprole, I+veratridine, I+veratrine, I+XMC, I+xylylcarb, I+YI-5302, I+zeta-cypermethrin, I+zetamethrin, I+zinc phosphide, I+zolaprofos and ZXI 8901, I+cyantraniliprole, I+chlorantraniliprole, I+cyenopyrafen, I+cyflumetofen, I+pyrifluquinazon, I+spinetoram, I+spirotetramat, I+sulfoxaflor, I+flufiprole, I+meperfluthrin, I+tetramethylfluthrin, I+triflumezopyrim;

Compositions comprising a molluscicide include I+bis(tributyltin) oxide, I+bromoacetamide, I+calcium arsenate, I+cloethocarb, I+copper acetoarsenite, I+copper sulfate, I+fentin, I+ferric phosphate, I+metaldehyde, I+methiocarb, I+niclosamide, I+niclosamide-olamine, I+pentachlorophenol, I+sodium pentachlorophenoxide, I+tazimcarb, I+thiodicarb, I+tributyltin oxide, I+trifenmorph, I+trimethacarb, I+triphenyltin acetate and triphenyltin hydroxide, I+pyriprole; Compositions comprising a nematicide include I+AKD-3088, I+1,2-dibromo-3-chloropropane, I+1,2-dichloropropane, I+1,2-dichloropropane with 1,3-dichloropropene, I+1,3-dichloropropene, I+3,4-dichlorotetrahydrothiophene 1,1-dioxide, I+3-(4-chlorophenyl)-5-methylrhodanine, I+5-methyl-6-thioxo-1,3,5-thiadiazinan-3-ylacetic acid, I+6-isopentenylaminopurine, I+abamectin, I+acetoprole, I+alanycarb, I+aldicarb, I+aldoxycarb, I+AZ 60541, I+benclothiaz, I+benomyl, I+butylpyridaben, I+cadusafos, I+carbofuran, I+carbon disulfide, I+carbosulfan, I+chloropicrin, I+chlorpyrifos, I+cloethocarb, I+cytokinins, I+dazomet, I+DBCP, I+DCIP, I+diamidafos, I+dichlofenthion, I+dicliphos, I+dimethoate, I+doramectin, I+emamectin, I+emamectin benzoate, I+eprinomectin, I+ethoprophos, I+ethylene dibromide, I+fenamiphos, I+fenpyrad, I+fensulfothion, I+fosthiazate, I+fosthietan, I+furfural, I+GY-81, I+heterophos, I+iodomethane, I+isamidofos, I+isazofos, I+ivermectin, I+kinetin, I+mecarphon, I+metam, I+metam-potassium, I+metam-sodium, I+methyl bromide, I+methyl isothiocyanate, I+milbemycin oxime, I+moxidectin, I+Myrothecium verrucaria composition, I+NC-184, I+oxamyl, I+phorate, I+phosphamidon, I+phosphocarb, I+sebufos, I+selamectin, I+spinosad, I+terbam, I+terbufos, I+tetrachlorothiophene, I+thiafenox, I+thionazin, I+triazophos, I+triazuron, I+xylenols, I+YI-5302 and zeatin, I+fluensulfone;

Compositions comprising a synergist include I+2-(2-butoxyethoxy)ethyl piperonylate, I+benzodioxol-5-yl)-3-hexylcyclohex-2-enone, I+farnesol with nerolidol, I+MB-599, I+MGK 264, I+piperonyl butoxide, I+piprotal, I+propyl isomer, I+S421, I+sesamex, I+sesasmolin and I+sulfoxide;

Compositions comprising an animal repellent include I+anthraquinone, I+chloralose, I+copper naphthenate, I+copper oxychloride, I+diazinon, I+dicyclopentadiene, I+guazatine, I+guazatine acetates, I+methiocarb, I+pyridin-4-amine, I+thiram, I+trimethacarb, I+zinc naphthenate and I+ziram;

Further compositions include I+Brofluthrinate, I+Cycloxaprid, I+Diflovidazine, I+Flometoquin, I+Fluhexafon, I+Guadipyr, I+Plutella xylostella Granulosis virus, I+Cydia pomonella Granulosis virus, I+Harpin, I+Imicyafos, I+Heliothis virescens Nucleopolyhedrovirus, I+Heliothis punctigera Nucleopolyhedrovirus, I+Helicoverpa armigera Nucleopolyhedrovirus, I+Helicoverpa zea Nucleopolyhedrovirus, I+Spodoptera frugiperda Nucleopolyhedrovirus, I+Plutella xylostella Nucleopolyhedrovirus, I+Pasteuria nishizawae, I+p-cymene, I+Pyflubumide, I+Pyrafluprole, I+pyrethrum, I+QRD 420, I+QRD 452, I+QRD 460, I+Terpenoid blends, I+Terpenoids, I+Tetraniliprole, and I+α-terpinene;

Composition also include mixtures of compound of formula I and an active substance referenced by a code, such as I+code AE 1887196 (BSC-BX60309), I+code NNI-0745 GR, I+code IKI-3106, 1, I+code JT-L001, I+code ZNQ-08056, I+code IPPA152201, I+code HNPC-A9908 (CAS: [660411-21-2]), I+code HNPC-A2005 (CAS: [860028-12-2]), I+code JS118, I+code ZJ0967, I+code ZJ2242, I+code JS7119 (CAS: [929545-74-4]), I+code SN-1172, I+code HNPC-A9835, I+code HNPC-A9955, I+code HNPC-A3061, I+code Chuanhua 89-1, I+code IPP-10, I+code ZJ3265, I+code JS9117, I+code SYP-9080, I+code ZJ3757, I+code ZJ4042, I+code ZJ4014, I+code ITM-121, I+code DPX-RAB55 (DKI-2301), I+code Me5382, I+code NC-515, I+code NA-89, I+code MIE-1209, I+code MCI-8007, I+code BCS—CL73507, I+code S—1871, I+code DPX-RDS63, and I+code AKD-1193.

Thus, in one embodiment 44, the active ingredient mixture of the compounds according to any one of embodiments 1 to 37 with active ingredients described above comprises a compound according to any one of embodiments 1 to 37 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

In embodiment 45, the mixtures as described above can be used in a method for controlling pests, which comprises applying a composition comprising a mixture as described above to the pests or their environment, with the exception of a method for treatment of the human or animal body by surgery or therapy and diagnostic methods practiced on the human or animal body.

The mixtures comprising a compound according to any one of embodiments 1 to 37 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds according to any one of embodiments 1 to 37 and the active ingredients as described above is not essential for working the present invention.

The compositions according to embodiment 44 can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to embodiment 44 are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds according to any one of embodiments 1 to 37 and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

In embodiment 46, the invention therefore relates to a method for the protection of plant propagation material from the attack by pests, which comprises treating the propagation material or the site, where the propagation material is planted, with a compound according to any one of embodiments 1 to 37 or with a composition according to embodiment 42 or 44, which comprises at least one compound according to any one of embodiments 1 to 37, as active ingredient and at least one auxiliary composition.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound according to any one of embodiments 1 to 37.

Seed treatment comprises all suitable seed treatment techniques known in the art, such as seed dressing, seed coating, seed dusting, seed soaking and seed pelleting. The seed treatment application of the compound according to any one of embodiments 1 to 37 can be carried out by any known methods, such as spraying or by dusting the seeds before sowing or during the sowing/planting of the seeds.

EXPERIMENTAL

Preparatory Examples

The following examples are intended to illustrate the invention and are not to be construed as being limitations thereon. "Mp" means melting point in ° C. $^1$H NMR measurements were recorded on a Brucker 400 MHz spectrometer, chemical shifts are given in ppm relevant to a TMS standard. Spectra measured in deuterated solvents as indicated.

LC MS Method A: Standard

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

LC MS Method B: Standard Long

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85.

LC MS Method C: Unpolar

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 40% B, 60% A; 1.2-1.5 min 100% B; Flow (ml/min) 0.85.

MS Method D

The mass spectra were obtained on a Finnigan LCQ-DUO spectrometer using electrospray ionization.

UPLC-MS Method E

Mass Spectrometer: Acquity SDS Mass Spectrometer from Waters
HPLC: UPLC 'H' class
Optimized Mass Parameter:
Ionisation method: Electrospray (ESI). Polarity: Positive and Negative Polarity Switch. Scan Type: Full Scan. Capillary (kV): 3.00. Cone Voltage (V): 41.00. Source Temperature (° C.): 150.
Desolvation Gas Flow (L/Hr): 1000. Desolvation Temperature (° C.): 500. Gas Flow@Cone (L/Hr): 50. Mass range: 110 to 800 Da. PDA Wavelength range: 210 to 400 nm.
Optimized Chromatographic parameter:—
Gradient conditions:
Solvent A: Water with 0.1% formic acid:Acetonitrile: 95:5 v/v
Solvent B: Acetonitrile with 0.05% formic acid

| Time (minutes) | A (%) | B (%) | Flow rate (ml/min) |
| --- | --- | --- | --- |
| 0 | 90 | 10 | 0.8 |
| 0.2 | 50 | 50 | 0.8 |
| 0.7 | 0 | 100 | 0.8 |
| 1.3 | 0 | 100 | 0.8 |
| 1.4 | 90 | 10 | 0.8 |
| 1.6 | 90 | 10 | 0.8 |

Column: Acquity UPLC HSS T3 C18
Column length: 30 mm. Internal diameter of column: 2.1 mm. Particle Size: 1.8 μm. Column oven temperature: 40° C.

LC-MS Method F

Mass Spectrometer: 6410 Triple Quadruple Mass Spectrometer from Agilent Technologies
HPLC: Agilent 1200 Series HPLC
Optimized Mass Parameter:
Ionisation method: Electrospray (ESI). Polarity: Positive and Negative Polarity Switch. Scan Type: MS2 Scan. Capillary (kV): 4.00. Fragmentor (V): 100.00. Gas Temperature (° C.): 350. Gas Flow (L/min): 11. Nebulizer Gas (psi): 45. Mass range: 110 to 1000 Da. DAD Wavelength range: 210 to 400 nm.

Optimized Chromatographic Parameter:
Gradient conditions:
Solvent A: Water with 0.1% formic acid:Acetonitrile: 95:5 v/v
Solvent B: Acetonitrile with 0.1% formic acid

| Time (minutes) | A (%) | B (%) | Flow rate (ml/min) |
|---|---|---|---|
| 0 | 90 | 10 | 1.8 |
| 0.9 | 0 | 100 | 1.8 |
| 1.8 | 0 | 100 | 1.8 |
| 2.2 | 90 | 10 | 1.8 |
| 2.5 | 90 | 10 | 1.8 |

Column: KINETEX EVO C18
Column length: 50 mm. Internal diameter of column: 4.6 mm. Particle Size: 2.6 μm. Column oven temperature: 40° C.

Example 1: Preparation of 1-(2-isopropylphenyl)-3-[6-[1-[4-(trifluoromethoxy)phenyl]-1,2,4-triazol-3-yl]-2-quinolyl]thiourea (Compound P1.4)

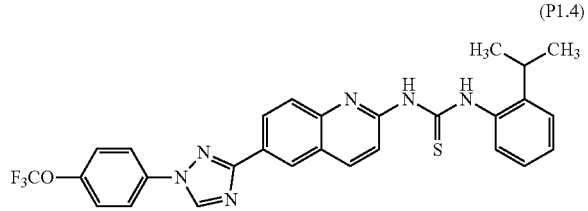 [SMILES: CC(C)c1ccccc1NC(=S)Nc1ccc2cc(-c3ncn(-c4ccc(OC(F)(F)F)cc4)n3)ccc2n1]

(P1.4)

Step A-1: Preparation of 2-oxo-1H-quinoline-6-carbonitrile

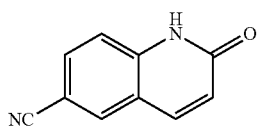 [SMILES: N#Cc1ccc2[nH]c(=O)ccc2c1]

To a solution of 6-bromo-1H-quinolin-2-one (20.0 g, 89.0 mmol) in NMP (80 mL) was added CuCN (12.8 g, 142 mmol) followed by heating the reaction mixture at 150° C. for 16 h. The reaction mixture was cooled to room temperature, poured on to crushed ice, resulted solids filtered, and dried under vacuum to afford 2-oxo-1H-quinoline-6-carbonitrile (15.0 g) as brown solid.

$^1$H NMR (300 MHz, DMSO-d$_6$): δ 12.15 (s, 1H), 8.24 (s, 1H), 7.91 (d, 2H), 7.41 (s, 1H), 6.63 (s, 1H).
MS (method D) m/z: 171.1 [M+H]$^+$.

Step A-2: Preparation of 2-chloroquinoline-6-carbonitrile

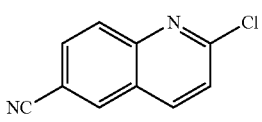

A suspension of 2-oxo-1H-quinoline-6-carbonitrile (15.0 g, 88.0 mmol) in POCl$_3$ (130 mL) was heated at 120° C. for 16 h. The reaction mixture was cooled to room temperature, poured on to crushed ice, resulted solids filtered and dried under vacuum to afford 2-chloroquinoline-6-carbonitrile (14.0 g) as brown solid.

$^1$H NMR (300 MHz, DMSO-d$_6$): δ 8.73 (s, 1H), 8.57 (d, 1H), 8.09-8.16 (m, 2H), 7.78 (d, 1H).
MS (method D) m/z: 189.1 [M+H]$^+$.

Step A-3: Preparation of tert-butyl N-(6-cyano-2-quinolyl)carbamate

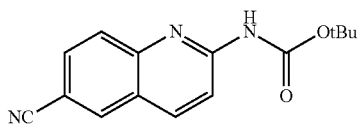 [SMILES: CC(C)(C)OC(=O)Nc1ccc2cc(C#N)ccc2n1]

A suspension of 2-chloroquinoline-6-carbonitrile (14.0 g, 75.0 mmol) in 1, 4 dioxane (230 mL) was charged with tert-butyl carbamate (9.60 g, 82.0 mmol) and NaOH (4.46 g, 116 mmol) at room temperature followed by degassing with argon for 10 min. Pd(OAc)$_2$ (0.50 g, 0.75 mmol) and Xanthphos (0.86 g, 1.48 mmol) were added to the reaction mixture and heated at 100° C. for 16 h. The reaction mixture was cooled to room temperature, filtered through celite bed, and the filtrate was concentrated under reduced pressure. The residue was purified by column chromatography to afford tert-butyl N-(6-cyano-2-quinolyl)carbamate (10.0 g) as an off white solid.

$^1$H NMR (300 MHz, CDCl$_3$): δ 8.26 (d, 1H), 8.13-8.18 (m, 2H), 8.04 (s, 1H), 7.84 (d, 1H), 7.78 (d, 1H), 7.75 (d, 1H), 1.51 (s, 9H).
MS (method D) m/z: 270.1 [M+H]$^+$.

Step A-4: Preparation of tert-butyl N-(6-carbamoyl-2-quinolyl)carbamate

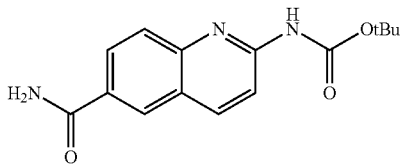 [SMILES: CC(C)(C)OC(=O)Nc1ccc2cc(C(N)=O)ccc2n1]

A solution of tert-butyl N-(6-cyano-2-quinolyl)carbamate (7.00 g, 26.0 mmol) in DMSO (70 mL) was charged with K$_2$CO$_3$ (3.50 g) followed by H$_2$O$_2$ (21.0 mL) dropwise at 0° C. over 10 min. The reaction mixture was heated to room temperature and stirred for 2 h. The reaction mixture was cooled to 0° C., quenched with ice cold water (400 mL), resulted solids were filtered and dried under vacuum to afford tert-butyl N-(6-carbamoyl-2-quinolyl)carbamate (7.10 g) as an off white solid.

$^1$H NMR (300 MHz, DMSO-d$_6$): δ 10.26 (s, 1H), 8.43 (d, 1H), 8.35 (d, 1H), 8.09-8.13 (m, 1H), 7.77 (d, 1H), 7.47 (s, 1H),
MS (method D) m/z: 288.1 [M+H]$^+$.

Step A-5: Preparation of tert-butyl N-[6-[(E)-dimethylaminomethylenecarbamoyl]-2-quinolyl]carbamate

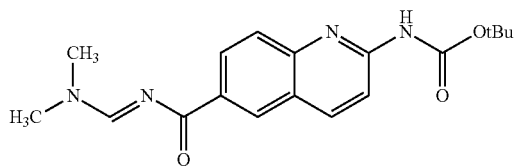 [SMILES: CN(C)/C=N/C(=O)c1ccc2nc(NC(=O)OC(C)(C)C)ccc2c1]

A suspension of tert-butyl N-(6-carbamoyl-2-quinolyl)carbamate (7.10 g, 25.0 mmol) in DMF•DMA (35 mL) was heated at 90° C. for 4 h. The reaction mixture was cooled to room temperature and concentrated under reduced pressure to afford tert-butyl N-[6-[(E)-dimethylaminomethylenecarbamoyl]-2-quinolyl]carbamate (7.50 g, crude) as an off white solid.

$^1$H NMR (300 MHz, DMSO-d$_6$): δ 10.23 (s, 1H), 8.72 (t, 2H), 8.36-8.46 (m, 2H), 8.09 (d, 1H), 7.76 (d, 1H), 3.22 (d, 6H), 1.50 (s, 9H).

MS (method D) m/z: 343.1 [M+H]$^+$.

Step A-6: Preparation of tert-butyl N-[6-(1H-1,2,4-triazol-3-yl)-2-quinolyl]carbamate

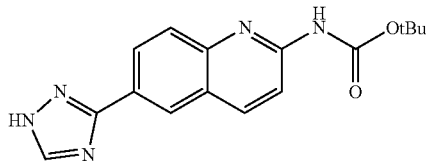 [SMILES: CC(C)(C)OC(=O)Nc1ccc2cc(-c3nc[nH]n3)ccc2n1]

A solution of tert-butyl N-[6-[(E)-dimethylaminomethylenecarbamoyl]-2-quinolyl]carbamate (7.50 g, 19.7 mmol) in acetic acid (75 mL) was charged with hydrazine hydrate (1.00 mL, 19.7 mmol) over 10 min at room temperature. The reaction mixture was heated at 80° C. for 1 h. The reaction mixture was concentrated under reduced pressure, triturated with MTBE (100 mL) and was dried under vacuum to afford to afford tert-butyl N-[6-(1H-1,2,4-triazol-3-yl)-2-quinolyl]carbamate (4.00 g) as an off-white solid.

$^1$H NMR (300 MHz, DMSO-d$_6$): δ 10.22 (s, 1H), 8.52 (d, 2H), 8.41 (d, 1H), 8.30 (dd, 1H), 8.08 (d, 1H), 7.83 (d, 1H), 1.50 (s, 9H).

MS (method D) m/z: 312.1 [M+H]$^+$.

Step A-7: Preparation of 6-[1-[4-(trifluoromethoxy)phenyl]-1,2,4-triazol-3-yl]quinolin-2-amine

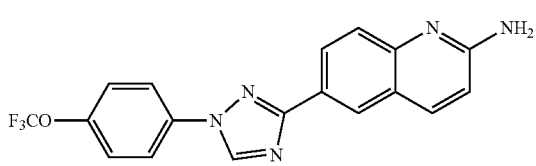 [SMILES: Nc1ccc2cc(-c3ncn(-c4ccc(OC(F)(F)F)cc4)n3)ccc2n1]

A solution of tert-butyl N-[6-(1H-1,2,4-triazol-3-yl)-2-quinolyl]carbamate (4.00 g, 12.8 mmol) in DMF: water (80 mL, 4:1) was charged with compound 1-iodo-4-(trifluoromethoxy)benzene (3.70 g, 12.8 mmol), Cs$_2$CO$_3$ (8.32 g, 25.6 mmol) and 8-hydroxy quinoline (0.43 g, 2.90 mol) and the mixture was degased with argon for 10 min. CuI (0.73 g, 3.80 mol) was added to the reaction mixture and heated at 150° C. for 16 h. The reaction mixture was cooled to room temperature, quenched with water (300 mL) and extracted with EtOAc (2×300 mL). The combined organic layers were washed with water (100 mL) and brine (100 mL), dried over anhydrous Na$_2$SO$_4$, and concentrated under reduced pressure. The residue was purified by column chromatography to afford 6-[1-[4-(trifluoromethoxy)phenyl]-1,2,4-triazol-3-yl]quinolin-2-amine (2.90 g) as an off white solid.

$^1$H NMR (300 MHz, DMSO-d$_6$): δ 9.41 (s, 1H), 8.39 (d, 1H), 8.20 (d, 1H), 8.03-8.18 (d, 3H), 7.63 (d, 2H), 7.55 (d, 1H), 6.81 (d, 1H), 6.63 (s, 1H).

MS (method D) m/z: 371.9 [M+H]$^+$.

Step A-8: Preparation of 1-(2-isopropylphenyl)-3-[6-[1-[4-(trifluoromethoxy)phenyl]-1,2,4-triazol-3-yl]-2-quinolyl]thiourea

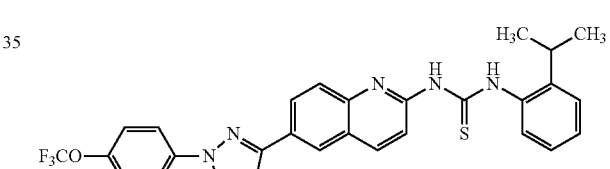

A suspension of 6-[1-[4-(trifluoromethoxy)phenyl]-1,2,4-triazol-3-yl]quinolin-2-amine (200 mg, 0.54 mmol) in THF (6.0 mL) was charged with NaH (32 mg, 0.81 mmol, 60% in mineral oil) in portions wise at 0° C. and stirred for 30 minutes. A solution of 1-isopropyl-2-isothiocyanato-benzene (477 mg, 2.69 mmol) in THF (6 mL) was added to the reaction mixture and allowed stirred at 60° C. for 16 h. The reaction mixture was cooled to 0° C., quenched with water (10 mL) and extracted with EtOAc (2×50 mL). The combined organic layers were washed with water (20 mL) and brine (20 mL), dried over anhydrous Na$_2$SO$_4$, and concentrated under reduced pressure. The residue was purified by flash column chromatography to afford 1-(2-isopropylphenyl)-3-[6-[1-[4-(trifluoromethoxy)phenyl]-1,2,4-triazol-3-yl]-2-quinolyl]thiourea (55.0 mg) as an off white solid.

$^1$H NMR (300 MHz, DMSO-d$_6$): δ 13.81 (s, 1H), 11.30 (s, 1H), 9.47 (s, 1H), 8.67 (d, 1H), 8.55 (d, 1H), 8.39 (d, 1H), 8.11 (d, 2H), 7.92 (d, 1H), 7.64 (d, H), 7.51 (d, 2H), 7.43 (d, 1H), 7.25-7.30 (m, 2H), 3.18-3.27 (m, 1H), 1.26 (d, 6H).

MS (method D) m/z: 548.9 [M+H]$^+$.

Example 2: Preparation of 1-(2-isopropylphenyl)-3-[6-[1-[4-(trifluoromethoxy)phenyl]-1,2,4-triazol-3-yl]-2-quinolyl]urea (Compound P1.3)

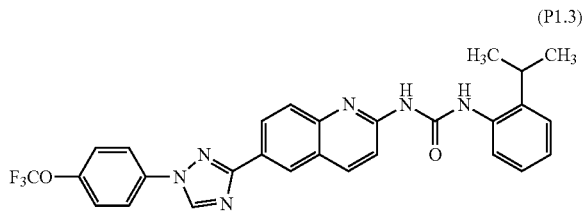 [SMILES: CC(C)c1ccccc1NC(=O)Nc1ccc2cc(-c3ncn(-c4ccc(OC(F)(F)F)cc4)n3)ccc2n1]

(P1.3)

A solution of 6-[1-[4-(trifluoromethoxy)phenyl]-1,2,4-triazol-3-yl]quinolin-2-amine (100 mg, 0.269 mmol, example 1, step A-7) in CH$_3$CN (5.0 mL) was charged with K$_2$CO$_3$ (111 mg, 0.81 mmol) and a solution of 1-isocyanato-2-isopropyl-benzene (52 mg, 0.322 mmol) in CH$_3$CN (5.0 mL). The reaction mixture was stirred at room temperature for 16 h. The resulted solids were filtered and dried under vacuum to afford 1-(2-isopropylphenyl)-3-[6-[1-[4-(trifluoromethoxy)phenyl]-1,2,4-triazol-3-yl]-2-quinolyl]urea (50 mg) as an off white solid.

$^1$H NMR (300 MHz, DMSO-d$_6$): δ 11.59 (s, 1H), 10.26 (s, 1H), 9.47 (s, 1H), 8.63 (s, 1H), 8.45-8.49 (m, 2H), 8.09-8.17 (q, 2H), 8.10 (dd, 1H), 7.86 (d, 1H), 7.64 (d, 2H), 7.39 (d, 2H), 7.12-7.27 (m, 2H), 3.50-3.54 (m, 1H), 1.34 (d, 6H).
MS (method D) m/z: 532.8 [M+H]$^+$.

Example 3: Preparation of 3-(2-isopropylphenyl)-N-[6-[1-[4-(trifluoromethoxy)phenyl]-1,2,4-triazol-3-yl]-2-quinoly]-1,3-thiazetidin-2-imine (Compound P2.1)

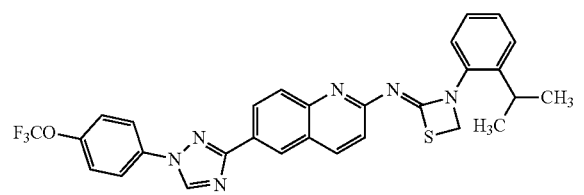

(P2.1)

A solution of 6-[1-[4-(trifluoromethoxy)phenyl]-1,2,4-triazol-3-yl]quinolin-2-amine (100 mg, 0.269 mmol, example 1, step A-7) in butan-2-one (5.0 mL) was charged with diiodomethane (0.122 g, 0.456 mmol) and K$_2$CO$_3$ (0.202 g, 1.458 mmol). The reaction mixture was stirred at 55° C. overnight. After cooling, the solution was diluted with dichloromethane. The organic phase was washed with sodium thiosulfate and brine, dried over MgSO$_4$, filtered and evaporated. The crude product was purified by column chromatography to give 3-(2-isopropylphenyl)-N-[6-[1-[4-(trifluoromethoxy)phenyl]-1,2,4-triazol-3-yl]-2-quinolyl]-1,3-thiazetidin-2-imine (60 mg) as a solid (mp: 102-3° C.).

$^1$H NMR (400 MHz, CDCl$_3$): δ 8.60 (s, 1H), 8.53 (d, 1H), 8.42 (dd, 1H), 8.06 (d, 1H), 7.96 (d, 1H), 7.82 (m, 2H), 7.35-7.42 (m, 4H), 7.35 (t, 1H), 7.22 (m, 1H), 7.10 (d, 1H), 5.01 (s, 2H), 3.33 (sept, 1H), 1.28 (d, 6H).
LC/MS (method B) m/z: 561 [M+H]$^+$, R$_t$=2.47 min.

Example 4: Preparation of 3-(2-isopropylphenyl)-4-methyl-N-[6-[1-[4-(trifluoromethoxy)phenyl]-1,2,4-triazol-3-yl]-2-quinolyl]thiazol-2-imine (Compound P2.2)

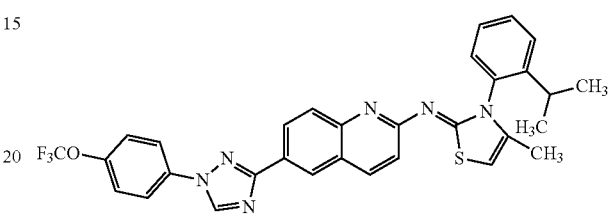

(P2.2)

A solution of 6-[1-[4-(trifluoromethoxy)phenyl]-1,2,4-triazol-3-yl]quinolin-2-amine (200 mg, 0.365 mmol, example 1, step A-7) in butan-2-one (5.0 ml) was charged with triethylamine (0.105 ml, 0.729 mmol) and chloropropan-2-one (0.036 ml, 0.456 mmol). The mixture was stirred at RT for 24 h. The solution was diluted with dichloromethane. The organic phase was washed with water, dried over MgSO$_4$, filtered and evaporated. The crude product was purified by column chromatography to give 3-(2-isopropylphenyl)-4-methyl-N-[6-[1-[4-(trifluoromethoxy)phenyl]-1,2,4-triazol-3-yl]-2-quinolyl]thiazol-2-imine (58 mg) as a solid.

$^1$H NMR (400 MHz, CDCl$_3$): δ 8.60 (s, 1H), 8.50 (s, 1H), 8.41 (dd, 1H), 8.08 (d, 1H), 7.92 (d, 1H), 7.85 (d, 2H), 7.51 (m, 2H), 7.35-7.45 (m, 3H), 7.17 (t, 1H), 7.00 (d, 1H), 6.21 (s, 1H), 2.59 (sept, 1H), 1.21 and 1.15 (2d, 6H), 1.14 (d, 6H).
LC/MS (method B) m/z: 587 [M+H]$^+$, R$_t$=2.26 min.

Example 5: Preparation of (2Z)-3-(2-isopropylphenyl)-2-[[6-[1-[4-(trifluoromethoxy)phenyl]-1,2,4-triazol-3-yl]-2-quinolyl]imino]thiazolidin-4-one (Compound P2.3) and (2E)-2-(2-isopropylphenyl)imino-3-[6-[1-[4-(trifluoromethoxy)phenyl]-1,2,4-triazol-3-yl]-2-quinolyl]thiazolidin-4-one (Compound P2.4)

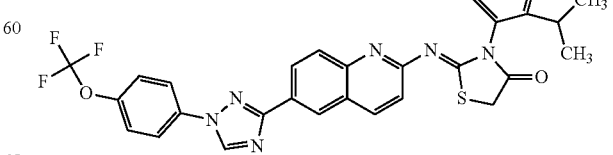

(P2.3)

-continued (P2.4)

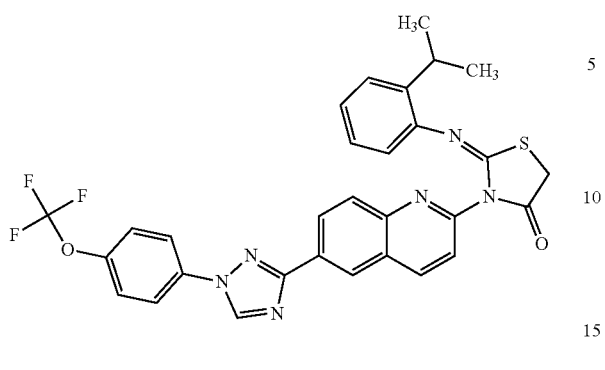

A solution of 6-[1-[4-(trifluoromethoxy)phenyl]-1,2,4-triazol-3-yl]quinolin-2-amine (200 mg, 0.365 mmol, example 1, step A-7) in butan-2-one (5.0 mL) was charged with triethylamine (0.105 ml, 0.729 mmol) and chloracetyl chloride (0.052 g, 0.456 mmol). The mixture was stirred at 60° C. for 6 h. The solution was diluted with dichloromethane. The organic phase was washed with water, dried over MgSO$_4$, filtered and evaporated. The crude mixture was purified by column chromatography to give (2Z)-3-(2-isopropylphenyl)-2-[[6-[1-[4-(trifluoromethoxy)phenyl]-1,2,4-triazol-3-yl]-2-quinolyl]imino]thiazolidin-4-one (60 mg, compound P2.3) and (2E)-2-(2-isopropylphenyl)imino-3-[6-[1-[4-(trifluoromethoxy)phenyl]-1,2,4-triazol-3-yl]-2-quinolyl]thiazolidin-4-one (35 mg, compound P2.4).

(2Z)-3-(2-isopropylphenyl)-2-[[6-[1-[4-(trifluoromethoxy)phenyl]-1,2,4-triazol-3-yl]-2-quinolyl]imino]thiazolidin-4-one (Compound P2.3)

$^1$H NMR (400 MHz, CDCl$_3$): δ 8.63 (s, 1H), 8.61 (s, 1H), 8.52 (dd, 1H), 8.10-8.14 (m, 2H), 7.85 (d, 2H), 7.51 (m, 2H), 7.43 (m, 2H), 7.38 (m, 1H), 7.20 (m, 1H), 7.14 (d, 1H), 4.03 (s, 2H), 2.87 (sept, 1H), 1.24 (m, 6H).

LC/MS (method B) m/z: 589 [M+H]$^+$, R$_t$=2.30 min.

(2E)-2-(2-isopropylphenyl)imino-3-[6-[1-[4-(trifluoromethoxy)phenyl]-1,2,4-triazol-3-yl]-2-quinolyl]thiazolidin-4-one (Compound P2.4)

$^1$H NMR (400 MHz, CDCl$_3$): δ 8.77 (s, 1H), 8.66 (s, 1H), 8.62 (dd, 1H), 8.49 (d, 1H), 8.25 (d, 1H), 7.85 (m, 2H), 7.57 (d, 1H), 7.43 (d, 2H), 7.26 (t, 1H), 7.11-7.15 (m, 2H), 6.89 (d, 1H), 4.10 (s, 2H), 2.99 (sept, 1H), 1.16 (d, 6H).

LC/MS (method B) m/z: 589 [M+H]$^+$, R$_t$=2.24 min.

Example 6: Preparation of 1-(2,6-dimethylphenyl)-3-[6-[1-[4-(trifluoromethoxy)phenyl]-1,2,4-triazol-3-yl]quinazolin-2-yl]thiourea (Component P2.5) and 1-(2,6-dimethylphenyl)-3-[6-[1-[4-(trifluoromethoxy)-phenyl]-1,2,4-triazol-3-yl]quinazolin-2-yl]urea (Component P2.6)

(P2.5)

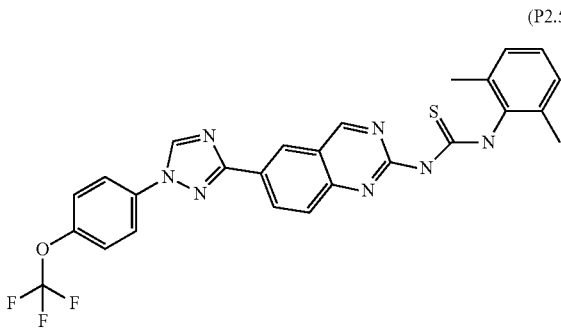

(P2.6)

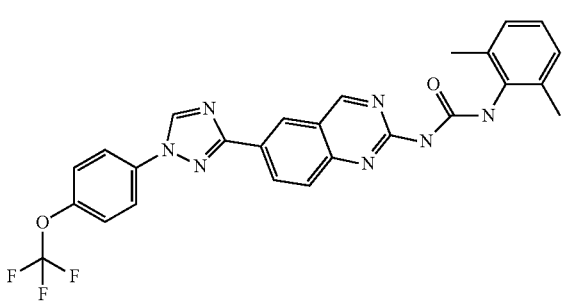

Step B-1: Preparation of 3-bromo-1-[4-(trifluoromethoxy)phenyl]-1,2,4-triazole

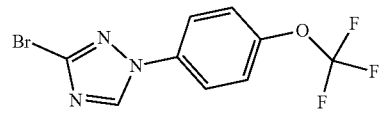 [SMILES: FC(F)(F)Oc1ccc(-n2cnc(Br)n2)cc1]

To a mixture of 1-iodo-4-(trifluoromethoxy)benzene (3 g, 10.416 mmol) in methylsulfinylmethane (24 mL) was added 3-bromo-1H-1,2,4-triazole (3.1 g) under nitrogen atmosphere followed by addition of cesium carbonate (6.7 g, 20.833 mmol) and copper iodide (0.4 g, 2.083 mmol). The reaction mass was stirred at 130° C. for 18 hours in seal tube. The reaction mass was then diluted with water and extracted with ethylacetate (3×70 mL). The combined organic layers were then dried over sodium sulphate and concentrated under reduced pressure followed by column chromatography to obtain the title compound as solid (3 g).

$^1$H NMR (400 MHz, (CD$_3$)$_3$SO): δ 9.38-9.25 (m, 1H), 7.98-7.92 (m, 2H), 7.65-7.53 (m, 2H)

LC/MS (method E) m/z: 308 [M+H]$^+$, R$_t$=0.94 min.

Step B-2: Preparation of 6-(4,4,5,5-tetramethyl-1,3,2-dioxaborolan-2-yl)quinazolin-2-amine

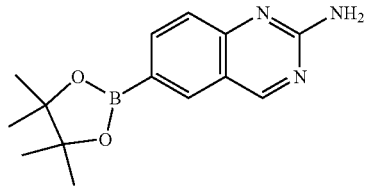 [SMILES: CC1(C)OB(c2ccc3nc(N)ncc3c2)OC1(C)C]

In a two neck RB to a solution of 6-bromoquinazolin-2-amine (1.5 g, 6.695 mmol) in 1,4-Dioxane (20 mL) was added potassium acetate (1.0 g, 10.042 mmol) and 4,4,5,5-tetramethyl-2-(4,4,5,5-tetramethyl-1,3,2-dioxaborolan-2-yl)-1,3,2-dioxaborolane (2.6 g, 10.042 mmol). The reaction mixture was degassed with nitrogen for 20 min followed by addition of Pd(PPh$_3$)$_2$Cl$_2$ (231 mg, 0.335 mmol). The reaction mixture was again degassed for 10 min and then refluxed at 100° C. for overnight. Reaction mass was diluted with water and extracted by DCM (3×50 mL). The combined organic layers were dried over anhydrous sodium sulphate and concentrated under reduced pressure and purified by column chromatography to obtain the title compound as solid (700 mg).

$^1$H NMR (400 MHz, (CD$_3$)$_3$SO: δ 9.20-9.14 (m, 1H), 8.17 (s, 1H), 7.86 (br d, 1H), 7.43-7.29 (m, 1H), 7.08-6.98 (m, 2H), 1.32 (s, 12H).

LC/MS (method F) m/z: 272 [M+H]$^+$, R$_t$=1.12 min.

Step B-3: Preparation of 6-[1-[4-(trifluoromethoxy)phenyl]-1,2,4-triazol-3-yl]quinazolin-2-amine

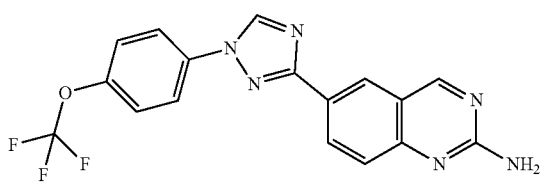 [SMILES: Nc1ncc2cc(-c3ncn(-c4ccc(OC(F)(F)F)cc4)n3)ccc2n1]

A mixture of 6-(4,4,5,5-tetramethyl-1,3,2-dioxaborolan-2-yl)quinazolin-2-amine (100 mg, 0.3689 mmol) and 3-bromo-1-[4-(trifluoromethoxy)phenyl]-1,2,4-triazole (110 mg, 0.3689 mmol)) in 1,4-Dioxane (2 mL) was added sodium bicarbonate (90 mg, 1.107 mmol) dissolved in water (1 mL) followed by addition of Pd(PPh$_3$)$_2$Cl$_2$ (25 mg, 0.0368 mmol;). Reaction mixture was then degassed for 10 min and cooked in microwave at 150° C. for 1 hour after which the reaction mixture was poured in water and and extracted with ethyl acetate (3×20 mL). The combined organic layer were dried over anhydrous sodium sulphate and concentrated under reduced pressure followed by column chromatography to obtain the title compound as solid (190 mg).

$^1$H NMR (400 MHz, (CD$_3$)$_3$SO: δ 9.48-9.39 (m, 1H), 9.28 (s, 1H), 8.54 (d, 1H), 8.43-8.34 (m, 1H), 8.14-8.04 (m, 2H), 7.71-7.60 (m, 2H), 7.54 (d, 1H), 7.11-6.96 (m, 2H)

LC/MS (method E) m/z: 373 [M+H]$^+$, R$_t$=0.75 min.

Step B-4: Preparation of 1-(2,6-dimethylphenyl)-3-[6-[1-[4-(trifluoromethoxy)phenyl]-1,2,4-triazol-3-yl]quinazolin-2-yl]thiourea (Component P2.5) and 1-(2,6-dimethylphenyl)-3-[6-[1-[4-(trifluoromethoxy)phenyl]-1,2,4-triazol-3-yl]quinazolin-2-yl]urea (Component P2.6)

To a stirring solution of 6-[1-[4-(trifluoromethoxy)phenyl]-1,2,4-triazol-3-yl]quinazolin-2-amine (300 mg, 0.8058 mmol) in tetrahydrofuran (6 mL) under nitrogen atmosphere was added sodium hydride (50 mg, 1.612 mmol) at 0° C. followed by 2-isothiocyanato-1,3-dimethyl-benzene (0.4 mL, 2.417 mmol) and reaction was refluxed at 60° C. for 3 hours. Reaction mass was then diluted with water and extracted with ethyl acetate (3×25 mL). Combined organic layers were then dried over anhydrous sodium sulphate and concentrated under reduced pressured followed by column chromatography of the crude compound to obtain the two title compounds as solids (150 mg and 70 mg respectively)

Compound P2.5

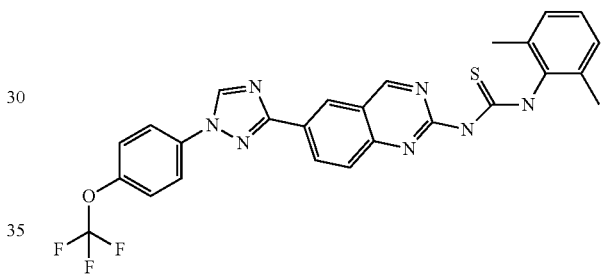

$^1$H NMR (400 MHz, (CD$_3$)$_3$SO: δ 2.26 (s, 6H), 7.17 (s, 3H), 7.66 (d, 2H), 8.08-8.19 (m, 3H), 8.62 (d, 1H), 8.84 (s, 1H), 9.51 (s, 1H), 9.73 (s, 1H), 11.34 (s, 1H), 12.85 (s, 1H)

LC/MS (method F) m/z: 536 [M+H]$^+$, R$_t$=1.72 min.

Compound P2.6

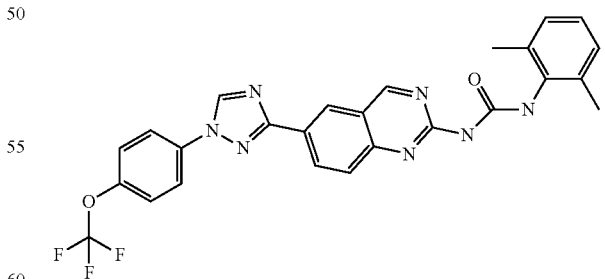

$^1$H NMR (400 MHz, (CD$_3$)$_3$SO: δ 2.30 (s, 6H), 7.15 (s, 3H), 7.66 (d, 2H), 8.07 (d1H), 8.13 (d, 2H), 8.60 (d, 1H), 8.81 (s, 1H), 9.51 (s, 1H), 9.68 (s, 1H), 10.44 (s, 1H), 11.12 (s, 1H)

LC/MS (method F) m/z: 520 [M+H]$^+$, R$_t$=1.68 min.

Example 7: Preparation of (2Z)-3-(2,6-dimethylphenyl)-4-methyl-2-[6-[1-[4-(trifluoromethoxy)phenyl]-1,2,4-triazol-3-yl]quinazolin-2-yl]imino-thiazolidin-4-ol (Compound P2.7)

(P2.7)

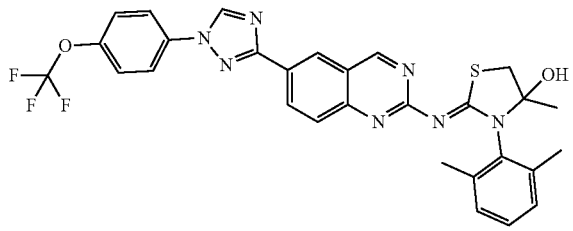

To the mixture of 1-(2,6-dimethylphenyl)-3-[6-[1-[4-(trifluoromethoxy)phenyl]-1,2,4-triazol-3-yl]quinazolin-2-yl]thiourea (60 mg, 0.112 mmol), methyl ethyl ketone (4 mL), triethylamine (0.05 mL, 0.3361 mmol) and tetrahydrofuran (1 mL) was added 1-chloropropan-2-one (0.03 mL, 0.2241 mmol). The reaction mass was then heated at 60° C. for overnight in a sealed tube. The reaction mass was then diluted with water and extracted with DCM (3×15 mL). The combined organic layers were then dried over sodium sulphate and concentrated under reduced pressure followed by column chromatography to obtain the title compound as solid (20 mg).
$^1$H NMR (400 MHz, (CD$_3$)$_3$SO: δ 1.45 (s, 3H), 2.21 (s, 3H), 2.40 (s, 3H), 3.40 (d, 1H), 3.62 (d, 1H), 7.24-7.33 (m, 3H), 7.67 (d, 2H), 7.94 (d, 1H), 8.13 (d, 2H), 8.62 (d, 1H), 8.74 (s, 1H), 9.41 (s, 1H), 9.52 (s, 1H)
LC/MS (method E) m/z: 592 [M+H]$^+$, R$_t$=1.12 min.

Example 8: Preparation of 3-(2,6-dimethylphenyl)-N-[6-[1-[4-(trifluoromethoxy)phenyl]-1,2,4-triazol-3-yl]quinazolin-2-yl]-1,3-thiazetidin-2-imine (Compound P2.8)

(P2.8)

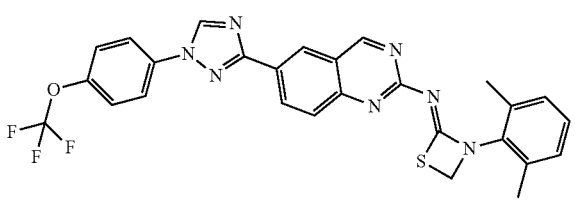

A suspension of 1-(2,6-dimethylphenyl)-3-[6-[1-[4-(trifluoromethoxy)phenyl]-1,2,4-triazol-3-yl]quinazolin-2-yl]thiourea (400 mg, 0.747 mmol), butan-2-one (15 mL), tetrahydrofuran (3 mL), potassium carbonate (600 mg, 3.735 mmol) and di-iodomethane (0.2 mL, 1.494 mmol) was heated at 60° C. for overnight. The reaction mass was then diluted with water and extracted with DCM (3×25 mL). The combined organic layers were then dried over sodium sulphate and concentrated under reduced pressure followed by column chromatography to obtain the title compound as solid (120 mg).
$^1$H NMR (400 MHz, CDCl$_3$: δ 2.40 (s, 6H), 4.92 (s, 2H), 7.03-7.13 (m, 2H), 7.17 (d, 1H), 7.42 (d, 2H), 7.79-7.98 (m, 3H), 8.56-8.67 (m, 3H), 9.32 (s, 1H)
LC/MS (method F) m/z: 548 [M+H]$^+$, R$_t$=1.70 min.

Example 9: Preparation of (2Z)-3-(2,6-dimethylphenyl)-2-[6-[1-[4-(trifluoromethoxy)phenyl]-1,2,4-triazol-3-yl]quinazolin-2-yl]imino-thiazolidin-4-one (Compound P2.9) and (2Z)-2-(2,6-dimethyl-phenyl)imino-3-[7-[1-[4-(trifluoromethoxy)phenyl]-1,2,4-triazol-3-yl]quinazolin-2-yl]thiazolidin-4-one (Compound P2.10)

(P2.9)

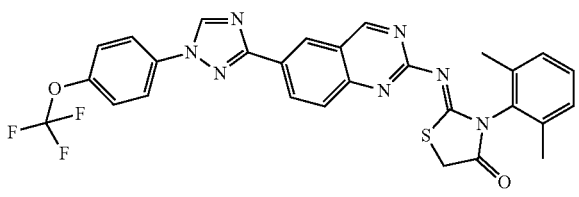 [SMILES: Cc1cccc(C)c1N1C(=O)CS/C1=N\c1ncc2cc(-c3ncn(-c4ccc(OC(F)(F)F)cc4)n3)ccc2n1]

(P2.10)

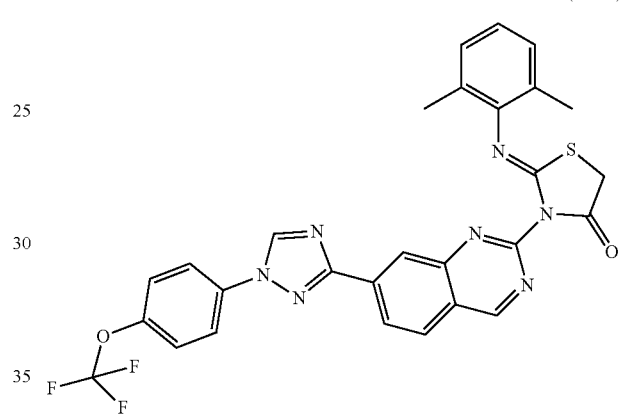

In a 2 neck round bottom flask equipped with a two way stopcock and a condenser was added 1-(2,6-dimethylphenyl)-3-[6-[1-[4-(trifluoromethoxy)phenyl]-1,2,4-triazol-3-yl]quinazolin-2-yl]thiourea (200 mg, 0.3735 mmol) methyl ethyl ketone (4 mL), THF (5 ml), triethylamine (0.2 mL, 1.120 mmol) and 2-chloroacetyl chloride (0.44 ml, 0.4482 mmol) one after the other. Reaction was allowed to stir for 30 min at room temperature and then heated at 70° C. for overnight. The reaction mass was then diluted with water and extracted with DCM (3×25 mL). The combined organic layers were then dried over sodium sulphate and concentrated under reduced pressure followed by column chromatography to obtain the two title compounds both as solids (46 mg and 27 mg respectively)

Compound P2.9

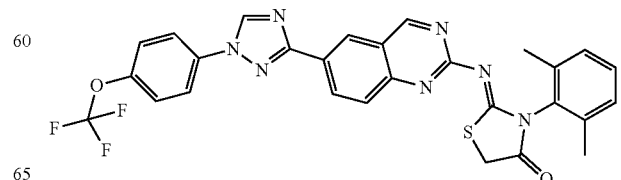

¹H NMR (400 MHz, CDCl₃: δ 2.18 (s, 6H), 4.09 (s, 2H), 6.90-6.95 (m, 1H), 6.98-7.03 (m, 2H), 7.43 (d, 2H), 7.85 (d, 2H), 8.25 (d, 1H), 8.66 (s, 1H), 8.82-8.92 (m, 2H), 9.67 (s, 1H)

LC/MS (method F) m/z: 576 [M+H]⁺, $R_t$=1.67 min.

Compound P2.10

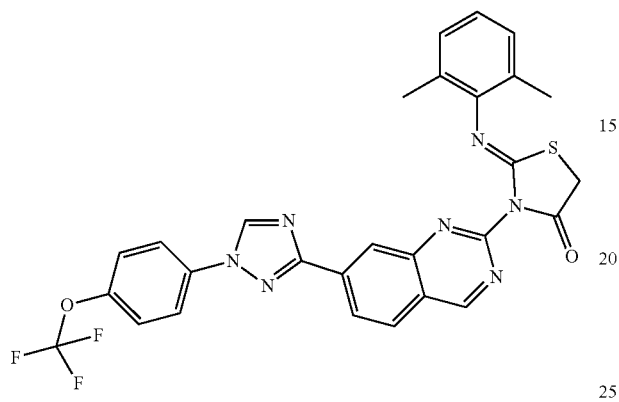

¹H NMR (400 MHz, CDCl₃: δ 2.23 (s, 6H,) 4.05 (s, 2H), 7.16-7.22 (m, 2H), 7.27-7.30 (m, 1H), 7.38-7.46 (m, 2H), 7.80-7.88 (m, 2H), 8.02-8.09 (m, 1H), 8.61-8.76 (m, 3H), 9.39-9.47 (m, 1H)

LC/MS (method F) m/z: 576 [M+H]⁺, $R_t$=1.67 min.

Example 10: Preparation of 1-(2,6-dimethylphenyl)-3-[6-[1-[4-(trifluoromethoxy)phenyl]-1,2,4-triazol-3-yl]quinoxalin-2-yl]thiourea (Compound P2.11)

(P2.11)

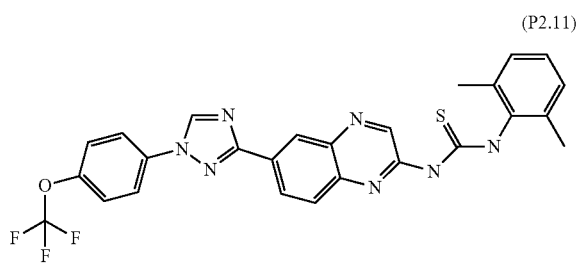 [SMILES: Cc1cccc(C)c1NC(=S)Nc1cnc2cc(-c3ncn(-c4ccc(OC(F)(F)F)cc4)n3)ccc2n1]

Step C-1: Preparation of 6-(4,4,5,5-tetramethyl-1,3,2-dioxaborolan-2-yl)quinoxalin-2-amine

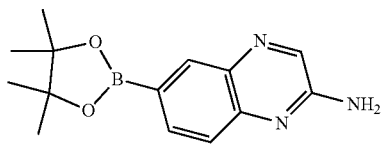 [SMILES: CC1(C)OB(c2ccc3nc(N)cnc3c2)OC1(C)C]

To the solution of tert-butyl N-(6-bromoquinoxalin-2-yl)carbamate (400 mg, 1.234 mmol) in 1,4-Dioxane (10 mL) was added potassium acetate (180 mg, 2.008 mmol) and 4,4,5,5-tetramethyl-2-(4,4,5,5-tetramethyl-1,3,2-dioxaborolan-2-yl)-1,3,2-dioxaborolane (442 mg, 1.851 mmol). To the reaction mixture was then added Pd(PPh₃)₂Cl₂ (110 mg, 0.0617 mmol) and it was refluxed at 100° C. for overnight. The reaction mass was then diluted with water and extracted with dichloromethane (3×25 mL). The combined organic layers were then dried over sodium sulphate and concentrated under reduced pressure followed by column chromatography to obtain the title compound as solid (125 mg).

¹H NMR (400 MHz, CDCl₃: δ 1.39 (s, 12H), 5.19 (br. s, 2H), 7.63 (d, 1H), 7.92-8.03 (m, 1H), 8.35 (s, 1H), 8.41 (s, 1H)

LC/MS (method E) m/z: 272 [M+H]⁺, $R_t$=0.77 min.

Step C-2: Preparation of 6-[1-[4-(trifluoromethoxy)phenyl]-1,2,4-triazol-3-yl]quinoxalin-2-amine

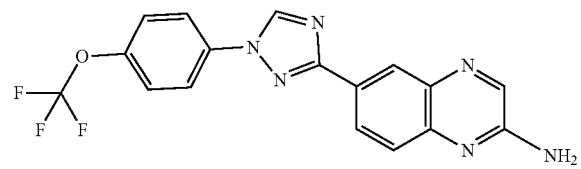

A mixture of 4,4,5,5-tetramethyl-1,3,2-dioxaborolan-2-yl)quinoxalin-2-amine (250 mg, 0.9222 mmol), 1,4-Dioxane (4 mL), 3-bromo-1-[4-(trifluoromethoxy)phenyl]-1,2,4-triazole (283 mg, 0.922 mmol), sodium bicarbonate solution (230 mg, 2.767 mmol in 1 mL water) was degassed with nitrogen for 20 min and then was added Pd(PPh₃)₂Cl₂ (64 mg, 0.0922 mmol). Reaction was again degassed for 10 min and then was cooked in microwave at 140° C. for 1 hour. The reaction mass was then diluted with water and extracted with ethylacetate (3×25 mL). The combined organic layers were then dried over sodium sulphate and concentrated under reduced pressure followed by column chromatography to obtain the title compound as solid (80 mg).

¹H NMR (400 MHz, (CD₃)₃SO: δ 9.48-9.38 (m, 1H), 8.50-8.43 (m, 1H), 8.36 (s, 1H), 8.26 (dd, 1H), 8.15-8.05 (m, 2H), 7.69-7.60 (m, 3H), 7.23-7.13 (m, 2H)

LC/MS (method E) m/z: 373 [M+H]⁺, $R_t$=0.82 min.

Step C-3: Preparation of 1-(2,6-dimethylphenyl)-3-[6-[1-[4-(trifluoromethoxy)phenyl]-1,2,4-triazol-3-yl]quinoxalin-2-yl]thiourea (Compound P2.11)

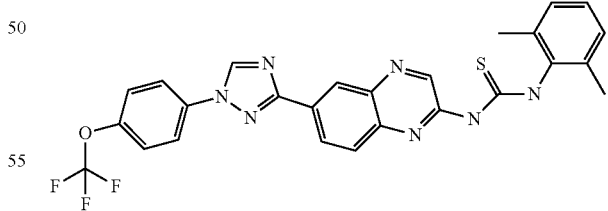

To a stirring solution of 6-[1-[4-(trifluoromethoxy)phenyl]-1,2,4-triazol-3-yl]quinoxalin-2-amine (350 mg, 0.9401 mmol) in tetrahydrofuran (16 mL) under nitrogen atmosphere was added sodium hydride (150 mg, 3.760 mmol) at 0° C. followed by 2-isothiocyanato-1,3-dimethyl-benzene (0.6 mL, 3.760 mmol). The reaction mixture was then heated at 60° C. for 3 hours. The reaction mass was then diluted with water and extracted with ethylacetate (3×25 mL). The combined organic layers were then dried over sodium sulphate and concentrated under reduced pressure followed by column chromatography to obtain the title compound as solid (325 mg).

¹H NMR (400 MHz, (CD₃)₃SO: δ 2.27 (s, 6H), 7.10-7.33 (m, 3H), 7.64 (d, 2H), 8.04-8.16 (m, 2H), 8.16-8.30 (m, 1H), 8.44 (dd, 1H), 8.63 (d, 1H), 8.96 (s, 1H), 9.49 (s, 1H), 11.65 (s, 1H), 12.56-12.83 (m, 1H)

LC/MS (method E) m/z: 534 [M+H]⁺, $R_t$=1.14 min.

Example 11: Preparation of 3-(2,6-dimethylphenyl)-N-[6-[1-[4-(trifluoromethoxy)phenyl]-1,2,4-triazol-3-yl]quinoxalin-2-yl]-1,3-thiazetidin-2-imine (Compound P2.12)

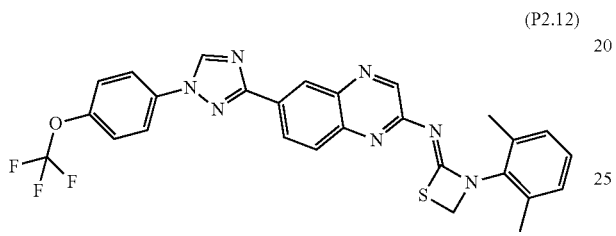
(P2.12)

To a mixture of 1-(2,6-dimethylphenyl)-3-[6-[1-[4-(trifluoromethoxy)phenyl]-1,2,4-triazol-3-yl]quinoxalin-2-yl] thiourea (250 mg, 0.4669 mmol), butan-2-one (15 mL) and potassium carbonate (380 mg, 2.334 mmol) was added di-iodomethane (0.12 mL, 0.9337 mmol). The reaction mixture was then heated at 60° C. for overnight. The reaction mass was then diluted with water and extracted with ethylacetate (3×20 mL). The combined organic layers were then dried over sodium sulphate and concentrated under reduced pressure followed by column chromatography to obtain the title compound as solid (130 mg).

¹H NMR (400 MHz, CDCl₃: δ 2.43 (s, 6H), 5.01 (s, 2H), 7.17 (m, 2H), 7.27 (m, 1H), 7.43 (d, 2H), 7.86 (d, 2H), 7.97 (d, 1H), 8.50 (dd, 1H), 8.59 (s, 1H), 8.64 (s, 1H), 8.82 (d, 1H)

LC/MS (method E) m/z: 548 [M+H]⁺, $R_t$=1.18 min.

Example 12: Preparation of 1-(2,6-dimethylphenyl)-3-[6-[1-[4-(trifluoromethoxy)phenyl]-1,2,4-triazol-3-yl]-1,3-benzothiazol-2-yl]urea (Compound P2.16) and 1-(2,6-dimethylphenyl)-3-[6-[1-[4-(trifluoromethoxy)phenyl]-1,2,4-triazol-3-yl]-1,3-benzothiazol-2-yl]thiourea (Compound P2.17)

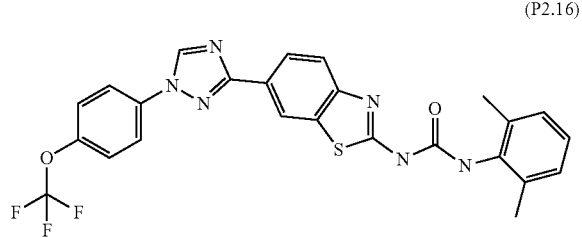
(P2.16)

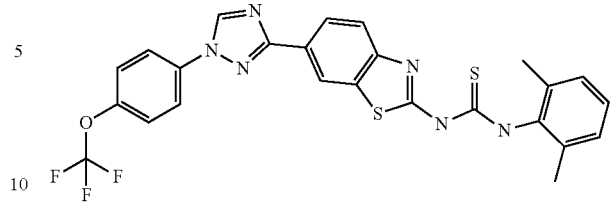
(P17)

Step D-1: Preparation of 6-(4,4,5,5-tetramethyl-1,3,2-dioxaborolan-2-yl)-1,3-benzothiazol-2-amine

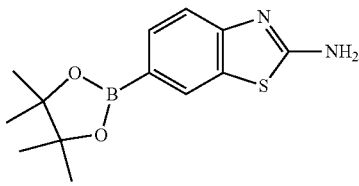 [SMILES: CC1(C)OB(c2ccc3nc(N)sc3c2)OC1(C)C]

To the stirring solution of 6-bromo-1,3-benzothiazol-2-amine (5 g, 21.825 mmol) in 1,4-Dioxane (80 mL) was added potassium acetate (3 g, 32.737 mmol) and 4,4,5,5-tetramethyl-2-(4,4,5,5-tetramethyl-1,3,2-dioxaborolan-2-yl)-1,3,2-dioxaborolane (8.3 g, 32.737 mmol). The reaction mixture was degassed with nitrogen for 20 min followed by addition of Pd(PPh₃)₂Cl₂ (850 mg, 1.0912 mmol). The reaction mixture was again degassed for 10 min and then refluxed at 100° C. for overnight. The reaction mass was then diluted with water and extracted with dichloromethane (3×100 mL). The combined organic layers were then dried over sodium sulphate and concentrated under reduced pressure followed by column chromatography to obtain the title compound as solid (5 g).

¹H NMR (400 MHz, CDCl₃: δ 1.35 (s, 12H), 5.45 (br. s, 2H), 7.53 (d, 1H), 7.75 (d, 1H), 8.06 (s, 1H)

LC/MS (method E) m/z: 277 [M+H]⁺, $R_t$=0.96 min.

Step D-2: Synthesis of 6-[1-[4-(trifluoromethoxy)phenyl]-1,2,4-triazol-3-yl]-1,3-benzothiazol-2-amine

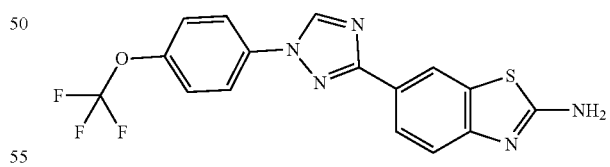

To a solution of 6-(4,4,5,5-tetramethyl-1,3,2-dioxaborolan-2-yl)-1,3-benzothiazol-2-amine (1 g, 3.621 mmol) in 1,4-Dioxane (12 mL) was added 3-bromo-1-[4-(trifluoromethoxy)phenyl]-1,2,4-triazole (1.11 g, 3.621 mmol) and sodium bicarbonate solution (900 mg, 10.86 mmol in 3 mL water). Then reaction mixture was degassed with nitrogen, followed by addition of Pd(PPh₃)₂Cl₂ (250 mg, 0.3621 mmol) and was degassed again for 10 min. The reaction mass was then diluted with water and extracted with ethylacetate (3×50 mL). The combined organic layers were then dried over sodium sulphate and concentrated under reduced pressure followed by column chromatography to obtain the title compound as solid (350 mg).

LC/MS (method E) m/z: 378 [M+H]$^+$, R$_t$=1.05 min.

Step D-3: Preparation of 1-(2,6-dimethylphenyl)-3-[6-[1-[4-(trifluoromethoxy)phenyl]-1,2,4-triazol-3-yl]-1,3-benzothiazol-2-yl]urea (Compound P2.16) and 1-(2,6-dimethylphenyl)-3-[6-[1-[4-(trifluoromethoxy)phenyl]-1,2,4-triazol-3-yl]-1,3-benzothiazol-2-yl]thiourea (Compound P2.17)

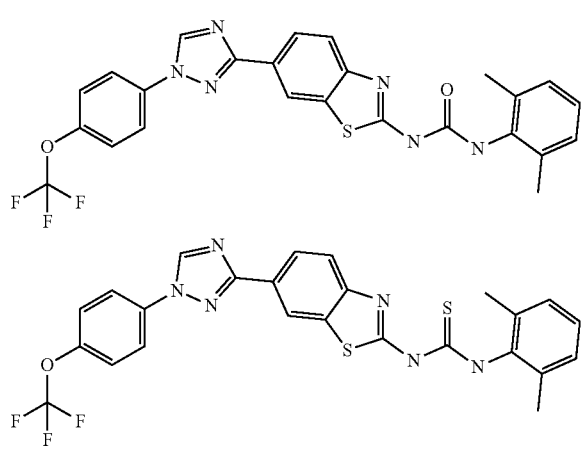

To a stirring solution of 6-[1-[4-(trifluoromethoxy)phenyl]-1,2,4-triazol-3-yl]-1,3-benzothiazol-2-amine (350 mg, 0.9276 mmol) in tetrahydrofuran (6 mL) under nitrogen atmosphere was added sodium hydride (180 mg, 3.711 mmol) at 0° C. followed by addition of 2-isothiocyanato-1,3-dimethyl-benzene (0.8 mL, 4.638 mmol). The reaction mixture was then heated at 60° C. for overnight. The reaction mass was then diluted with water and extracted with ethylacetate (3×30 mL). The combined organic layers were then dried over sodium sulphate and concentrated under reduced pressure followed by column chromatography to obtain the two title compounds both as solids (115 mg and 145 mg respectively).

Compound P2.16

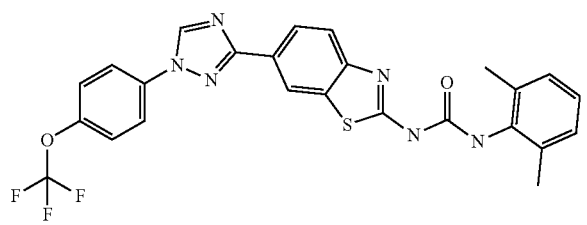 [SMILES: Cc1cccc(C)c1NC(=O)Nc1nc2ccc(-c3ncn(-c4ccc(OC(F)(F)F)cc4)n3)cc2s1]

$^1$H NMR (400 MHz, (CD$_3$)$_3$SO): δ 2.24 (s, 6H), 7.13 (s, 3H), 7.64 (d, 2H), 7.79 (d, 1H), 8.06-8.18 (m, 3H), 8.37 (br. s., 1H), 8.63 (s, 1H), 9.42 (s, 1H), 11.02 (s, 1H)

LC/MS (method E) m/z: 525 [M+H]$^+$, R$_t$=1.21 min.

Compound P2.17

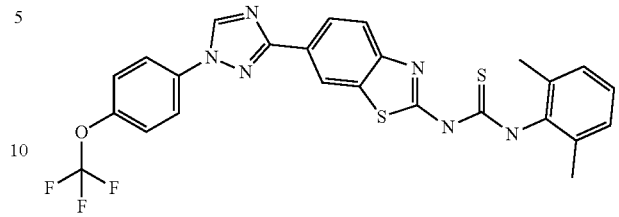

$^1$H NMR (400 MHz, CDCl$_3$): δ 2.40 (s, 6H), 7.20-7.27 (m, 3H), 7.43 (d, 2H), 7.80-7.86 (m, 3H), 8.32 (d, 1H), 8.62 (s, 2H)

LC/MS (method E) m/z: 541 [M+H]$^+$, R$_t$=1.25 min.

Example 13: Preparation of 3-(2,6-dimethylphenyl)-N-[6-[1-[4-(trifluoromethoxy)phenyl]-1,2,4-triazol-3-yl]-1,3-benzothiazol-2-yl]-1,3-thiazetidin-2-imine (Compound P2.14) and N-(2,6-dimethylphenyl)-3-[6-[1-[4-(trifluoromethoxy)phenyl]-1,2,4-triazol-3-yl]-1,3-benzothiazol-2-yl]-1,3-thiazetidin-2-imine (Compound P2.15)

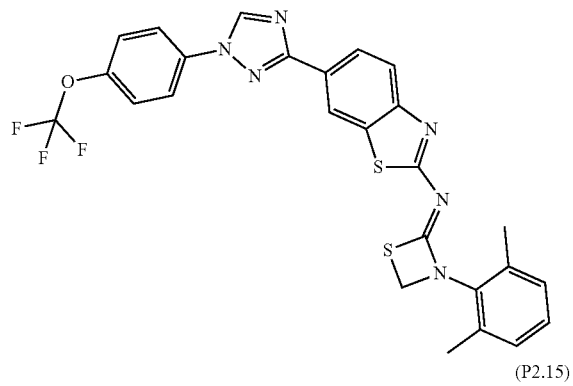

(P2.14)

(P2.15)

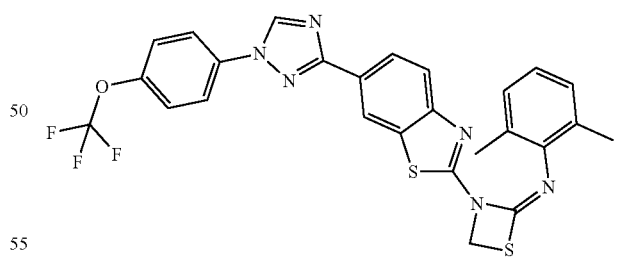

To a mixture of 1-(2,6-dimethylphenyl)-3-[6-[1-[4-(trifluoromethoxy)phenyl]-1,2,4-triazol-3-yl]-1,3-benzothiazol-2-yl]thiourea (300 mg, 0.5549 mmol), butan-2-one (15 mL) and tetrahydrofuran (3 mL) was added potassium carbonate (450 mg, 2.775 mmol) and di-iodomethane (0.13 mL, 1.110 mmol). The reaction mixture was the heated at 60° C. for overnight. The reaction mass was then diluted with water and extracted with ethylacetate (3×30 mL). The combined organic layers were then dried over sodium sulphate and concentrated under reduced pressure followed by column chromatography to obtain the two title compounds both as solids (15 mg and 20 mg respectively).

Compound P2.14

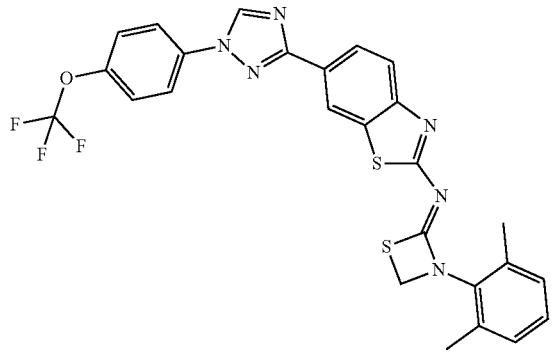 [SMILES: Cc1cccc(C)c1N1CS/C1=N\c1nc2ccc(-c3ncn(-c4ccc(OC(F)(F)F)cc4)n3)cc2s1]

$^1$H NMR (400 MHz, CDCl$_3$: δ 2.40 (s, 6H), 4.92 (s, 2H), 7.10-7.17 (m, 2H), 7.19-7.26 (m, 1H), 7.40 (d, 2H), 7.83 (dd, 3H), 8.15-8.25 (m, 1H), 8.51-8.60 (m, 2H)

LC/MS (method F) m/z: 553 [M+H]$^+$, R$_t$=1.79 min.

Compound P2.15

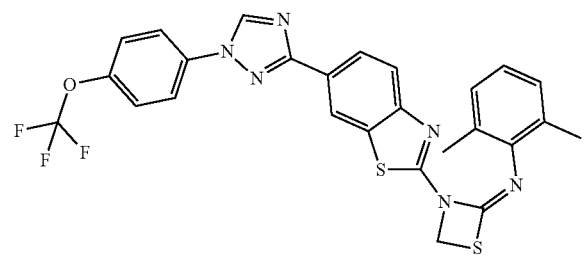 [SMILES: Cc1cccc(C)c1/N=C1/SCN1c1nc2ccc(-c3ncn(-c4ccc(OC(F)(F)F)cc4)n3)cc2s1]

$^1$H NMR (400 MHz, CDCl$_3$: δ 2.27 (s, 6H), 5.21 (s, 2H), 6.94-7.02 (m, 1H), 7.08 (d, 2H), 7.41 (d, 2H), 7.82 (d, 2H), 7.87 (d, 1H), 8.30 (d, 1H), 8.60 (d, 2H)

LC/MS (method F) m/z: 553 [M+H]$^+$, R$_t$=1.87 min.

Example 14: Preparation of 1-(2,6-dimethylphenyl)-3-[6-[1-[4-(trifluoromethoxy)phenyl]-1,2,4-triazol-3-yl]-2-naphthyl]thiourea (Compound P2.13)

(P2.13)

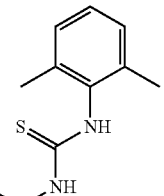

This compound was prepared in a similar way as compound P2.11 (Example 10)

$^1$H NMR (400 MHz, (CD$_3$)$_3$SO: δ 2.17-2.33 (m, 6H), 6.98-7.21 (m, 3H), 7.56-7.78 (m, 3H), 7.89-8.32 (m, 6H), 8.58-8.76 (m, 1H), 9.46 (s, 1H)

LC/MS (method E) m/z: 534 [M+H]$^+$, R$_t$=1.62 min.

TABLE P1

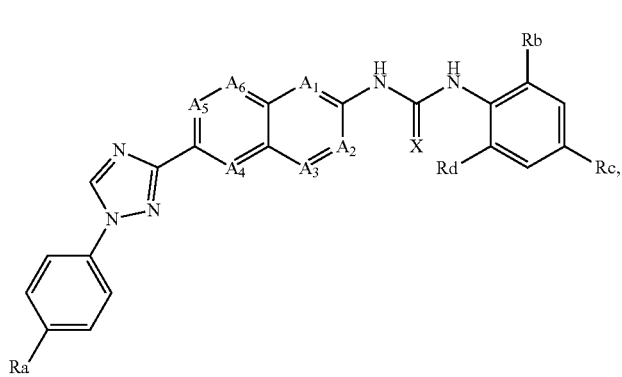

(I-1a)

wherein R$^a$, A$^1$, A$^2$, A$^3$, A$^4$, A$^5$ A$^6$, R$^b$, R$^c$, R$^d$ and X are as defined below:

| | R$^a$ | A$^1$ | A$^2$ | A$^3$ | A$^4$ | A$^5$ | A$^6$ | R$^b$ | R$^c$ | R$^d$ | X | LC MS/NMR | Mp/° C. |
|---|---|---|---|---|---|---|---|---|---|---|---|---|---|
| P1.1 | OCF$_3$ | N | CH | CH | CH | CH | CH | CH$_3$ | H | CH$_3$ | O | | |
| P1.2 | OCF$_3$ | N | CH | CH | CH | CH | CH | CH$_3$ | H | CH$_3$ | S | 535 [M + H]$^+$ R$_t$ = 2.25 min Method B | 202-3 |
| P1.3 | OCF$_3$ | N | CH | CH | CH | CH | CH | iPr | H | H | O | 532.8 [M + H]$^+$ Method D | 230-5 |

TABLE P1-continued

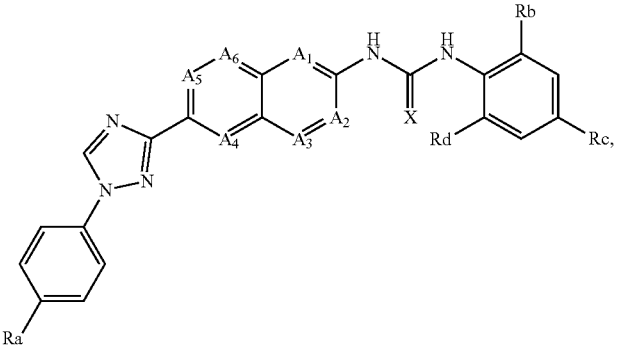

(I-1a)

wherein $R^a$, $A^1$, $A^2$, $A^3$, $A^4$, $A^5$ $A^6$, $R^b$, $R^c$, $R^d$ and X are as defined below:

| | $R^a$ | $A^1$ | $A^2$ | $A^3$ | $A^4$ | $A^5$ | $A^6$ | $R^b$ | $R^c$ | $R^d$ | X | LC MS/NMR | Mp/° C. |
|---|---|---|---|---|---|---|---|---|---|---|---|---|---|
| P1.4 | OCF$_3$ | N | CH | CH | CH | CH | CH | iPr | H | H | S | 548.9 [M + H]$^{+\cdot}$ Method D | 215-20 |
| P1.5 | OCF$_3$ | N | CH | CH | CH | CH | CH | CH$_3$ | H | Cl | S | | |
| P1.6 | OCF$_3$ | CH | CH | CH | CH | CH | CH | CH$_3$ | H | CH$_3$ | S | | |
| P1.7 | OCF$_3$ | CH | CH | CH | CH | CH | CH | iPr | H | H | S | | |
| P1.8 | OCF$_3$ | CH | CH | CH | CH | CH | CH | iPr | H | H | O | | |
| P1.9 | OCF$_3$ | CH | CH | CH | CH | CH | CH | CH$_3$ | H | Cl | S | | |
| P1.10 | OCF$_3$ | N | N | CH | CH | CH | CH | CH$_3$ | H | CH$_3$ | S | | |
| P1.11 | OCF$_3$ | N | N | CH | CH | CH | CH | iPr | H | H | S | | |
| P1.12 | OCF$_3$ | N | N | CH | CH | CH | CH | iPr | H | H | O | | |
| P1.13 | OCF$_3$ | N | N | CH | CH | CH | CH | CH$_3$ | H | Cl | S | | |
| P1.14 | OCF$_3$ | N | CH | N | CH | CH | CH | CH$_3$ | H | CH$_3$ | S | | |
| P1.15 | OCF$_3$ | N | CH | N | CH | CH | CH | iPr | H | H | S | | |
| P1.16 | OCF$_3$ | N | CH | N | CH | CH | CH | iPr | H | H | O | | |
| P1.17 | OCF$_3$ | N | CH | N | CH | CH | CH | CH$_3$ | H | Cl | S | | |
| P1.18 | OCF$_3$ | N | CH | CH | CH | CH | N | CH$_3$ | H | CH$_3$ | S | | |
| P1.19 | OCF$_3$ | N | CH | CH | CH | CH | N | iPr | H | H | S | | |
| P1.20 | OCF$_3$ | N | CH | CH | CH | CH | N | CH$_3$ | H | Cl | S | | |
| P1.21 | OCF$_3$ | N | CH | CH | CH | CH | N | CH$_3$ | H | Cl | O | | |
| P1.22 | OCF$_3$ | CH | CH | CH | CH | CH | N | iPr | H | H | S | | |
| P1.23 | OCF$_3$ | CH | CH | CH | N | CH | CH | iPr | H | H | S | | |
| P1.24 | OCF$_3$ | CH | CH | N | N | CH | CH | iPr | H | H | S | | |

TABLE P2

| | Structure | LS MS/NMR | Mp/° C. |
|---|---|---|---|
| P2.1 | 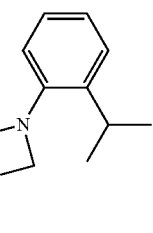 | 561 (M + H)$^+$ R$_t$ = 2.47 min Method B | 102-3 |
| P2.2 | 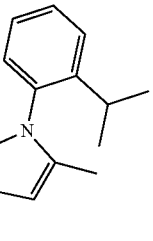 | 587 (M + H)$^+$ R$_t$ = 2.26 min Method B | |

TABLE P2-continued

| | Structure | LS MS/NMR | Mp/° C. |
|---|---|---|---|
| P2.3 | 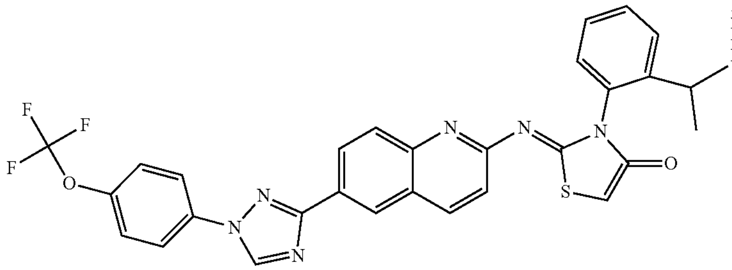 | 589 (M + H)+ Rt = 2.30 min Method B | |
| P2.4 | 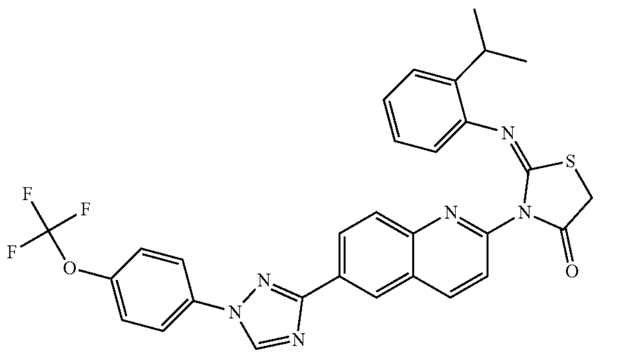 [SMILES: CC(C)c1ccccc1/N=C1/SCC(=O)N1c1ccc2cc(-c3ncn(-c4ccc(OC(F)(F)F)cc4)n3)ccc2n1] | 589 (M + H)+ Rt = 2.24 min Method B | |
| P2.5 | 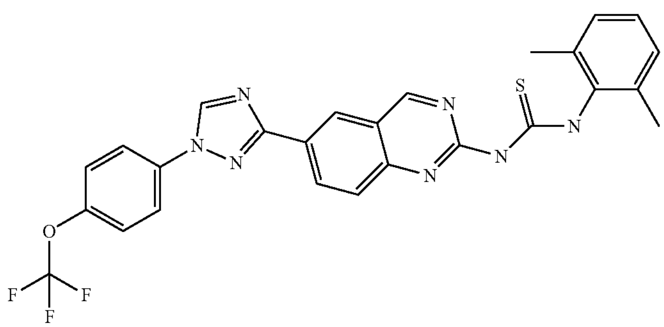 [SMILES: Cc1cccc(C)c1NC(=S)Nc1ncc2cc(-c3ncn(-c4ccc(OC(F)(F)F)cc4)n3)ccc2n1] | 536 (M + H)+ Rt = 1.72 min Method F | |
| P2.6 | 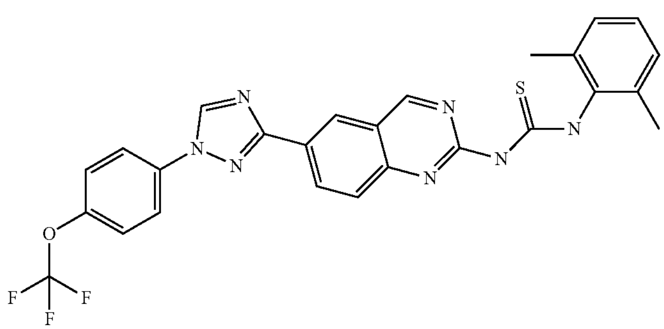 | 520 (M + H)+ Rt = 1.68 min Method F | 247-9 |
| P2.7 | 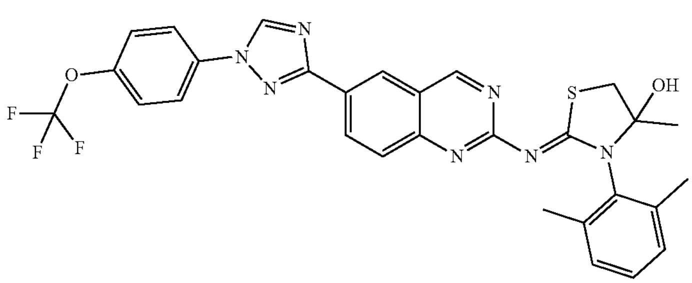 [SMILES: Cc1cccc(C)c1N1/C(=N/c2ncc3cc(-c4ncn(-c5ccc(OC(F)(F)F)cc5)n4)ccc3n2)SCC1(C)O] | 592 (M + H)+ Rt = 1.12 min Method E | 196-8 |

TABLE P2-continued
| | Structure | LS MS/NMR | Mp/° C. |
|---|---|---|---|
| P2.8 | 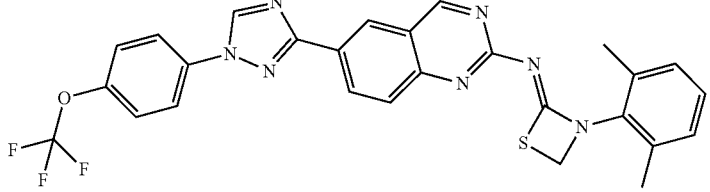 | 548 (M + H)+<br>Rt = 1.70 min<br>Method F | 227-9 |
| P2.9 | 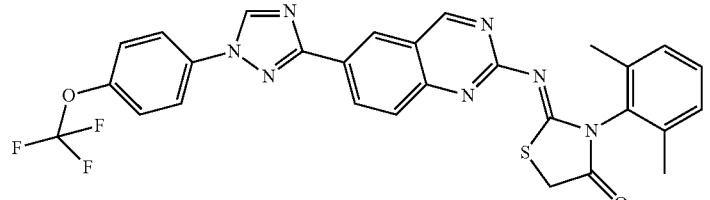 | 576 (M + H)+<br>Rt = 1.67 min<br>Method F | |
| P2.10 | 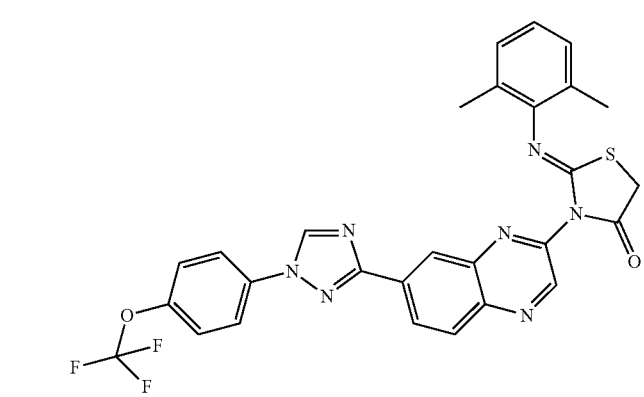 [SMILES: Cc1cccc(C)c1/N=C1\SCC(=O)N1c1cnc2ccc(-c3ncn(-c4ccc(OC(F)(F)F)cc4)n3)cc2n1] | 576 (M + H)+<br>Rt = 1.67 min<br>Method F | |
| P2.11 | 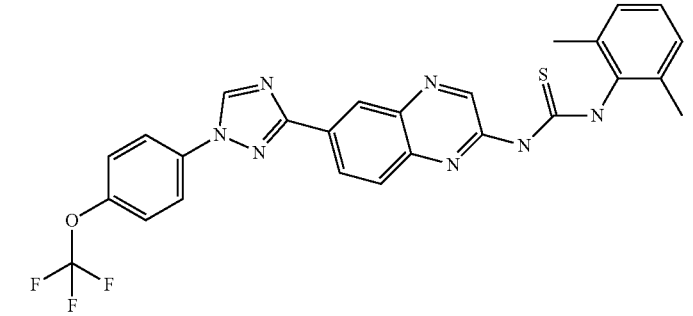 [SMILES: Cc1cccc(C)c1NC(=S)Nc1cnc2cc(-c3ncn(-c4ccc(OC(F)(F)F)cc4)n3)ccc2n1] | 534 (M − H)+<br>Rt = 1.14 min<br>Method E | 217-9 |
| P2.12 | 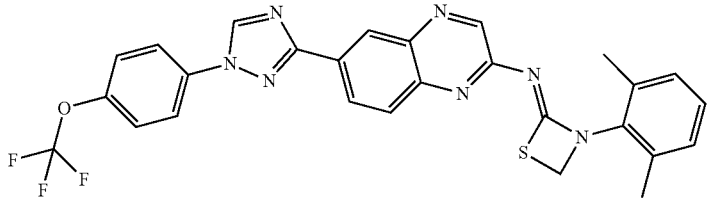 [SMILES: Cc1cccc(C)c1N1CS/C1=N\c1cnc2cc(-c3ncn(-c4ccc(OC(F)(F)F)cc4)n3)ccc2n1] | 548 (M + H)+<br>Rt = 1.18 min<br>Method E | 197-9 |
| P2.13 | 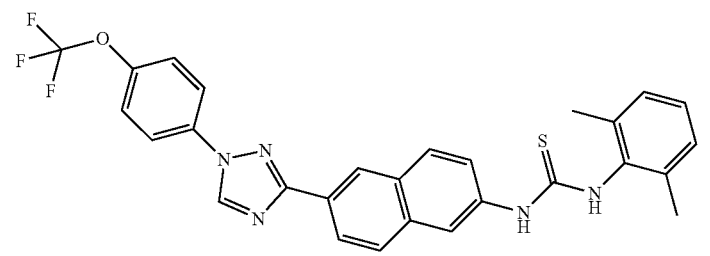 [SMILES: Cc1cccc(C)c1NC(=S)Nc1ccc2cc(-c3ncn(-c4ccc(OC(F)(F)F)cc4)n3)ccc2c1] | 534 (M + H)+<br>Rt = 1.62 min<br>Method F | |

TABLE P2-continued

| | Structure | LS MS/NMR | Mp/° C. |
|---|---|---|---|
| P2.14 | 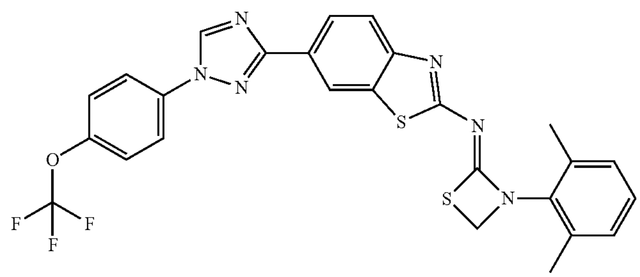 [SMILES: Cc1cccc(C)c1N1CS/C1=N\c1nc2ccc(-c3ncn(-c4ccc(OC(F)(F)F)cc4)n3)cc2s1] | 553 (M + H)+<br>Rt = 1.79 min<br>Method F | >250 |
| P2.15 | 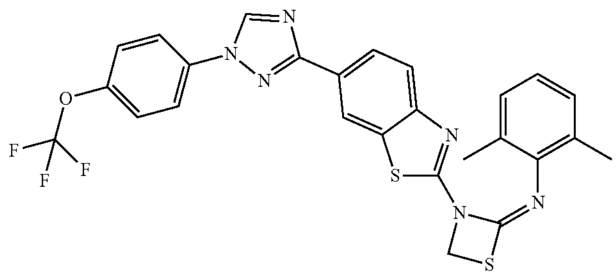 [SMILES: Cc1cccc(C)c1/N=C1/SCN1c1nc2ccc(-c3ncn(-c4ccc(OC(F)(F)F)cc4)n3)cc2s1] | 553 (M + H)+<br>Rt = 1.87 min<br>Method F | >250 |
| P2.16 | 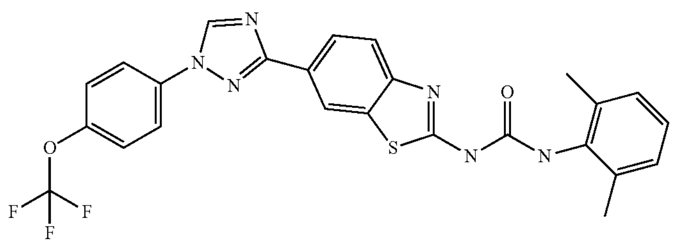 [SMILES: Cc1cccc(C)c1NC(=O)Nc1nc2ccc(-c3ncn(-c4ccc(OC(F)(F)F)cc4)n3)cc2s1] | 525 (M + H)+<br>Rt = 1.21 min<br>Method E | |
| P2.17 | 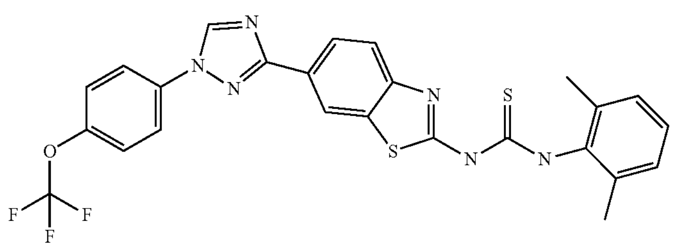 | 541 (M + H)+<br>Rt = 1.25 min<br>Method E | >250 |

Biological Examples (%=Percent by Weight, Unless Otherwise Specified)

Example B1: *Spodoptera littoralis* (Egyptian Cotton Leaf Worm)

Cotton leaf discs were placed on agar in 24-well microtiter plates and sprayed with aqueous test solutions prepared from 10,000 ppm DMSO stock solutions. After drying, the leaf discs were infested with five L1 larvae. The samples were assessed for mortality, anti-feedant effect, and growth inhibition in comparison to untreated samples 3 days after infestation. Control of Spodoptera littoralis by a test sample is when at least one of mortality, anti-feedant effect, and growth inhibition is higher than the untreated sample.

The following compounds resulted in at least 80% control at an application rate of 200 ppm: P1.2, P1.4, P2.1, P2.2, P2.3, P2.4, P2.9, P2.10, P2.11, P2.12, P2.13, P2.14 and P2.17.

Example B2: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1.2, P1.3, P1.4, P2.1, P2.2, P2.3. P2.4, P2.9, P2.10, P2.11, P2.13, P2.14 and P2.17.

Example B3: *Diabrotica balteata* (Corn Root Worm)

Maize sprouts, placed on an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1.2, P1.3, P1.4, P2.1, P2.2, P2.3. P2.4, P2.7, P2.9, P2.10, P2.11, P2.13 and P2.17.

Example B4: *Euschistus heros*

Soybean leaf on agar in 24-well microtiter plates were sprayed with aqueous test solutions prepared from 10,000 ppm DMSO stock solutions. After drying the leaf were infested with N-2 nymphs. The samples were assessed for growth inhibition in comparison to untreated samples 5 days after infestation.

The following compounds gave an effect of at least 80% in at least one of the two categories (mortality or growth inhibition) at an application rate of 200 ppm: P2.4, P2.7 and P2.17.

Example B5: *Thrips tabaci* (Onion Thrips)

Sunflower leaf discs were placed on agar in 24-well microtiter plates and sprayed with aqueous test solutions prepared from 10,000 ppm DMSO stock solutions. After drying the leaf discs were infested with a thrips population of mixed ages. The samples were assessed for mortality 6 days after infestation.

The following compounds resulted in at least 80% mortality at an application rate of 200 ppm: P2.4 and P2.14.

Example B6: *Frankliniella occidentalis* (Western Flower Thrips)

Sunflower leaf discs were placed on agar in 24-well microtiter plates and sprayed with aqueous test solutions prepared from 10,000 DMSO stock solutions. After drying the leaf discs were infested with a Frankliniella population of mixed ages. The samples were assessed for mortality 7 days after infestation.

The following compounds resulted in at least 80% mortality at an application rate of 200 ppm: P2.1, P2.2, P2.3, P2.4 and P2.12.

The invention claimed is:

1. A compound of formula (I)

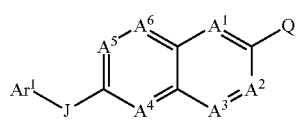
(I)

or wherein Q is selected from

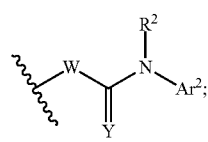
(i)

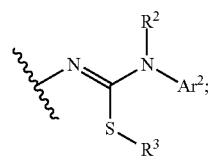
(ii)

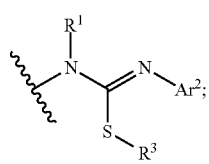
(iii)

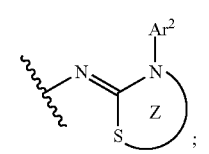
(iv)

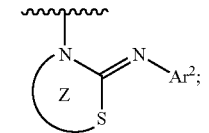
(v)

$A^1$ is N or $CR^{A1}$;
$A^2$ is N or $CR^{A2}$;
$A^3$ is N or $CR^{A3}$;
$A^4$ is N or $CR^{A4}$;
$A^5$ is N or $CR^{A5}$;
$A^6$ is N or $CR^{A6}$;
with the proviso that not more than four of $A^1, A^2, A^3, A^4, A^5$ and $A^6$ are N;
$R^{A1}, R^{A2}, R^{A3}, R^{A4}, R^{A5}$ and $R^{A6}$ are independently selected from H, $C_1$-$C_6$alkyl, $C_2$-$C_6$alkenyl, $C_2$-$C_6$alkynyl, —($C_0$-$C_6$alkyl)($C_{3-6}$ cycloalkyl), $C_1$-$C_6$haloalkyl, $C_2$-$C_6$haloalkenyl, $C_2$-$C_6$haloalkynyl, —($C_{0-6}$alkyl)($C_3$-$C_6$halocycloalkyl), —($C_3$-$C_6$cycloalkyl)($C_1$-$C_3$haloalkyl), —($C_{0-6}$alkyl)-heterocyclyl, —($C_0$-$C_6$alkyl)-heteroaryl, halogen, CN, —$C_1$-$C_4$alkyl-CN, —$C_3$-$C_6$cycloalkyl-CN, $NO_2$, $C_1$-$C_6$alkoxy, $C_1$-$C_4$haloalkoxy, $C_1$-$C_4$alkoxy-$C_1$-$C_4$alkyl, —S—$C_1$-$C_6$alkyl, —S(=O)—$C_1$-$C_6$alkyl, —S(=O)$_2$ $C_1$-$C_6$alkyl, —S(=O)(=NH)$C_1$-$C_6$alkyl, —NH—$C_1$-$C_6$alkyl, —N($C_1$-$C_6$alkyl)$_2$, —NH—$C_3$-$C_6$cycloalkyl, —($C_1$-$C_6$alkyl)($C_3$-$C_6$cycloalkyl), —C(=O)$C_1$-$C_6$alkyl, —C(=O)H, —C(=O)$C_1$-$C_6$alkoxy, —C(=O)$C_1$-$C_6$haloalkoxy, —C(=O)NH($C_1$-$C_6$alkyl), —C(=O)NH($C_1$-$C_6$haloalkyl) and —C(=O)N($C_1$-$C_6$ alkyl)$_2$;
W is $NR^1$ or O;
Y is O or S;
J is a 5- or 6-membered heteroaryl or heterocyclyl, wherein said heteroaryl and heterocyclyl is unsubstituted or substituted with one to three substituents independently selected from $C_1$-$C_6$alkyl, $C_2$-$C_6$alkenyl, $C_2$-$C_6$alkynyl, —($C_0$-$C_6$alkyl)$C_{3-8}$cycloalkyl, $C_1$-$C_6$haloalkyl, $C_2$-$C_6$haloalkenyl, $C_2$-$C_6$haloalkynyl, —($C_{0-6}$alkyl)$C_{3-8}$halocycloalkyl, —$C_3$-$C_6$cycloalkyl-$C_1$-$C_3$haloalkyl, —($C_0$-$C_6$alkyl)heterocyclyl, halogen, CN, —$C_1$-$C_4$alkyl-CN, —$C_3$-$C_6$cycloalkyl-CN, $NO_2$, $C_1$-$C_6$alkoxy, $C_1$-$C_4$haloalkoxy, —($C_1$-$C_4$alkyl)($C_1$-$C_4$alkoxy), —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$ $C_1$-$C_6$haloalkyl, —S(=O)(=NH)$C_1$-$C_6$haloalkyl, —NH($C_1$-$C_6$alkyl), —N($C_2$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_2$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;

$Ar^1$ and $Ar^2$ are independently selected from phenyl and heteroaryl, wherein said phenyl and heteroaryl are unsubstituted or substituted by one to three substituents independently selected from $C_1$-$C_6$alkyl, $C_2$-$C_6$alkenyl, $C_2$-$C_6$alkynyl, ($C_0$-$C_6$alkyl)-$C_{3-6}$cycloalkyl, $C_1$-$C_6$haloalkyl, $C_2$-$C_6$haloalkenyl, $C_2$-$C_6$haloalkynyl, —($C_0$-$C_6$alkyl)$C_{3-6}$halocycloalkyl, —$C_3$-$C_6$cycloalkyl-$C_1$-$C_3$haloalkyl, —($C_0$-$C_6$alkyl)heterocyclyl, halogen, CN, —$C_1$-$C_6$alkyl-CN, —$C_3$-$C_6$cycloalkyl-CN, $NO_2$, $C_1$-$C_6$alkoxy, $C_1$-$C_6$haloalkoxy, —($C_1$-$C_4$alkyl)($C_1$-$C_4$alkoxy), —S—$C_1$-$C_6$alkyl, —S(O)—$C_1$-$C_6$alkyl, —S(=O)$_2$$C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$$C_1$-$C_6$haloalkyl, —S(=O)(=NH)$C_1$-$C_6$haloalkyl, —NH($C_1$-$C_6$alkyl), —N($C_1$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_1$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;

$R^1$ and $R^2$ are independently selected from H, $C_1$-$C_6$-alkyl, $C_1$-$C_6$-haloalkyl, —($C_0$-$C_6$alkyl)$C_3$-$C_6$-cycloalkyl, —($C_0$-$C_6$alkyl)$C_{3-8}$halocycloalkyl, $C_2$-$C_6$-alkenyl, $C_2$-$C_6$haloalkenyl, $C_2$-$C_6$-alkynyl, $C_2$-$C_6$haloalkynyl, —($C_1$-$C_4$alkyl)O($C_1$-$C_4$alkyl), —S—$C_1$-$C_6$alkyl, —S—$C_1$-$C_6$haloalkyl, —S(=O)—$C_1$-$C_6$alkyl, —S(=O)$_2$—$C_1$-$C_6$alkyl, —S(=O)—$C_1$-$C_6$haloalkyl, —S(=O)$_2$—$C_1$-$C_6$haloalkyl, —C(=O)($C_1$-$C_6$alkyl), —C(=O)($C_1$-$C_6$alkoxy), —C(=O)NH($C_1$-$C_6$alkyl), —C(=O)N($C_1$-$C_6$alkyl)$_2$, —O—C(=O)($C_1$-$C_6$alkoxy), —O—C(=O)NH($C_1$-$C_6$alkyl), —O—C(=O)N($C_1$-$C_6$alkyl)$_2$ and —C(=N—$C_1$-$C_4$alkoxy)-$C_1$-$C_4$alkyl; provided that when $R^1$ and $R^2$ are different from H, $R^1$ and $R^2$ is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, halogen, CN, $NO_2$, $C_1$-$C_6$alkoxy, $C_1$-$C_6$haloalkoxy, —S—$C_1$-$C_6$alkyl, —S(=O)—$C_1$-$C_6$alkyl, —S(=O)$_2$$C_1$-$C_6$alkyl, —S(=O)(=NH)$C_1$-$C_6$alkyl, —NH($C_1$-$C_6$alkyl), —N($C_1$-$C_6$alkyl)$_2$, —NH($C_3$-$C_6$cycloalkyl), —N($C_1$-$C_4$alkyl)($C_3$-$C_6$cycloalkyl), —C(=O)($C_1$-$C_6$alkyl), —C(=O)($C_1$-$C_6$alkoxy, —C(=O)NH($C_1$-$C_6$alkyl) and —C(=O)($C_1$-$C_6$alkyl);

$R^3$ is selected from H, $C_1$-$C_6$-alkyl, —($C_{0-6}$alkyl)$C_3$-$C_6$-cycloalkyl, $C_2$-$C_6$-alkenyl, $C_2$-$C_6$-alkynyl, —C(=O)H, —C(=O)($C_1$-$C_6$-alkyl), —C(=O)O($C_1$-$C_6$-alkyl), —C(=O)($C_{0-6}$alkyl)($C_3$-$C_6$-cycloalkyl), —C(=O)O($C_{0-6}$alkyl)($C_3$-$C_6$-cycloalkyl)-C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), —($C_{0-6}$ alkyl)phenyl, —($C_{0-6}$ alkyl)-O-phenyl, —C(=O)—($C_0$-$C_6$-alkyl)(heteroaryl), —C(=O)—($C_0$-$C_6$-alkyl)(heterocyclyl), —($C_0$-$C_6$-alkyl)(heteroaryl), —($C_0$-$C_6$-alkyl)(heterocyclyl), —($C_0$-$C_6$-alkyl)-O-(heteroaryl), —($C_0$-$C_6$-alkyl)-O-(heterocyclyl), —($C_1$-$C_6$-alkyl)OC(=O)($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-haloalkyl), —($C_1$-$C_6$-alkyl)OC(=O)($C_1$-$C_6$-alkyl)-N($R^{3a}$)C(=O)—O—($C_{0-6}$alkyl)-phenyl, —($C_1$-$C_6$-alkyl)OC(=O)($C_1$-$C_6$-alkyl)-N($R^{3a}$)C(=O)—O—($C_{0-6}$alkyl)-heteroaryl, —($C_1$-$C_6$-alkyl)OC(=O)($C_1$-$C_6$-alkyl)-N($R^{3a}$)C(=O)—O—($C_0$-6alkyl)-heterocyclyl, —($C_1$-$C_6$-alkyl)-C(=O)N($R^{3a}$)—($C_1$-$C_6$-alkyl), —($C_1$-$C_6$-alkyl)-C(=O)N($R^{3a}$)—($C_0$-$C_6$-alkyl)-heteroaryl-C(=O)—O—($C_1$-$C_6$-alkyl), —($C_1$-$C_6$-alkyl)-C(=O)N($R^{3a}$)—($C_0$-$C_6$-alkyl)-heterocyclyl-C(=O)—O—($C_1$-$C_6$-alkyl), —($C_1$-$C_6$-alkyl)-C(=O)N($R^{3a}$)—($C_0$-$C_6$-alkyl)-heteroaryl, —($C_1$-$C_6$-alkyl)-C(=O)N($R^{3a}$)—($C_1$-$C_6$-alkyl)-heteroaryl, —($C_1$-$C_6$-alkyl)-C(=O)-heteroaryl, —($C_1$-$C_6$-alkyl)-C(=O)—($C_0$-$C_6$-alkyl)heterocyclyl, —($C_1$-$C_6$-alkyl)-C(=O)—N($R^{3a}$)($C_1$-$C_6$-alkyl)(N($R^{3a}$)($R^{3b}$))(C(=O)OH), —($C_1$-$C_6$-alkyl)-C(=O)—N($R^{3a}$)($C_1$-$C_6$-alkyl)(N($R^{3a}$)($R^{3b}$)), —($C_1$-$C_6$-alkyl)-C(=O)—N($R^{3a}$)($C_1$-$C_6$-alkyl)N($R^{3a}$)C(=O)—O—($C_1$-$C_6$-alkyl), —($C_1$-$C_6$-alkyl)-C(=O)—N($R^{3a}$)($C_1$-$C_6$-alkyl)N($R^{3a}$)C(=O)—O—($C_1$-$C_6$-alkyl)(C(=O)OH), —($C_1$-$C_6$-alkyl)-C(=O)—($C_0$-$C_6$-alkyl)heteroaryl-C(=O)—O—($C_1$-$C_6$-alkyl), —($C_1$-$C_6$-alkyl)-C(=O)—($C_0$-$C_6$-alkyl)-heterocyclyl-C(=O)—O—($C_1$-$C_6$-alkyl), —($C_1$-$C_6$-alkyl)-O—C(=O)—O—($C_1$-$C_6$-alkyl), —($C_1$-$C_6$-alkyl)-O—C(=O)O($C_1$-$C_6$-alkyl), —($C_1$-$C_6$-alkyl)-O—C(=O)($C_3$-$C_6$-cycloalkyl), —($C_1$-$C_6$-alkyl)-O—C(=O)—($C_0$-$C_6$-alkyl)heteroaryl, —($C_1$-$C_6$-alkyl)-O—C(=O)—($C_0$-$C_6$-alkyl)heterocyclyl, —($C_1$-$C_6$-alkyl)-O—C(=O)—($C_1$-$C_6$-alkyl)-N($R^{3a}$)C(=O)—O—($C_1$-$C_6$-alkyl), —($C_0$-$C_6$-alkyl)-N$R^{3a}R^{3b}$, —($C_1$-$C_6$-alkyl)-O—($C_0$-$C_6$-alkyl)heteroaryl and —($C_1$-$C_6$-alkyl)-O—($C_0$-$C_6$-alkyl)heterocyclyl;

wherein each alkyl, cycloalkyl, alkenyl, alkynyl, phenyl, heteroaryl and heterocyclyl are unsubstituted or substituted with one or more substituents independently selected from halogen, CN, $NO_2$, $NR^{3a}R^{3b}$, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-alkyl), —O—S(=O)$_2$($C_1$-$C_6$-alkyl), —O—S(=O)$_2$($C_1$-$C_6$-haloalkyl), —C(=O)H, —C(=O)OH, —C(=O)$NR^{3a}R^{3b}$, —($C_1$-$C_6$-alkyl)$NR^{3a}R^{3b}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), phenyl, —O-phenyl, —Si($C_1$-$C_6$-alkyl)$_3$, —S(=O)$NR^{3a}R^{3b}$, —S(=O)$_2NR^{3a}R^{3b}$, heteroaryl and heterocyclyl;

Z is a 4- to 7-membered heterocyclyl or heteroaryl, which heterocyclyl or heteroaryl is unsubstituted or substituted with one or two substituents independently selected from halogen, CN, $NO_2$, oxo, hydroxy, —$NR^{Za}R^{Zb}$, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-alkyl), —OS(=O)$_2$($C_1$-$C_6$-alkyl), —OS(=O)$_2$($C_1$-$C_6$-haloalkyl), —C(=O)H, —C(=O)OH, —C(=O)$NR^{Za}R^{Zb}$, —($C_1$-$C_6$-alkyl)$NR^{Za}R^{Zb}$, —C(=O)($C_1$-$C_6$-alkyl), —C(=O)O($C_1$-$C_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{Za}$R$^{Zb}$, —S(O)$_2$NR$^{Za}$R$^{Zb}$, heteroaryl and heterocyclyl;

wherein each alkyl, cycloalkyl, alkenyl, alkynyl, phenyl, heteroaryl and heterocyclyl substituent is unsubstituted or substituted with one or more substituents independently selected from halogen, CN, NO$_2$, NR$^{Za}$R$^{Zb}$, C$_1$-C$_6$-alkyl, C$_1$-C$_6$-haloalkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_2$-C$_6$-alkynyl, —S—(C$_1$-C$_6$-alkyl), —S(=O)(C$_1$-C$_6$-alkyl), —S(=O)$_2$(C$_1$-C$_6$-alkyl), —O—S(=O)$_2$(C$_1$-C$_6$-alkyl), —O—S(=O)$_2$(C$_1$-C$_6$-haloalkyl), —C(=O)H, —C(=O)OH, —C(=O)NR$^{Za}$R$^{Zb}$, —(C$_1$-C$_6$-alkyl)NR$^{Za}$R$^{Zb}$, —C(=O)(C$_1$-C$_6$-alkyl), —C(=O)O(C$_1$-C$_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{Za}$R$^{Zb}$, —S(O)$_2$NR$^{Za}$R$^{Zb}$, heteroaryl and heterocyclyl;

R$^{3a}$, R$^{3b}$, R$^{Za}$ and R$^{Zb}$ are independently selected from H, C$_1$-C$_6$-alkyl, C$_1$-C$_6$-haloalkyl, C$_3$-C$_6$-cycloalkyl and C$_1$-C$_6$-alkoxy;

or an agrochemically acceptable salt, stereoisomer, tautomer, N-oxide thereof.

2. The compound according to claim 1, of formula (Ia)

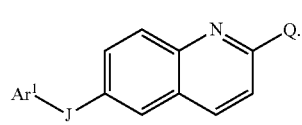

(Ia)

3. The compound according to claim 1, of formula (Ib)

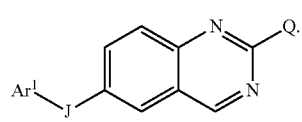

(Ib)

4. The compound according to claim 1, of formula (Ic)

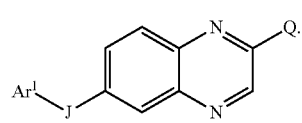

(Ic)

5. The compound according to claim 1, of formula (Id)

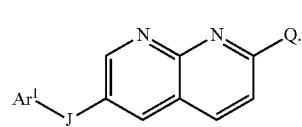

(Id)

6. The compound according to claim 1, of formula (Ie)

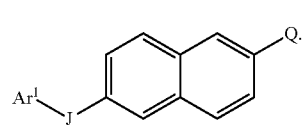

(Ie)

7. The compound according to claim 1, wherein Q is

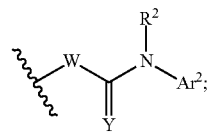

W is NH;
Y is O or S;
R$^2$ is selected from H, C$_1$-C$_6$alkyl and C$_1$-C$_6$haloalkyl;
J is

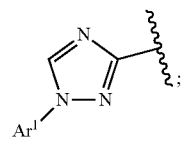

Ar$^1$ is phenyl which is unsubstituted or substituted by one to three substituents independently selected from C$_1$-C$_6$alkyl, C$_1$-C$_6$haloalkyl, halogen, C$_1$-C$_6$alkoxy and C$_1$-C$_6$haloalkoxy;

Ar$^2$ is phenyl which is unsubstituted or substituted by one to three substituents independently selected from C$_1$-C$_4$alkyl, C$_1$-C$_4$haloalkyl, halogen, C$_1$-C$_4$alkoxy and C$_1$-C$_4$haloalkoxy;

or an agrochemically acceptable salt, stereoisomer, tautomer, N-oxide thereof.

8. A compound according to claim 1, wherein Q is

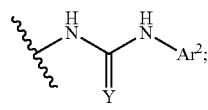

Y is O or S;
J is

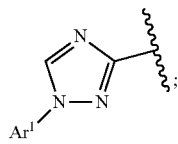

Ar¹ is

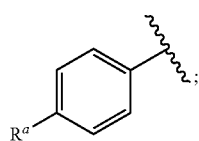

R$^a$ is selected from C$_1$-C$_6$alkyl, C$_1$-C$_6$haloalkyl, halogen, C$_1$-C$_6$alkoxy and C$_1$-C$_6$haloalkoxy;
Ar² is

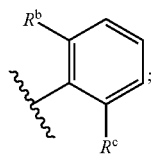

R$^b$ and R$^c$ are independently selected from H, C$_1$-C$_6$alkyl and halogen;
or an agrochemically acceptable salt, stereoisomer, tautomer, N-oxide thereof.

9. A compound according to claim 1, wherein
Q is

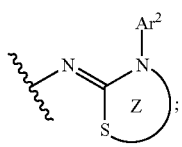

Ar² is phenyl which is unsubstituted or substituted by one to three substituents independently selected from C$_1$-C$_4$alkyl, C$_1$-C$_4$haloalkyl, halogen, C$_1$-C$_4$alkoxy and C$_1$-C$_4$haloalkoxy;
Z is a 4- to 7-membered heterocyclyl or heteroaryl, which heterocyclyl or heteroaryl is unsubstituted or substituted with one or two substituents independently selected from C$_1$-C$_6$-alkyl, C$_1$-C$_4$alkoxy, oxo and hydroxy;
or an agrochemically acceptable salt, stereoisomer, tautomer, N-oxide thereof.

10. A compound according to claim 1, wherein
Q is

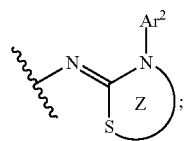

Ar² is

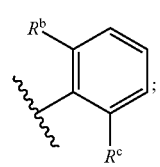

R$^b$ and R$^c$ are independently selected from H, C$_1$-C$_6$alkyl and halogen;
Z is a 5 or 6-membered heterocyclyl or heteroaryl, which heterocyclyl or heteroaryl is unsubstituted or substituted with one or two substituents independently selected from C$_1$-C$_6$-alkyl, oxo and hydroxy;
or an agrochemically acceptable salt, stereoisomer, tautomer, N-oxide thereof.

11. A compound according to claim 1, wherein
Q is

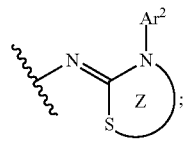

Ar² is

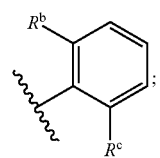

R$^b$ and R$^c$ are independently selected from H, C$_1$-C$_6$alkyl and halogen;
Z is a 5-membered heterocyclyl or heteroaryl, which heterocyclyl or heteroaryl is unsubstituted or substituted with one or two substituents independently selected from C$_1$-C$_6$-alkyl, oxo and hydroxy;
or an agrochemically acceptable salt, stereoisomer, tautomer, N-oxide thereof.

12. A compound according to claim 1, wherein Q is

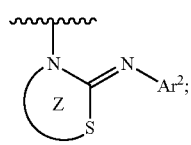

$Ar^2$ is

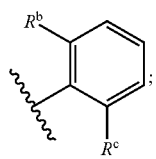

$R^b$ and $R^c$ are independently selected from H, $C_1$-$C_6$alkyl and halogen;

Z is a 5 or 6-membered heterocyclyl or heteroaryl, which heterocyclyl or heteroaryl is unsubstituted or substituted with one or two substituents independently selected from $C_1$-$C_6$-alkyl, oxo and hydroxy;

or an agrochemically acceptable salt, stereoisomer, tautomer, N-oxide thereof.

13. A compound according to claim 1, wherein Q is

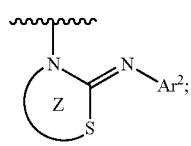

$Ar^2$ is

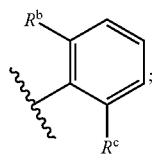

$R^b$ and $R^c$ are independently selected from H, $C_1$-$C_6$alkyl and halogen;

Z is a 5-membered heterocyclyl or heteroaryl, which heterocyclyl or heteroaryl is unsubstituted or substituted with one or two substituents independently selected from $C_1$-$C_6$-alkyl, oxo and hydroxy;

or an agrochemically acceptable salt, stereoisomer, tautomer, N-oxide thereof.

14. A pesticidal composition, which comprises at least one compound according to claim 1, or an agrochemically acceptable salt, stereoisomer, tautomer, N-oxide thereof, as active ingredient and at least one auxiliary.

15. The composition according to claim 14, which further comprises one or more other insecticidally, acaricidally, nematicidally and/or fungicidally active agents.

16. A method for controlling pests, which comprises applying a composition according to claim 14 to the pests or their environment with the exception of a method for treatment of the human or animal body by surgery or therapy and diagnostic methods practised on the human or animal body.

17. A method for the protection of plant propagation material from the attack by pests, which comprises treating the propagation material or the site, where the propagation material is planted, with a composition according to claim 14.

18. A coated plant propagation material, wherein the coating of the plant propagation material comprises a compound as defined claim 1.

19. A compound of formula (I')

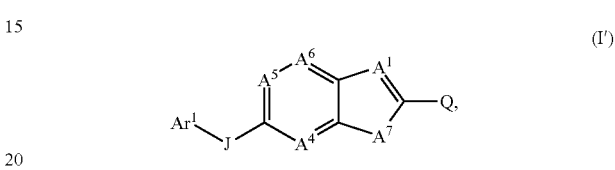

wherein Q is selected from

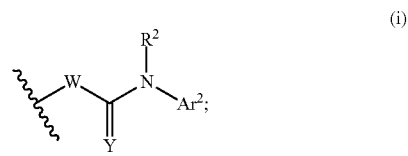

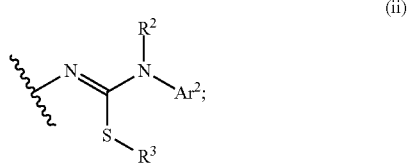

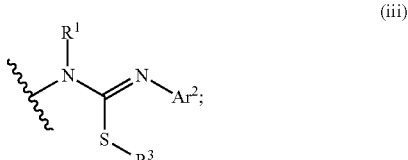

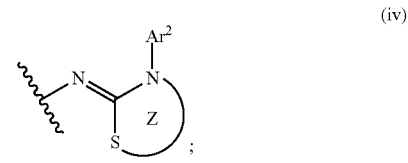

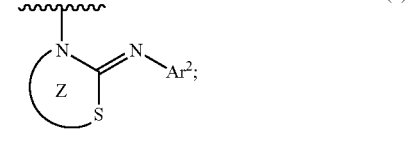

$A^1$ is N or $CR^{A1}$;
$A^4$ is N or $CR^{A4}$;
$A^5$ is N or $CR^{A5}$;
$A^6$ is N or $CR^{A6}$;
$A^7$ is O or S;
with the proviso that not more than four of $A^1$, $A^4$, $A^5$ and $A^6$ are N;
$R^{A1}$, $R^{A4}$, $R^{A5}$ and $R^{A6}$ are independently selected from H, $C_1$-$C_6$alkyl, $C_2$-$C_6$alkenyl, $C_2$-$C_6$alkynyl, —($C_0$-$C_6$alkyl)($C_{3-6}$cycloalkyl), $C_1$-$C_6$haloalkyl, $C_2$-$C_6$haloalkenyl, $C_2$-$C_6$haloalkynyl, —($C_{0-6}$alkyl)

($C_3$-$C_6$halocycloalkyl), —($C_3$-$C_6$cycloalkyl)($C_1$-$C_3$haloalkyl), —($C_{0-6}$alkyl)-heterocyclyl, —($C_0$-$C_6$alkyl)-heteroaryl, halogen, CN, —$C_1$-$C_4$alkyl-CN, —$C_3$-$C_6$cycloalkyl-CN, NO$_2$, $C_1$-$C_6$alkoxy, $C_1$-$C_4$haloalkoxy, $C_1$-$C_4$alkoxy-$C_1$-$C_4$alkyl, —S—$C_1$-$C_6$alkyl, —S(=O)—$C_1$-$C_6$alkyl, —S(=O)$_2$$C_1$-$C_6$alkyl, —S(=O)(=NH)$C_1$-$C_6$alkyl, —NH—$C_1$-$C_6$alkyl, —N($C_1$-$C_6$alkyl)$_2$, —NH—$C_3$-$C_6$cycloalkyl, —N($C_1$-$C_6$alkyl)($C_3$-$C_6$cycloalkyl), —C(=O)$C_1$-$C_6$alkyl, —C(=O)H, —C(=O)$C_1$-$C_6$alkoxy, —C(=O)$C_1$-$C_6$haloalkoxy, —C(=O)NH($C_1$-$C_6$alkyl), —C(=O)NH($C_1$-$C_6$haloalkyl) and —C(=O)N($C_1$-$C_6$ alkyl)$_2$;

W is NR$^1$ or O;

Y is O or S;

J is a 5- or 6-membered heteroaryl or heterocyclyl, wherein said heteroaryl and heterocyclyl is unsubstituted;

R$^1$ and R$^2$ are independently selected from H, $C_1$-$C_6$-alkyl, $C_1$-$C_6$-haloalkyl, —($C_0$-$C_6$alkyl)$C_3$-$C_6$-cycloalkyl, —($C_0$-$C_6$alkyl)$C_{3-8}$halocycloalkyl, $C_2$-$C_6$-alkenyl, $C_2$-$C_6$haloalkenyl, $C_2$-$C_6$-alkynyl, $C_2$-$C_6$haloalkynyl, —($C_1$-$C_4$alkyl)O($C_1$-$C_4$alkyl), —S—$C_1$-$C_6$alkyl, —S—$C_1$-$C_6$haloalkyl, —S(=O)—$C_1$-$C_6$alkyl, —S(=O)$_2$—$C_1$-$C_6$alkyl, —S(=O)—$C_1$-$C_6$haloalkyl, —S(=O)$_2$—$C_1$-$C_6$haloalkyl, —C(=O)($C_1$-$C_6$alkyl), —C(=O)($C_1$-$C_6$alkoxy), —C(=O)NH($C_1$-$C_6$alkyl), —C(=O)N($C_1$-$C_6$alkyl)$_2$, —O—C(=O)($C_1$-$C_6$alkoxy), —O—C(=O)NH($C_1$-$C_6$alkyl), —O—C(=O)N($C_1$-$C_6$alkyl)$_2$ and —C(=N—$C_1$-$C_4$alkoxy)-$C_1$-$C_4$alkyl; provided that when R$^1$ and R$^2$ are different from H, R$^1$ and R$^2$ is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, halogen, CN, NO$_2$, $C_1$-$C_6$alkoxy, $C_1$-$C_6$haloalkoxy, —S—$C_1$-$C_6$alkyl, —S(=O)—$C_1$-$C_6$alkyl, —S(=O)$_2$$C_1$-$C_6$alkyl, —S(=O)(=NH)$C_1$-$C_6$alkyl, —NH($C_1$-$C_6$alkyl), —N($C_1$-$C_6$alkyl)$_2$, —NH($C_3$-$C_6$cycloalkyl), —N($C_1$-$C_4$alkyl)($C_3$-$C_6$cycloalkyl), —C(=O)($C_1$-$C_6$alkyl), —C(=O)($C_1$-$C_6$alkoxy, —C(=O)NH($C_1$-$C_6$alkyl) and —C(=O)($C_1$-$C_6$alkyl);

R$^3$ is selected from H, $C_1$-$C_6$-alkyl, —($C_{0-6}$alkyl)$C_3$-$C_6$-cycloalkyl, $C_2$-$C_6$-alkenyl, $C_2$-$C_6$-alkynyl, —C(=O) H, —C(=O)($C_1$-$C_6$-alkyl), —C(=O)O($C_1$-$C_6$-alkyl), —C(=O)($C_{3-6}$alkyl)($C_3$-$C_6$-cycloalkyl), —C(=O)O($C_{1-6}$alkyl)($C_3$-$C_6$-cycloalkyl)-C(=O)($C_2$-$C_6$-alkenyl), —Cs(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), —($C_{0-6}$alkyl) phenyl, —($C_{0-6}$alkyl)-O-phenyl, —C(=O)—($C_0$-$C_6$-alkyl)(heteroaryl), —C(=O)—($C_0$-$C_6$-alkyl)(heterocyclyl), —($C_0$-$C_6$-alkyl)(heteroaryl), —($C_0$-$C_6$-alkyl)(heterocyclyl), —($C_0$-$C_6$-alkyl)-O-(heteroaryl), —($C_0$-$C_6$-alkyl)-O-(heterocyclyl), —($C_1$-$C_6$-alkyl)OC(=O)($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-haloalkyl), —($C_1$-$C_6$-alkyl)OC(=O)($C_1$-$C_6$-alkyl)-N(R$^{3a}$)C(=O)—O—($C_{0-6}$alkyl)-phenyl, —($C_1$-$C_6$-alkyl)OC(=O)($C_1$-$C_6$-alkyl)-N(R$^{3a}$)C(=O)—O—($C_{0-6}$alkyl)-heterocyclyl, —($C_1$-$C_6$-alkyl)OC(=O)($C_1$-$C_6$-alkyl)-N(R$^{3a}$)C(=O)—O—($C_{0-6}$alkyl)-heterocyclyl, —($C_1$-$C_6$-alkyl)-C(=O)N(R$^{3a}$)—($C_1$-$C_6$-alkyl), —($C_1$-$C_6$-alkyl)-C(=O)N(R$^{3a}$)—($C_0$-$C_6$-alkyl)-heteroaryl-C(=O)—O—($C_1$-$C_6$-alkyl), —($C_1$-$C_6$-alkyl)-C(=O)N(R$^{3a}$)—($C_0$-$C_6$-alkyl)-heterocyclyl-C(=O)—O—($C_1$-$C_6$-alkyl), —($C_1$-$C_6$-alkyl)-C(=O)N(R$^{3a}$)—($C_0$-$C_6$-alkyl)-heteroaryl, —($C_1$-$C_6$-alkyl)-C(=O)N(R$^{3a}$)—($C_0$-$C_6$-alkyl)-heterocyclyl, —($C_1$-$C_6$-alkyl)-C(=O)-heteroaryl, —($C_1$-$C_6$-alkyl)-C(=O)—($C_0$-$C_6$-alkyl) heterocyclyl, —($C_1$-$C_6$-alkyl)-C(=O)—N(R$^{3a}$)($C_1$-$C_6$-alkyl)(N(R$^{3a}$)(R$^{3b}$))(C(=O)OH), —($C_1$-$C_6$-alkyl)-C(=O)—N(R$^{3a}$)($C_1$-$C_6$-alkyl)(N(R$^{3a}$)(R$^{3b}$)), —($C_1$-$C_6$-alkyl)-C(=O)—N(R$^{3a}$)($C_1$-$C_6$-alkyl)N(R$^{3a}$)C(=O)—O—($C_1$-$C_6$-alkyl), —($C_1$-$C_6$-alkyl)-C(=O)—N(R$^{3a}$)($C_0$-$C_6$-alkyl)N(R$^{3a}$)C(=O)—O—($C_1$-$C_6$-alkyl)(C(=O)OH), —($C_1$-$C_6$-alkyl)-C(=O)—($C_0$-$C_6$-alkyl)heteroaryl-C(=O)—O—($C_1$-$C_6$-alkyl), —($C_1$-$C_6$-alkyl)-C(=O)—($C_0$-$C_6$-alkyl)-heterocyclyl-C(=O)—O—($C_1$-$C_6$-alkyl), —($C_1$-$C_6$-alkyl)-O—C(=O)—O—($C_1$-$C_6$-alkyl), —($C_1$-$C_6$-alkyl)-O—C(=O)($C_1$-$C_6$-alkyl), —($C_1$-$C_6$-alkyl)-O—C(=O)($C_3$-$C_6$-cycloalkyl), —($C_1$-$C_6$-alkyl)-O—C(=O)—($C_0$-$C_6$-alkyl)heteroaryl, —($C_1$-$C_6$-alkyl)-O—C(=O)($C_0$-$C_6$-alkyl)heterocyclyl, —($C_1$-$C_6$-alkyl)-O—C(=O)—($C_1$-$C_6$-alkyl)-N(R$^{3a}$)C(=O)—O—($C_1$-$C_6$-alkyl), —($C_0$-$C_6$-alkyl)-NR$^{3a}$R$^{3b}$, —($C_1$-$C_6$-alkyl)-O—($C_0$-$C_6$-alkyl)heteroaryl and —($C_1$-$C_6$-alkyl)-O—($C_0$-$C_6$-alkyl)heterocyclyl;

wherein each alkyl, cycloalkyl, alkenyl, alkynyl, phenyl, heteroaryl and heterocyclyl are unsubstituted or substituted with one or more substituents independently selected from halogen, CN, NO$_2$, NR$^{3a}$R$^{3b}$, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-alkyl), —O—S(=O)$_2$($C_1$-$C_6$-alkyl), —O—S(=O)$_2$($C_1$-$C_6$-haloalkyl), —C(=O)H, —C(=O)OH, —C(=O)NR$^{3a}$R$^{3b}$, —($C_1$-$C_6$-alkyl)NR$^{3a}$R$^{3b}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), phenyl, —O-phenyl, —Si($C_1$-$C_6$-alkyl)$_3$, —S(=O)NR$^{3a}$R$^{3b}$, —S(=O)$_2$NR$^{3a}$R$^{3b}$, heteroaryl and heterocyclyl;

Z is a 4- to 7-membered heterocyclyl or heteroaryl, which heterocyclyl or heteroaryl is unsubstituted or substituted with one or two substituents independently selected from halogen, CN, NO$_2$, oxo, hydroxy, —NR$^{Za}$R$^{Zb}$, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-haloalkyl), —OS(=O)$_2$($C_1$-$C_6$-alkyl), —OS(=O)$_2$($C_1$-$C_6$-haloalkyl), —C(=O)H, —C(=O)OH, —(=O)NR$^{Za}$R$^{Zb}$, —($C_1$-$C_6$-alkyl)NR$^{Za}$R$^{Zb}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), phenyl, —O-phenyl, —Si($C_1$-$C_6$-alkyl)$_3$, —S(=O)NR$^{Za}$R$^{Zb}$, —S(O)$_2$NR$^{Za}$R$^{Zb}$, heteroaryl and heterocyclyl;

wherein each alkyl, cycloalkyl, alkenyl, alkynyl, phenyl, heteroaryl and heterocyclyl substituent is unsubstituted or substituted with one or more substituents independently selected from halogen, CN, NO$_2$, NR$^{Za}$R$^{Zb}$, C$_1$-C$_6$-alkyl, C$_1$-C$_6$-haloalkyl, C$_3$-C$_6$-cycloalkyl, C$_3$-C$_6$-halocycloalkyl, C$_1$-C$_6$-alkoxy, C$_1$-C$_6$-haloalkoxy, C$_2$-C$_6$-alkenyl, C$_2$-C$_6$-alkynyl, —S—(C$_1$-C$_6$-alkyl), —S(=O)(C$_1$-C$_6$-alkyl), —S(=O)$_2$(C$_1$-C$_6$-alkyl), —O—S(=O)$_2$(C$_1$-C$_6$-alkyl), —O—S(=O)$_2$(C$_1$-C$_6$-haloalkyl), —C(=O)H, —C(=O)OH, —C(=O)NR$^{Za}$R$^{Zb}$, —(C$_1$-C$_6$-alkyl)NR$^{Za}$R$^{Zb}$, —C(=O)(C$_1$-C$_6$-alkyl), —C(=O)O(C$_1$-C$_6$-alkyl), —C(=O)(C$_1$-C$_6$-haloalkyl), —C(=O)O(C$_1$-C$_6$-haloalkyl), —C(=O)(C$_3$-C$_6$-cycloalkyl), —C(=O)O(C$_3$-C$_6$-cycloalkyl), —C(=O)(C$_2$-C$_6$-alkenyl), —C(=O)O(C$_2$-C$_6$-alkenyl), —(C$_1$-C$_6$-alkyl)O(C$_1$-C$_6$-alkyl), —(C$_1$-C$_6$-alkyl)S(C$_1$-C$_6$-alkyl), —C(=O)(C$_1$-C$_6$-alkyl)C(=O)O(C$_1$-C$_6$-alkyl), phenyl, —O-phenyl, —Si(C$_1$-C$_6$-alkyl)$_3$, —S(=O)NR$^{Za}$R$^{Zb}$, —S(=O)$_2$NR$^{Za}$R$^{Zb}$, heteroaryl and heterocyclyl;

R$^{3a}$, R$^{3b}$, R$^{Za}$ and R$^{Zb}$, are independently selected from H, C$_1$-C$_6$-alkyl, C$_1$-C$_6$-haloalkyl, C$_3$-C$_6$-cycloalkyl and C$_1$-C$_6$-alkoxy;

or an agrochemically acceptable salt, stereoisomer, tautomer, N-oxide thereof.

20. The compound according to claim 19, wherein J is a triazole.

21. The compound according to claim 19, of formula (If)

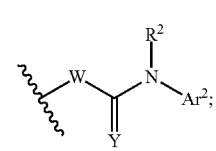

(If)

22. A compound of formula (I')

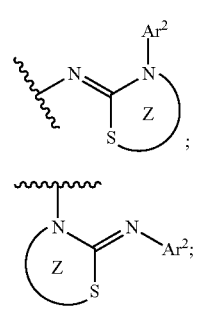

(I')

wherein Q is selected from

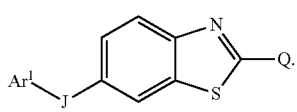

(i)

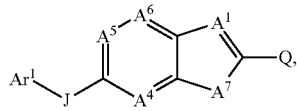

(ii)

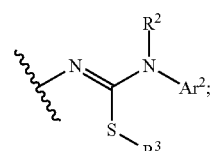

(iii)

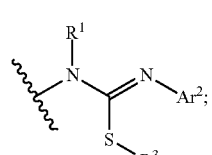

(iv)

(v)

A$^1$ is N or CR$^{A1}$;
A$^4$ is N or CR$^{A4}$;
A$^5$ is N or CR$^{A5}$;
A$^6$ is N or CR$^{A6}$;
A$^7$ is O or S;
with the proviso that not more than four of A$^1$, A$^4$, A$^5$ and A$^6$ are N;
R$^{A1}$, R$^{A4}$, R$^{A5}$ and R$^{A6}$ are independently selected from H, C$_1$-C$_6$alkyl, C$_2$-C$_6$alkenyl, C$_2$-C$_6$alkynyl, —(C$_0$-C$_6$alkyl)(C$_{3-6}$cycloalkyl), C$_1$-C$_6$haloalkyl, C$_2$-C$_6$haloalkenyl, C$_2$-C$_6$haloalkynyl, —(C$_{0-6}$alkyl)(C$_3$-C$_6$halocycloalkyl), —(C$_3$-C$_6$cycloalkyl)(C$_1$-C$_3$haloalkyl), —(C$_{0-6}$alkyl)-heterocyclyl, —(C$_0$-C$_6$alkyl)-heteroaryl, halogen, CN, —C$_1$-C$_4$alkyl-CN, —C$_3$-C$_6$cycloalkyl-CN, NO$_2$, C$_1$-C$_6$alkoxy, C$_1$-C$_4$haloalkoxy, C$_1$-C$_4$alkoxy-C$_1$-C$_4$alkyl, —S—C$_1$-C$_6$alkyl, —S(=O)—C$_1$-C$_6$alkyl, —S(=O)$_2$C$_1$-C$_6$alkyl, —S(=O)(=NH)C$_1$-C$_6$alkyl, —NH—C$_1$-C$_6$alkyl, —N(C$_1$-C$_6$alkyl)$_2$, —NH—C$_3$-C$_6$cycloalkyl, —N(C$_1$-C$_6$alkyl)(C$_3$-C$_6$cycloalkyl), —C(=O)C$_1$-C$_6$alkyl, —C(=O)H, —C(=O)C$_1$-C$_6$alkoxy, —C(=O)C$_1$-C$_6$haloalkoxy, —C(=O)NH(C$_1$-C$_6$alkyl), —C(=O)NH(C$_1$-C$_6$haloalkyl) and —C(=O)N(C$_1$-C$_6$ alkyl)$_2$;
W is NR$^1$ or O;
Y is O or S;
J is a 5- or 6-membered heteroaryl or heterocyclyl, wherein said heteroaryl and heterocyclyl is bonded by a heteroatom and unsubstituted or substituted with one to three substituents independently selected from C$_1$-C$_6$alkyl, C$_2$-C$_6$alkenyl, C$_2$-C$_6$alkynyl, —(C$_0$-C$_6$alkyl)C$_{3-8}$cycloalkyl, C$_1$-C$_6$haloalkyl, C$_2$-C$_6$haloalkenyl, C$_2$-C$_6$haloalkynyl, —(C$_{0-6}$ alkyl)C$_{3-8}$ halocycloalkyl, —C$_3$-C$_6$cycloalkyl-C$_1$-C$_3$haloalkyl, —(C$_0$-C$_6$alkyl)heterocyclyl, halogen, CN, —C$_1$-C$_4$alkyl-CN, —C$_3$-C$_6$cycloalkyl-CN, NO$_2$, C$_1$-C$_6$alkoxy, C$_1$-C$_4$haloalkoxy, —(C$_1$-C$_4$alkyl)(C$_1$-C$_4$alkoxy), —S—C$_1$-C$_6$alkyl, —S(O)—C$_1$-C$_6$alkyl, —S(=O)$_2$ C$_1$-C$_6$alkyl, —S(=O)(=NH)C$_1$-C$_6$alkyl, —S—C$_1$-C$_6$haloalkyl, —S(O)—C$_1$-C$_6$haloalkyl, —S(=O)$_2$ C$_1$-C$_6$haloalkyl, —S(=O)(=NH)C$_1$-C$_6$haloalkyl, —NH(C$_1$-C$_6$alkyl), —N(C$_2$-C$_6$alkyl)$_2$, —NH(C$_3$-C$_6$cycloalkyl), —N(C$_1$-C$_6$alkyl)(C$_3$-C$_6$cycloalkyl), —C(=O)(C$_1$-C$_6$alkyl), CHO, —C(=O)(C$_2$-C$_6$alkoxy), —C(=O)(C$_1$-C$_6$haloalkoxy), —C(=C)NH(C$_1$-C$_6$alkyl), —C(=O)NH(C$_1$-C$_6$haloalkyl) and —C(=O)N(C$_1$-C$_6$alkyl)$_2$;
Ar$^1$ and Ar$^2$ are independently selected from phenyl and heteroaryl, wherein said phenyl and heteroaryl are unsubstituted or substituted by one to three substituents independently selected from C$_1$-C$_6$alkyl, C$_2$-C$_6$alkenyl, C$_2$-C$_6$alkynyl, (C$_0$-C$_6$alkyl)-C$_{3-6}$ cycloalkyl, $C_1$-$C_6$haloalkyl, $C_2$-$C_6$haloalkenyl, $C_2$-$C_6$haloalkynyl, —($C_0$-$C_6$alkyl)$C_{3-6}$halocycloalkyl, —$C_3$-$C_6$cycloalkyl-$C_1$-$C_3$haloalkyl, —($C_0$-$C_6$alkyl)heterocyclyl, halogen, CN, —$C_1$-$C_6$alkyl-CN, —$C_3$-$C_6$cycloalkyl-CN, $NO_2$, $C_1$-$C_6$alkoxy, $C_1$-$C_6$haloalkoxy, —($C_1$-$C_4$alkyl)($C_1$-$C_4$alkoxy), —S—$C_1$-$C_6$alkyl, —S(O)—$C_1$-$C_6$alkyl, —S(=O)$_2$$C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$$C_1$-$C_6$haloalkyl, —S(=O)(=NH)$C_1$-$C_6$haloalkyl, —NH($C_1$-$C_6$alkyl), —N($C_1$-$C_6$alkyl)$_2$, —NH($C_3$-$C_6$cycloalkyl), —N($C_1$-$C_6$alkyl)($C_3$-$C_6$cycloalkyl), —C(=O)($C_1$-$C_6$alkyl), CHO, —C(=O)($C_1$-$C_6$alkoxy), —C(=O)($C_1$-$C_6$haloalkoxy), —C(=O)NH($C_1$-$C_6$alkyl), —C(=O)NH($C_1$-$C_6$haloalkyl) and —C(=O)N($C_1$-$C_6$alkyl)$_2$;

$R^1$ and $R^2$ are independently selected from H, $C_1$-$C_6$-alkyl, $C_1$-$C_6$-haloalkyl, —($C_0$-$C_6$alkyl)$C_3$-$C_6$-cycloalkyl, —($C_0$-$C_6$alkyl)$C_{3-8}$halocycloalkyl, $C_2$-$C_6$-alkenyl, $C_2$-$C_6$haloalkenyl, $C_2$-$C_6$-alkynyl, $C_2$-$C_6$haloalkynyl, —($C_1$-$C_4$alkyl)O($C_1$-$C_4$alkyl), —S—$C_1$-$C_6$alkyl, —S—$C_1$-$C_6$haloalkyl, —S(=O)—$C_1$-$C_6$alkyl, —S(=O)$_2$—$C_1$-$C_6$alkyl, —S(=O)—$C_1$-$C_6$haloalkyl, —S(=O)$_2$—$C_1$-$C_6$haloalkyl, —C(=O)($C_1$-$C_6$alkyl), —C(=O)($C_1$-$C_6$alkoxy), —C(=O)NH($C_1$-$C_6$alkyl), —C(=O)N($C_1$-$C_6$alkyl)$_2$, —O—C(=O)($C_1$-$C_6$alkoxy), —O—C(=O)NH($C_1$-$C_6$alkyl), —O—C(=O)N($C_1$-$C_6$alkyl)$_2$ and —C(=N—$C_1$-$C_4$alkoxy)-$C_1$-$C_4$alkyl; provided that when $R^1$ and $R^2$ are different from H, $R^1$ and $R^2$ is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, halogen, CN, $NO_2$, $C_1$-$C_6$alkoxy, $C_1$-$C_6$haloalkoxy, —S—$C_1$-$C_6$alkyl, —S(=O)—$C_1$-$C_6$alkyl, —S(=O)$_2$$C_1$-$C_6$alkyl, —S(=O)(=NH)$C_1$-$C_6$alkyl, —NH($C_1$-$C_6$alkyl), —N($C_1$-$C_6$alkyl)$_2$, —NH($C_3$-$C_6$cycloalkyl), —N($C_1$-$C_4$alkyl)($C_3$-$C_6$cycloalkyl), —C(=O)($C_1$-$C_6$alkyl), —C(=O)($C_1$-$C_6$alkoxy, —C(=O)NH($C_1$-$C_6$alkyl) and —C(=O)($C_1$-$C_6$alkyl);

$R^3$ is selected from H, $C_1$-$C_6$-alkyl, —($C_{0-6}$alkyl)$C_3$-$C_6$-cycloalkyl, $C_2$-$C_6$-alkenyl, $C_2$-$C_6$-alkynyl, —C(=O)H, —C(=O)($C_1$-$C_6$-alkyl), —C(=O)O($C_1$-$C_6$-alkyl), —C(=O)($C_{0-6}$ alkyl)($C_3$-$C_6$-cycloalkyl), —C(=O)O($C_0$-$6$alkyl)($C_3$-$C_6$-cycloalkyl)-C(=O)($C_2$-$C_6$-alkenyl), —Cs(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), —($C_{0-6}$ alkyl)phenyl, —($C_{0-6}$ alkyl)-O-phenyl, —C(=O)—($C_0$-$C_6$-alkyl)(heteroaryl), —C(=O)—($C_0$-$C_6$-alkyl)(heterocyclyl), —($C_0$-$C_6$-alkyl)(heteroaryl), —($C_1$-$C_6$-alkyl)(heterocyclyl), —($C_0$-$C_6$-alkyl)-O-(heteroaryl), —($C_0$-$C_6$-alkyl)-O-(heterocyclyl), —($C_1$-$C_6$-alkyl)OC(=O)($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-alkyl)-O—($C_1$-$C_6$-alkyl), —($C_1$-$C_6$-alkyl)OC(=O)($C_1$-$C_6$-alkyl)-O—($C_1$-$C_6$-haloalkyl), —($C_1$-$C_6$-alkyl)OC(=O)($C_1$-$C_6$-alkyl)-N($R^{3a}$)C(=O)—O—($C_{0-6}$alkyl)-phenyl, —($C_1$-$C_6$-alkyl)OC(=O)($C_1$-$C_6$-alkyl)-N($R^{3a}$)C(=O)—O—($C_{0-6}$alkyl)-heteroaryl, —($C_1$-$C_6$-alkyl)OC(=O)($C_1$-$C_6$-alkyl)-N($R^{3a}$)C(=O)—O—($C_{0-6}$alkyl)-heterocyclyl, —($C_1$-$C_6$-alkyl)-C(=O)N($R^{3a}$)—($C_1$-$C_6$-alkyl), —($C_1$-$C_6$-alkyl)-C(=O)N($R^{3a}$)—($C_0$-$C_6$-alkyl)-heteroaryl-C(=O)—O—($C_1$-$C_6$-alkyl), —($C_1$-$C_6$-alkyl)-C(=O)N($R^{3a}$)—($C_0$-$C_6$-alkyl)-heterocyclyl-C(=O)—O—($C_1$-$C_6$-alkyl), —($C_1$-$C_6$-alkyl)-C(=O)N($R^{3a}$)—($C_0$-$C_6$-alkyl)-heteroaryl, —($C_1$-$C_6$-alkyl)-C(=O)N($R^{3a}$)—($C_0$-$C_6$-alkyl)-heterocyclyl, —($C_1$-$C_6$-alkyl)-C(=O)-heteroaryl, —($C_1$-$C_6$-alkyl)-C(=O)—($C_0$-$C_6$-alkyl)heterocyclyl, —($C_1$-$C_6$-alkyl)-C(=O)—N($R^{3a}$)($C_1$-$C_6$-alkyl)(N($R^{3a}$)($R^{3b}$))(C(=O)OH), —($C_1$-$C_6$-alkyl)-C(=O)—N($R^{3a}$)($C_1$-$C_6$-alkyl)(N($R^{3a}$)($R^{3b}$)), —($C_1$-$C_6$-alkyl)-C(=O)—N($R^{3a}$)($C_1$-$C_6$-alkyl)N($R^{3a}$)C(=O)—O—($C_1$-$C_6$-alkyl), —($C_1$-$C_6$-alkyl)-C(=O)—N($R^{3a}$)($C_1$-$C_6$-alkyl)N($R^{3a}$)C(=O)—O—($C_1$-$C_6$-alkyl)(C(=O)OH), —($C_1$-$C_6$-alkyl)-C(=O)—($C_0$-$C_6$-alkyl)heteroaryl-C(=O)—O—($C_1$-$C_6$-alkyl), —($C_1$-$C_6$-alkyl)-C(=O)—($C_0$-$C_6$-alkyl)-heterocyclyl-C(=O)—O—($C_1$-$C_6$-alkyl), —($C_1$-$C_6$-alkyl)-O—C(=O)—O—($C_1$-$C_6$-alkyl), —($C_1$-$C_6$-alkyl)-O—C(=O)($C_1$-$C_6$-alkyl), —($C_1$-$C_6$-alkyl)-O—C(=O)($C_3$-$C_6$-cycloalkyl), —($C_1$-$C_6$-alkyl)-O—C(=O)—($C_0$-$C_6$-alkyl)heteroaryl, —($C_1$-$C_6$-alkyl)-O—C(=O)($C_0$-$C_6$-alkyl)heterocyclyl, —($C_1$-$C_6$-alkyl)-O—C(=O)—($C_1$-$C_6$-alkyl)-N($R^{3a}$)C(=O)—O—($C_1$-$C_6$-alkyl), —($C_0$-$C_6$-alkyl)-N$R^{3a}R^{3b}$, —($C_1$-$C_6$-alkyl)-O—($C_0$-$C_6$-alkyl)heteroaryl and —($C_1$-$C_6$-alkyl)-O—($C_0$-$C_6$-alkyl)heterocyclyl;

wherein each alkyl, cycloalkyl, alkenyl, alkynyl, phenyl, heteroaryl and heterocyclyl are unsubstituted or substituted with one or more substituents independently selected from halogen, CN, $NO_2$, N$R^{3a}R^{3b}$, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-alkyl), —O—S(=O)$_2$($C_1$-$C_6$-alkyl), —O—S(=O)$_2$($C_1$-$C_6$-haloalkyl), —C(=O)H, —C(=O)OH, —C(=O)N$R^{3a}R^{3b}$, —($C_1$-$C_6$-alkyl)N$R^{3a}R^{3b}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), phenyl, —O-phenyl, —Si($C_1$-$C_6$-alkyl)$_3$, —S(=O)N$R^{3a}R^{3b}$, —S(=O)$_2$N$R^{3a}R^{3b}$, heteroaryl and heterocyclyl;

Z is a 4- to 7-membered heterocyclyl or heteroaryl, which heterocyclyl or heteroaryl is unsubstituted or substituted with one or two substituents independently selected from halogen, CN, $NO_2$, oxo, hydroxy, —N$R^{Za}R^{Zb}$, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-haloalkyl), —OS(=O)$_2$($C_1$-$C_6$-alkyl), —OS(=O)$_2$($C_1$-$C_6$-haloalkyl), —C(=O)H, —C(=O)OH, —C(=O)N$R^{Za}R^{Zb}$, —($C_1$-$C_6$-alkyl)N$R^{Za}R^{Zb}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), phenyl, —O-phenyl, —Si($C_1$-$C_6$-alkyl)$_3$, —S(=O)N$R^{Za}R^{Zb}$, —S(O)$_2$N$R^{Za}R^{Zb}$, heteroaryl and heterocyclyl;

wherein each alkyl, cycloalkyl, alkenyl, alkynyl, phenyl, heteroaryl and heterocyclyl substituent is unsubstituted or substituted with one or more substituents independently selected from halogen, CN, $NO_2$, N$R^{Za}R^{Zb}$, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_2$-$C_6$-alkenyl, $C_2$-$C_6$-alkynyl, —S—($C_1$-$C_6$-alkyl), —S(=O)($C_1$-$C_6$-alkyl), —S(=O)$_2$($C_1$-$C_6$-alkyl), —O—S(=O)$_2$($C_1$-$C_6$-alkyl), —O—S(=O)$_2$($C_1$-$C_6$-haloalkyl), —C(=O)H, —C(=O)OH, —C(=O)NR$^{Za}$R$^{Zb}$, —($C_1$-$C_6$-alkyl)NR$^{Za}$R$^{Zb}$, —C(=O)($C_1$-$C_6$-alkyl), —C(=O)O($C_1$-$C_6$-alkyl), —C(=O)($C_1$-$C_6$-haloalkyl), —C(=O)O($C_1$-$C_6$-haloalkyl), —C(=O)($C_3$-$C_6$-cycloalkyl), —C(=O)O($C_3$-$C_6$-cycloalkyl), —C(=O)($C_2$-$C_6$-alkenyl), —C(=O)O($C_2$-$C_6$-alkenyl), —($C_1$-$C_6$-alkyl)O($C_1$-$C_6$-alkyl), —($C_1$-$C_6$-alkyl)S($C_1$-$C_6$-alkyl), —C(=O)($C_1$-$C_6$-alkyl)C(=O)O($C_1$-$C_6$-alkyl), phenyl, —O-phenyl, —Si($C_1$-$C_6$-alkyl)$_3$, —S(=O)NR$^{Za}$R$^{Zb}$, —S(=O)$_2$NR$^{Za}$R$^{Zb}$, heteroaryl and heterocyclyl;

R$^{3a}$, R$^{3b}$, R$^{Za}$ and R$^{Zb}$ are independently selected from H, $C_1$-$C_6$-alkyl, $C_1$-$C_6$-haloalkyl, $C_3$-$C_6$-cycloalkyl and $C_1$-$C_6$-alkoxy;

or an agrochemically acceptable salt, stereoisomer, tautomer, N-oxide thereof.

23. The compound according to claim 22, wherein J is a substituted or unsubstituted triazole.

\* \* \* \* \*